(12) United States Patent
Tapper et al.

(10) Patent No.: US 11,338,152 B2
(45) Date of Patent: *May 24, 2022

(54) LIGHT THERAPY BANDAGE

(71) Applicant: Johnson & Johnson Consumer Inc., Skillman, NJ (US)

(72) Inventors: Jay Tapper, Wayne, PA (US); Lulin Ding, Brooklyn, NY (US); Charles Peter Althoff, New York, NY (US); Kayla Marie Nickley, Columbus, OH (US); Jens Peter Johnson, Austin, TX (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 585 days.

This patent is subject to a terminal disclaimer.

(21) Appl. No.: 16/159,263

(22) Filed: Oct. 12, 2018

(65) Prior Publication Data
US 2019/0111278 A1     Apr. 18, 2019

Related U.S. Application Data

(63) Continuation-in-part of application No. 15/782,548, filed on Oct. 12, 2017, now abandoned.

(51) Int. Cl.
*A61N 5/06*     (2006.01)
*A61B 18/00*    (2006.01)

(52) U.S. Cl.
CPC ......... *A61N 5/0616* (2013.01); *A61N 5/0625* (2013.01); *A61B 2018/00642* (2013.01);
(Continued)

(58) Field of Classification Search
CPC ........... A61B 2018/00642; A61B 2018/00791; A61B 2018/00988; A61B 5/259; A61B 18/20–18/28; A61N 5/06–2005/073; A61N 2005/0626; A61N 2005/0627; A61N 2005/0645; A61N 2005/0651;
(Continued)

(56) References Cited

U.S. PATENT DOCUMENTS 4,981,135 A * 1/1991 Hardy ................. A61F 7/02
                                                    602/2
5,612,680 A * 3/1997 DeSanto ............ G01R 31/58
                                                    340/815.45
(Continued)

FOREIGN PATENT DOCUMENTS

CN      103476455 A     12/2013
WO      WO 01/14012 A1   3/2001
(Continued)

*Primary Examiner* — Jonathan T Kuo
*Assistant Examiner* — Vynn V Huh
(74) *Attorney, Agent, or Firm* — Fay Sharpe LLP

(57) ABSTRACT

A radiant energy bandage assembly is disclosed. According to an exemplary embodiment, the radiant energy bandage assembly comprises an encased flexible PCBA (Printed Circuit Board Assembly) including a plurality of radiant lamps and a plurality of apertures aligned with the plurality (Continued)

of radiant lamps. A control pod docking interface operatively connected to the flexible PCBA provides an interface to operatively connect a user control pod to control a dosage of radiant energy to a user treatment area.

18 Claims, 68 Drawing Sheets

(52) U.S. Cl.
CPC ............... *A61B 2018/00791* (2013.01); *A61B 2018/00988* (2013.01); *A61N 2005/0626* (2013.01); *A61N 2005/0627* (2013.01); *A61N 2005/0645* (2013.01); *A61N 2005/0651* (2013.01); *A61N 2005/0652* (2013.01); *A61N 2005/0654* (2013.01); *A61N 2005/0659* (2013.01); *A61N 2005/0663* (2013.01)

(58) Field of Classification Search
CPC .... A61N 2005/0652; A61N 2005/0654; A61N 2005/0659; A61N 2005/0663; A61N 5/0616; A61N 5/0625; A61N 1/0452; A61N 1/0456; A61N 1/046; A61N 1/0472; A61N 1/0476; A61N 1/048; A61N 1/0492; A61N 1/0496; A61N 1/36014; A61N 1/3603; A61N 1/36031; A61N 1/36034; A61N 1/205; A61N 1/326; A61N 1/328; A61F 2007/0246; A61F 2007/0247

USPC ...................... 607/50, 152, 88–94; 606/2–19
See application file for complete search history.

(56) References Cited

U.S. PATENT DOCUMENTS

| | | | |
|---|---|---|---|
| 2006/0142828 A1* | 6/2006 | Schorr | A61F 7/034 607/108 |
| 2006/0235495 A1* | 10/2006 | Tsai | A61F 7/02 607/96 |
| 2011/0054267 A1* | 3/2011 | Fidacaro | A61B 5/0002 600/300 |
| 2012/0232621 A1* | 9/2012 | Kriksunov | A61F 7/034 607/114 |
| 2014/0012360 A1* | 1/2014 | Griesser | A61N 1/0472 607/142 |
| 2015/0290470 A1* | 10/2015 | Tapper | A61N 5/0616 607/91 |
| 2017/0224990 A1* | 8/2017 | Goldwasser | A61N 1/0456 |
| 2019/0038226 A1* | 2/2019 | Davidson | A61B 5/447 |

FOREIGN PATENT DOCUMENTS

| | | |
|---|---|---|
| WO | WO 2016/007798 A2 | 1/2016 |
| WO | 2016209856 A1 | 12/2016 |
| WO | WO 2016/209856 A1 | 12/2016 |
| WO | WO 2017/127368 A1 | 7/2017 |

* cited by examiner

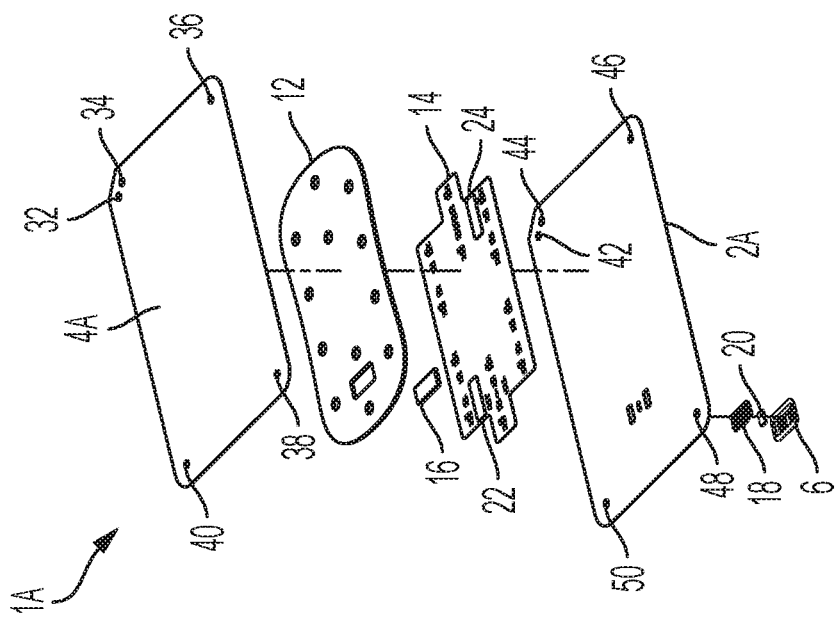
FIG. 4
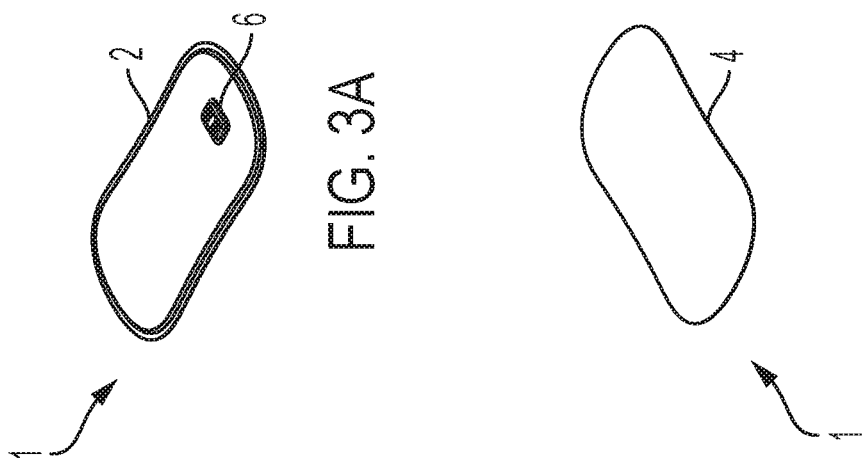
FIG. 3A
FIG. 3B

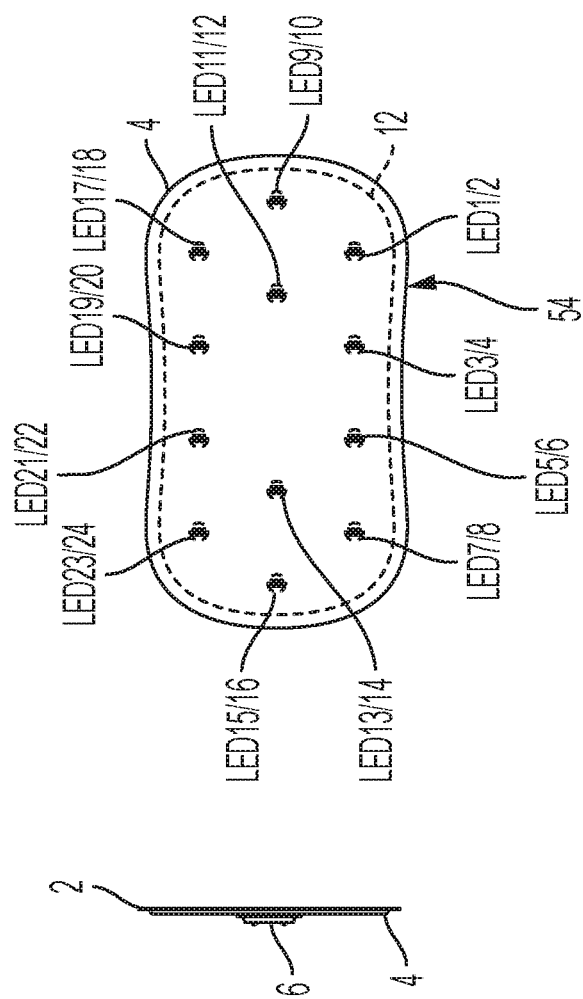
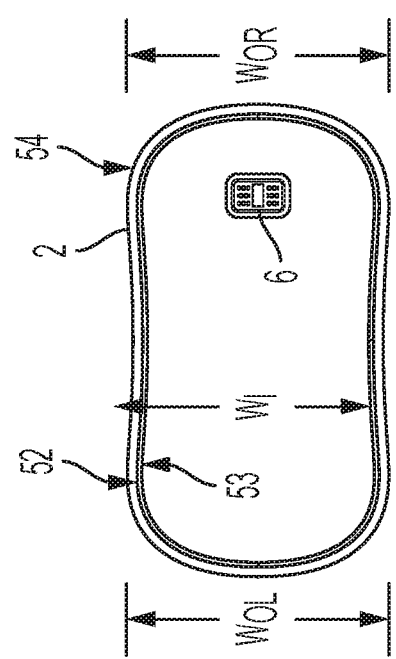
FIG. 6C
FIG. 6B
FIG. 6A

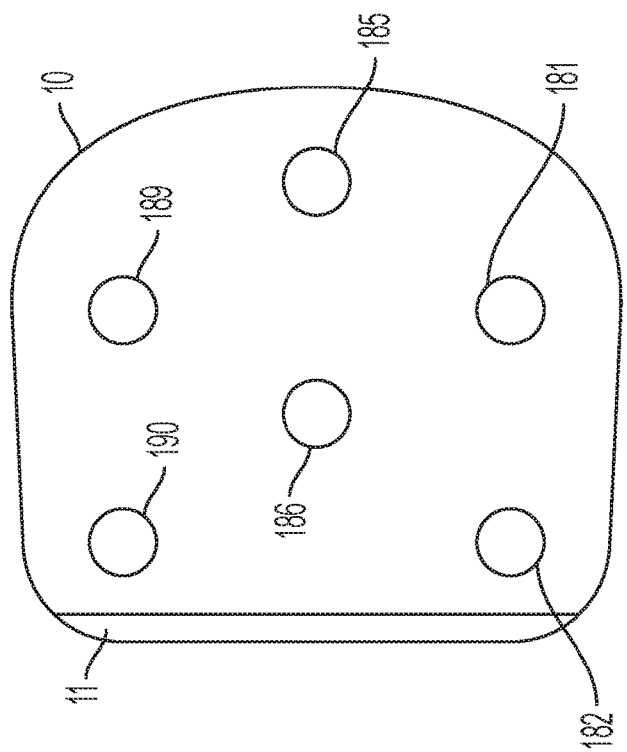
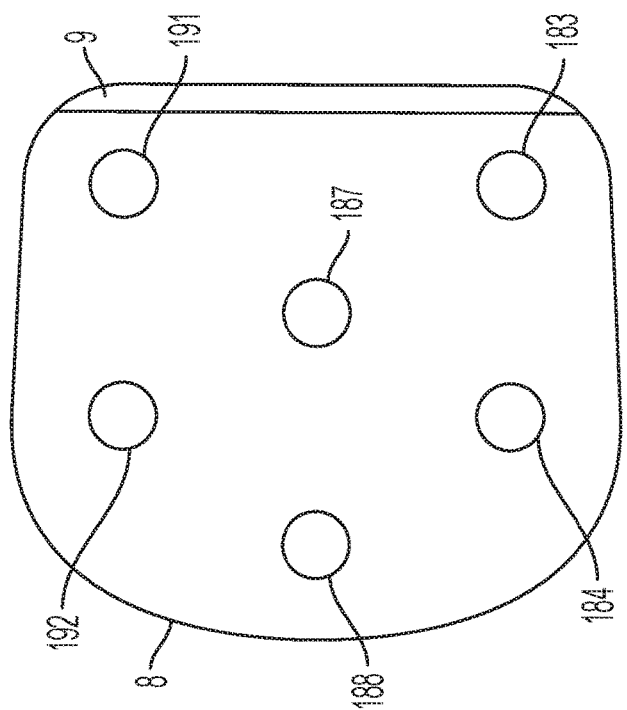
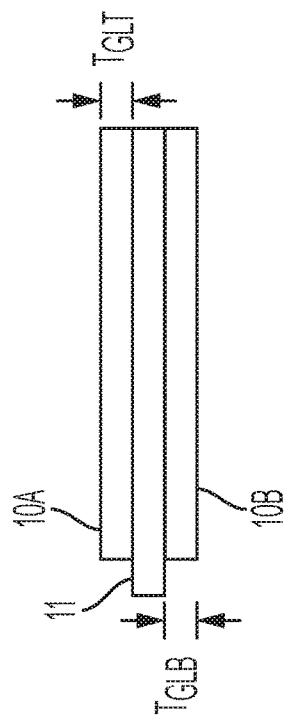
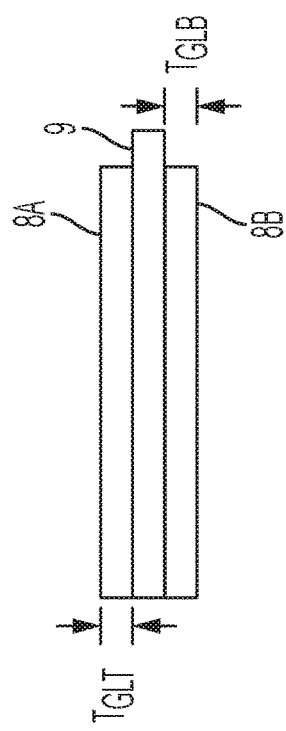
FIG. 19B
FIG. 19D
FIG. 19A
FIG. 19C

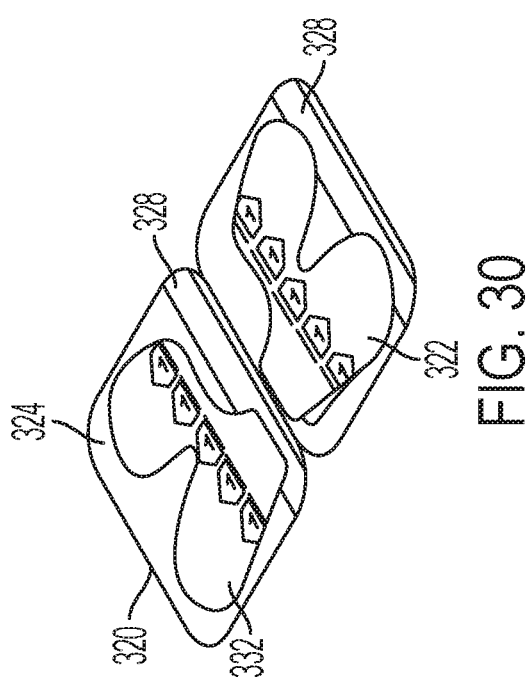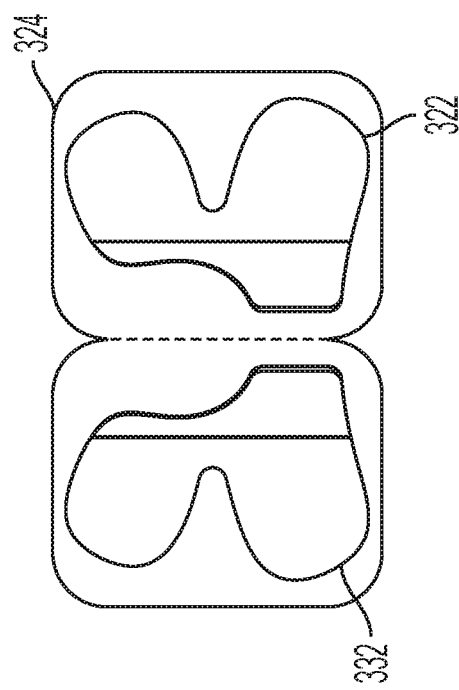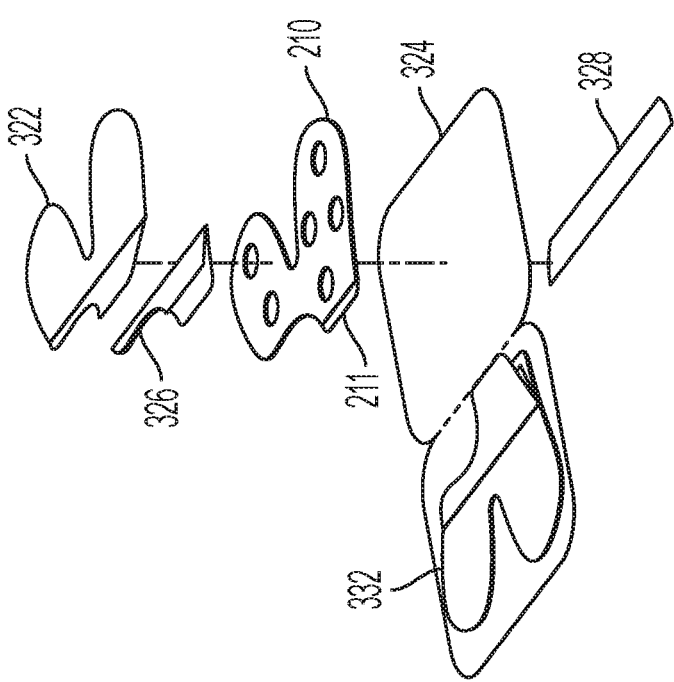

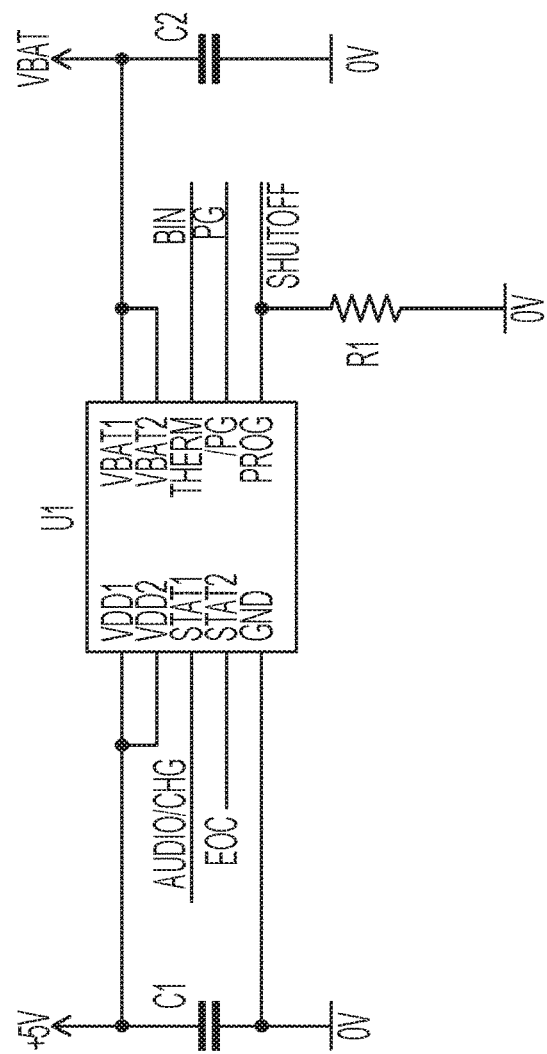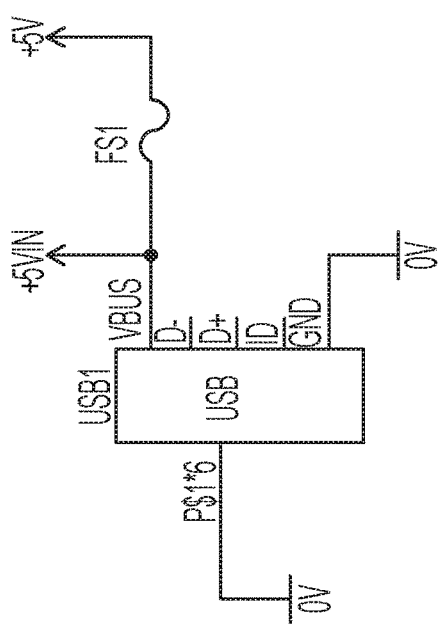
FIG. 43A

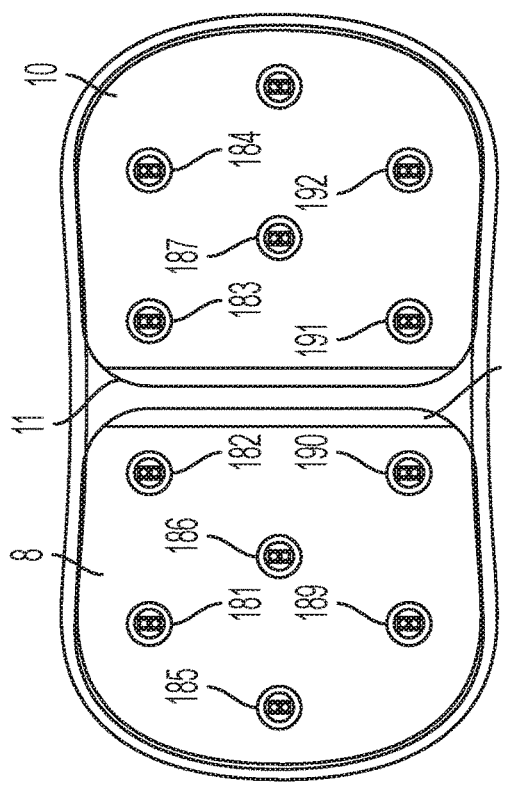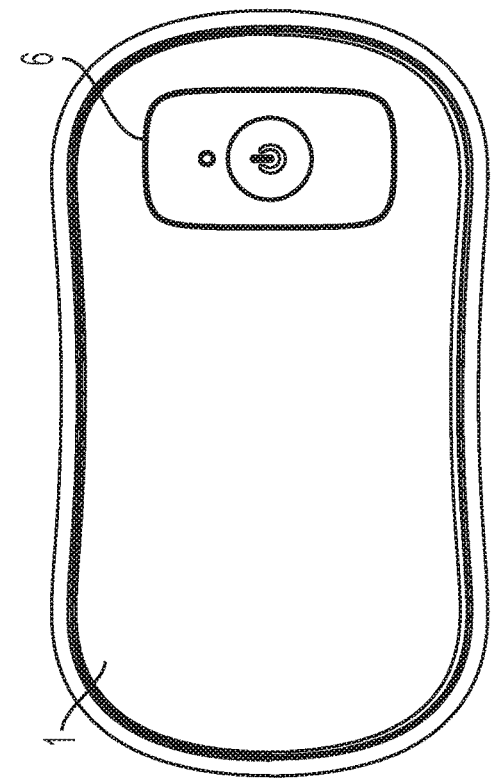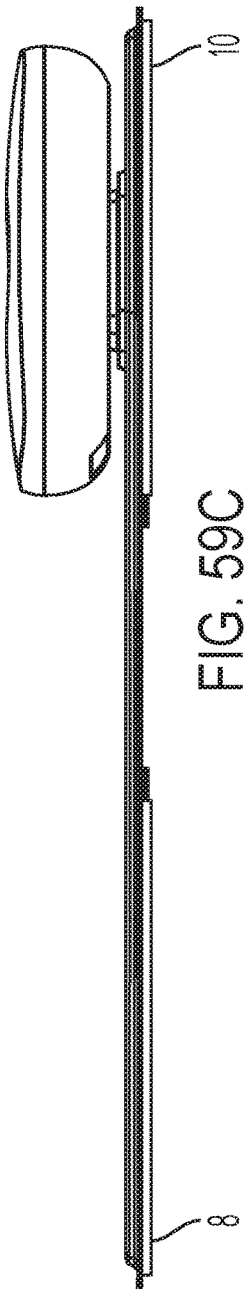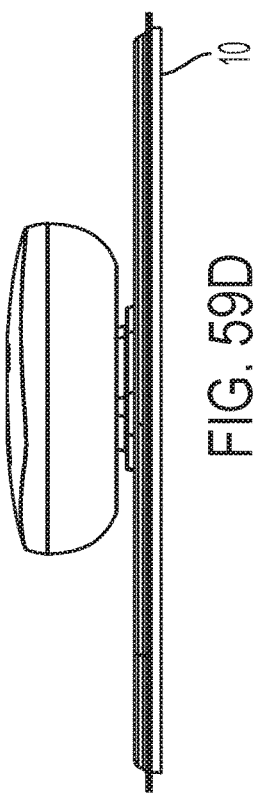

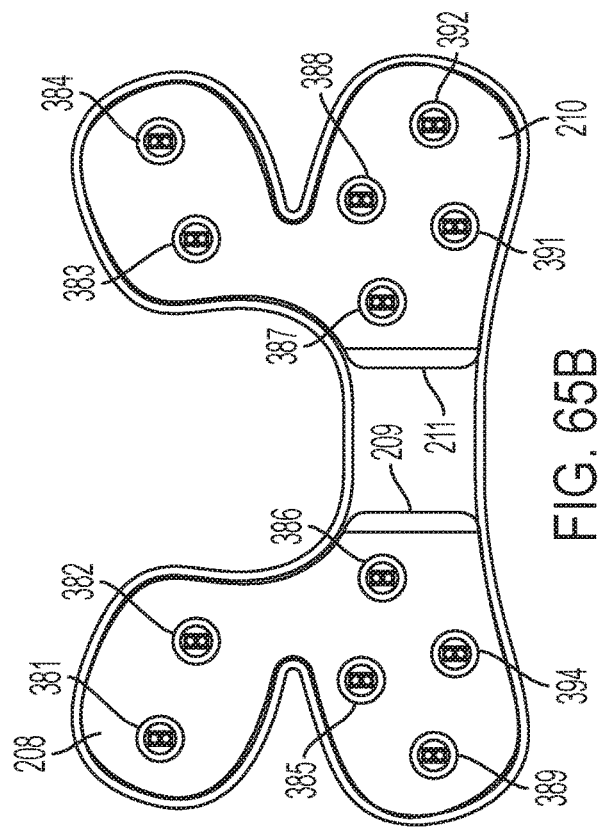
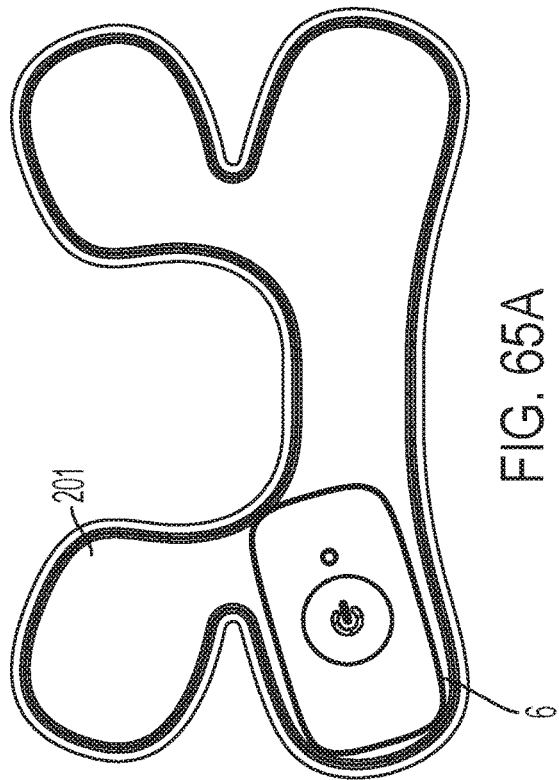
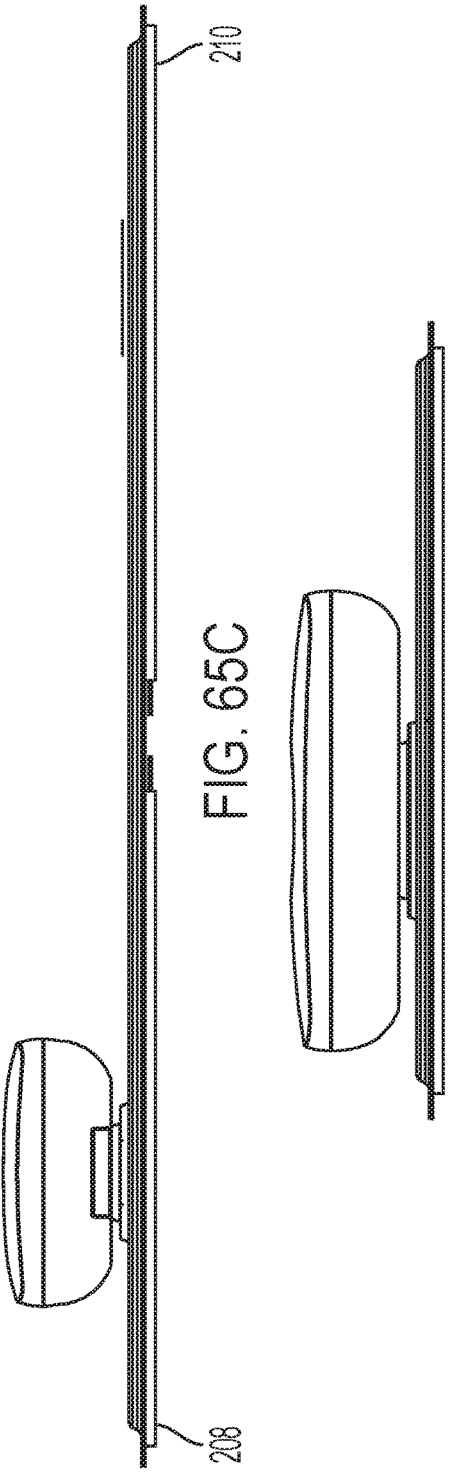
FIG. 65A
FIG. 65B
FIG. 65C
FIG. 65D

LIGHT THERAPY BANDAGE

PRIORITY

This application is a continuation-in-part of "Light Therapy Bandage System", U.S. patent application Ser. No. 15/782,548, filed on Oct. 12, 2017, the disclosure of which is incorporated by reference herein in its entirety.

INCORPORATION BY REFERENCE

"Light Therapy Bandage System", U.S. Patent Publication No. US 2014/0277298 A1, published on Sep. 18, 2014, by Tapper et al., and "Light Therapy Bandage System", U.S. Patent Publication No. 2015/0290470 A1, published on Oct. 15, 2015, by Tapper et al., the disclosures of which are incorporated herein by reference in their entirety.

FIELD

The present embodiments relate to devices and methods for delivering light-based therapy treatments for improving skin health, and/or relieving subdermal tissue using light-emitting diode (LED) light therapy, although other types of light radiating sources can be used.

BACKGROUND

Certain light spectrums emitted by LEDs (blue, red and Infrared) are known to be therapeutic for skin treatment by being beneficial to better facilitate wound healing and/or relieving muscular or other subdermal tissue pain. However, there is a need to provide users/patients with a convenient at-home light therapy delivery device such as a wearable bandage that is adjustable or flexible to conform to different sizes and shapes, and that is simple to use without user discomfort. The alternative is visiting a doctor's office to receive treatments.

Some, prior known light therapy devices have suffered from problems relating to the exposure of the LEDs and the associated circuitry to power the LEDs to contact by users. More particularly, in an effort to maximize light communication to a patient, the LEDs have been disposed in a manner which allow them to be physically engaged (e.g., touched) by a patient, or even contact a treatment surface, which processes are debilitating to the LEDs as a result of the accumulation of dirt and oil. In addition, any such engagement can be potentially dangerous to patients who are exposed to the sharp or hot edges of the LEDs and the associated circuitry. The exposure of detailed circuitry presents an intimidating and unpleasant experience.

Another problem with some prior known devices is that the LED arrangement is fixed and not adjustable to better correspond to wound location, size or shape, or to be better placed relative to pain areas. The LEDs of such devices are not selectively arrangeable in a variety of patterns to better enable the application of the device near particular pain areas of a wound.

It is desired to provide alternative means of using the benefits of the light therapy in a manner to maximize therapeutic efficiencies in exposure while maintaining ease and convenience of use. For this reason, a variety of light weight, flexible and adjustable embodiments are disclosed within this disclosure incorporating a variety of energy varying applications responsive to user conditions or needs.

SUMMARY

In one embodiment of this disclosure, described is a radiant energy bandage pad assembly comprising: a flexible PCBA (Printed Circuit Board Assembly) including a plurality of radiant lamps configured to provide radiant energy to a user treatment area; a flexible reflective pad including a top surface and a radiant energy reflective bottom surface, the reflective pad including a plurality of radiant energy communication areas aligned with the flexible PCBA plurality of radiant lamps to communicate the radiant energy from the plurality of radiant lamps through the plurality of radiant energy communication areas and exiting the reflective bottom surface; a flexible radiant energy transparent bottom cover layer covering the reflective bottom surface of the flexible reflective pad and plurality of radiant energy communication areas associated with the bottom surface of the flexible reflective pad; a replaceable flexible conformable adhesive layer attached to the radiant energy transparent layer, the replaceable flexible conformable adhesive layer including a plurality of radiant energy communication areas aligned with the flexible reflective pad plurality of radiant energy communication areas to communicate the radiant energy exiting the radiant energy transparent layer through the flexible conformable adhesive layer plurality of radiant energy communication areas to the user treatment area, and the flexible conformable adhesive layer including a top surface and a bottom surface, the top surface adapted to be removably attached by a user to cover the radiant energy transparent cover layer and the bottom surface adapted to be removably attached by the user to cover and conform to the user treatment area; a control pod docking interface operatively connected to the plurality of radiant lamps and configured to operatively connect a control pod to control the plurality of radiant lamps to provide a dosage of radiant energy to the user treatment area; and a flexible top cover layer covering the flexible PCBA and attached to the flexible radiant energy transparent bottom cover layer to encase the flexible PCBA and flexible reflective pad, and the top cover layer adapted to provide user access to the control pod docking interface.

In another embodiment of this disclosure, described is a radiant energy bandage pad assembly comprising: a flexible PCBA (Printed Circuit Board Assembly) including a plurality of radiant lamps configured to provide radiant energy to a user treatment area; a flexible reflective pad including a top surface and a radiant energy reflective bottom surface, the reflective pad including a plurality of radiant energy communication areas aligned with the flexible PCBA plurality of radiant lamps to communicate the radiant energy from the plurality of radiant lamps through the plurality of radiant energy communication areas and exiting the reflective bottom surface; a flexible radiant energy transparent bottom cover layer covering the reflective bottom surface of the flexible reflective pad and plurality of radiant energy communication areas associated with the bottom surface of the flexible reflective pad; a replaceable flexible conformable adhesive layer attached to the radiant energy transparent layer, the replaceable flexible conformable adhesive layer including a plurality of radiant energy communication areas aligned with the flexible reflective pad plurality of radiant energy communication areas to communicate the radiant energy exiting the radiant energy transparent layer through the flexible conformable adhesive layer plurality of radiant energy communication areas to the user treatment area, and the flexible conformable adhesive layer including a top surface and a bottom surface, the top surface adapted to be removably attached by a user to cover the radiant energy transparent cover layer and the bottom surface adapted to be removably attached by the user to cover and conform to the user treatment area; a control pod docking interface operatively connected to the plurality of radiant lamps and configured to operatively connect a control pod to control the plurality of radiant lamps to provide a dosage of radiant energy to the user treatment area; a flexible top cover layer covering the flexible PCBA and attached to the flexible radiant energy transparent bottom cover layer to encase the flexible PCBA and flexible reflective pad, and the top cover layer adapted to provide user access to the control pod docking interface; and a control pod operatively connected to the control pod docking interface and configured to control the plurality of radiant lamps to provide the dosage of radiant energy to the user treatment area.

In still another embodiment of this disclosure, described is a radiant energy bandage assembly comprising: a flexible PCBA (Printed Circuit Board Assembly) including a plurality of radiant energy lamps configured to provide radiant energy to a user treatment area; a flexible pad including a top surface and a bottom surface, the pad including a plurality of radiant energy communication areas aligned with the flexible PCBA plurality of radiant lamps to communicate the radiant energy from the plurality of radiant lamps through the plurality of radiant energy communication areas and exiting the bottom surface; a flexible radiant energy transparent bottom cover layer covering the bottom surface of the flexible pad and plurality of radiant energy communication areas associated with the bottom surface of the flexible pad; a control pod operatively connected to the plurality of radiant lamps and configured to control the plurality of radiant lamps to provide a dosage of radiant energy to the user treatment area; and a flexible top cover layer covering the flexible PCBA and including one or more openings to operatively connect the control pod to the plurality of radiant lamps, wherein the flexible PCBA, flexible pad, flexible radiant energy transparent bottom cover layer and flexible top cover layer are substantially symmetrically u-shaped and include a right region and left region, each of the right region and left region including a first lobe and second lobe providing a portion of the dosage of radiant energy to the user treatment area.

In still another embodiment of this disclosure, described is a radiant energy bandage assembly comprising: a flexible PCBA (Printed Circuit Board Assembly) including a plurality of radiant energy lamps configured to provide radiant energy to a user treatment area; a flexible pad including a top surface and a bottom surface, the pad including a plurality of radiant energy communication areas aligned with the flexible PCBA plurality of radiant lamps to communicate the radiant energy from the plurality of radiant lamps through the plurality of radiant energy communication areas and exiting the bottom surface; a flexible radiant energy transparent bottom cover layer covering the bottom surface of the flexible pad and plurality of radiant energy communication areas associated with the bottom surface of the flexible pad; a control pod operatively connected to the plurality of radiant lamps and configured to control the plurality of radiant lamps to provide a dosage of radiant energy to the user treatment area; and a flexible top cover layer covering the flexible PCBA and including one or more openings to operatively connect the control pod to the plurality of radiant lamps, wherein the flexible PCBA, flexible pad, flexible radiant energy transparent bottom cover layer and flexible top cover layer are substantially rectangular shaped with curved corners and includes a right region and left region, each of the right region and left region including a lobe providing a portion of the dosage of radiant energy to the user treatment area.

In another embodiment of this disclosure, described is a method of manufacturing a radiant energy bandage pad assembly, the radiant energy bandage pad assembly including a flexible PCBA (Printed Circuit Board Assembly) including a plurality of rigid radiant lamps configured to provide radiant energy to a user treatment area; a flexible pad including a plurality of radiant energy communication areas aligned with the flexible PCBA plurality of radiant lamps to communicate the radiant energy from the plurality of radiant lamps through the plurality of radiant energy communication areas and exiting the bottom surface; a flexible radiant energy transparent bottom cover layer covering the bottom surface of the flexible pad and plurality of radiant energy communication areas associated with the bottom surface of the pad; and a flexible top cover layer covering the flexible PCBA and attached to the flexible radiant energy transparent bottom cover layer to encase the flexible PCBA and flexible pad, the method comprising: a) providing an oversize flexible radiant energy transparent bottom cover layer and oversize flexible top cover layer; b) substantially centering the flexible PCBA and flexible pad between the oversized flexible radiant energy transparent bottom cover layer and flexible top cover layer; c) spot welding the oversized flexible radiant energy transparent bottom cover layer to the flexible top cover layer, the spot welds placed at regions of the oversized flexible radiant energy transparent bottom cover layer and oversized flexible top cover outside a final cut-perimeter of the flexible radiant energy transparent bottom cover and a final cut-perimeter of the flexible top cover layer; d) perimeter welding the oversized flexible radiant energy transparent bottom cover layer to the flexible top cover layer to encase the flexible PCBA and flexible pad between the oversized flexible radiant energy transparent bottom layer and flexible top cover layer, the perimeter welding substantially near and outside a perimeter of the flexible pad, thereby encasing the flexible PCBA and flexible pad between the radiant energy transparent bottom and cover layer and the flexible top cover layer; and e) simultaneously perimeter cutting the oversized flexible radiant energy transparent bottom cover layer and oversized flexible top cover layer substantially near and outside the perimeter welding.

In still another embodiment of this disclosure, described is a radiant energy therapeutic pad assembly comprising: a flexible pad assembly including a plurality of radiant energy lamps configured to provide radiant energy to a user treatment area and a magnetic docking interface attached to the flexible pad and configured to dock an external rigid pod configured to operatively provide one or both of power and control to the plurality of radiant energy lamps, the magnetic docking interface including an electrical contact assembly with symmetrically located electrical contacts and a fixed magnet substantially located near a center of the electrical contact assembly.

In yet another embodiment of this disclosure, described is a radiant energy bandage assembly comprising: a plurality of radiant lamps configured to provide radiant energy to a user treatment area; a flexible pad including a plurality of radiant energy communication areas aligned with the plurality of radiant lamps; and a control pod magnetic docking interface operatively connected to the plurality of radiant lamps and configured to magnetically dock and operatively connect a control pod to control the plurality of radiant lamps to provide a dosage of radiant energy to the user treatment area.

In still another embodiment of this disclosure, described is a radiant energy bandage assembly comprising a flexible PCBA (Printed Circuit Board Assembly) including a plurality of radiant lamps configured to provide radiant energy to a user treatment area; a flexible PCBA cover including a top surface and a bottom surface, the PCBA cover including a plurality of radiant energy communication areas aligned with the flexible PCBA plurality of radiant lamps to communicate the radiant energy from the plurality of radiant lamps through the plurality of radiant energy communication areas and exiting the bottom surface; a flexible radiant energy bottom cover layer covering the flexible PCBA cover bottom surface and the plurality of radiant energy communication areas associated with the bottom surface of the flexible PCBA cover, the flexible radiant energy bottom cover layer including a plurality of radiant energy communication areas aligned with the flexible PCBA cover plurality of radiant energy communication areas; a replaceable flexible conformable thermal conduction layer attached to the flexible radiant energy bottom cover layer, the replaceable flexible conformable thermal conduction layer including a plurality of radiant energy communication areas aligned with the flexible radiant energy bottom cover layer plurality of radiant energy communication areas to communicate the radiant energy exiting the flexible radiant energy bottom cover layer through the flexible conformable thermal conduction layer plurality of radiant energy communication areas to the user treatment area, and the flexible conformable thermal conduction layer including a top surface and a bottom surface, the top surface adapted to be removably attached by a user to cover the flexible radiant energy bottom cover layer and the bottom surface adapted to cover and conform to the user treatment area; a control pod docking interface operatively connected to the plurality of radiant lamps and configured to operatively connect a control pod to control the plurality of radiant lamps to provide a dosage of radiant energy to the user treatment area; and a flexible top cover layer covering the flexible PCBA and attached to the flexible radiant energy bottom cover layer to encase the flexible PCBA and flexible PCBA cover, and the top cover layer adapted to provide user access to the control pod docking interface.

In another embodiment, described is a radiant energy bandage assembly comprising a flexible PCBA (Printed Circuit Board Assembly) including a plurality of radiant lamps configured to provide radiant energy to a user treatment area; a flexible PCBA cover including a top surface and a bottom surface, the PCBA cover including a plurality of radiant energy communication areas aligned with the flexible PCBA plurality of radiant lamps to communicate the radiant energy from the plurality of radiant lamps through the plurality of radiant energy communication areas and exiting the bottom surface; a flexible radiant energy bottom cover layer covering the flexible PCBA cover bottom surface and the plurality of radiant energy communication areas associated with the bottom surface of the flexible PCBA cover, the flexible radiant energy bottom cover layer including a plurality of radiant energy communication areas aligned with the flexible PCBA cover plurality of radiant energy communication areas; a replaceable flexible conformable thermal conduction layer attached to the flexible radiant energy bottom cover layer, the replaceable flexible conformable thermal conduction layer including a plurality of radiant energy communication areas aligned with the flexible radiant energy bottom cover layer plurality of radiant energy communication areas to communicate the radiant energy exiting the flexible radiant energy bottom cover layer through the flexible conformable thermal conduction layer plurality of radiant energy communication areas to the user treatment area, and the flexible conformable thermal conduction layer including a top surface and a bottom surface, the top surface adapted to be removably attached by a user to cover the flexible radiant energy bottom cover layer and the bottom surface adapted to cover and conform to the user treatment area; a controller operatively connected to the plurality of radiant lamps and configured to operatively control the plurality of radiant lamps to provide a dosage of radiant energy to the user treatment area; and a flexible top cover layer covering the flexible PCBA and attached to the flexible radiant energy bottom cover layer to encase the flexible PCBA and flexible PCBA cover.

In yet another embodiment, described is a radiant energy bandage assembly comprising a flexible PCBA (Printed Circuit Board Assembly) including a plurality of radiant lamps configured to provide radiant energy to a user treatment area; a flexible radiant energy bottom cover layer covering the flexible PCBA, the flexible radiant energy bottom cover layer including a plurality of radiant energy communication areas aligned with the flexible PCBA plurality of radiant lamps; a replaceable flexible conformable thermal conduction layer attached to the flexible radiant energy bottom cover layer, the replaceable flexible conformable thermal conduction layer including a plurality of radiant energy communication areas aligned with the flexible radiant energy bottom cover layer plurality of radiant energy communication areas to communicate the radiant energy exiting the flexible radiant energy bottom cover layer through the flexible conformable thermal conduction layer plurality of radiant energy communication areas to the user treatment area, and the flexible conformable thermal conduction layer including a top surface and a bottom surface, the top surface adapted to be removably attached by a user to cover the flexible radiant energy bottom cover layer and the bottom surface adapted to cover and conform to the user treatment area; a control pod docking interface operatively connected to the plurality of radiant lamps and configured to operatively connect a control pod to control the plurality of radiant lamps to provide a dosage of radiant energy to the user treatment area; and a flexible top cover layer covering the flexible PCBA and attached to the flexible radiant energy bottom cover layer to encase the flexible PCBA and flexible PCBA cover.

In still another embodiment of this disclosure, described is a radiant energy bandage assembly comprising a flexible PCBA (Printed Circuit Board Assembly) including a plurality of radiant lamps configured to provide radiant energy to a user treatment area; a flexible radiant energy bottom cover layer covering the flexible PCBA, the flexible radiant energy bottom cover layer including a plurality of radiant energy communication areas aligned with the flexible PCBA plurality of radiant lamps; a replaceable flexible conformable thermal conduction layer attached to the flexible radiant energy bottom cover layer, the replaceable flexible conformable thermal conduction layer including a plurality of radiant energy communication areas aligned with the flexible radiant energy bottom cover layer plurality of radiant energy communication areas to communicate the radiant energy exiting the flexible radiant energy bottom cover layer through the flexible conformable thermal conduction layer plurality of radiant energy communication areas to the user treatment area, and the flexible conformable thermal conduction layer including a top surface and a bottom surface, the top surface adapted to be removably attached by a user to cover the flexible radiant energy bottom cover layer and the bottom surface adapted to cover and conform to the user treatment area; a controller operatively connected to the plurality of radiant lamps and configured to operatively control the plurality of radiant lamps to provide a dosage of radiant energy to the user treatment area; and a flexible top cover layer covering the flexible PCBA and attached to the flexible radiant energy bottom cover layer to encase the flexible PCBA and flexible PCBA cover.

In another embodiment, described is a radiant energy bandage thermal conductive gel layer operatively arranged and configured with a radiant energy bandage assembly including a plurality of radiant lamps, the radiant energy bandage thermal conductive gel layer comprising a flexible conformable thermal conduction layer including a plurality of radiant energy communication areas positioned to align with the plurality of radiant lamps to communicate radiant energy from the plurality of radiant lamps through the flexible conformable thermal conduction layer to a user treatment area, the flexible thermal conduction layer including a top surface and a bottom surface, the top surface adapted to be removably attached to the operatively arranged and configured radiant energy bandage assembly and the bottom surface adapted to cover and conform to the user treatment area.

BRIEF DESCRIPTION OF THE DRAWINGS

FIGS. 3A and 3B are perspective views of the radiant energy back bandage pad assembly shown in FIGS. 1A, 1B and 2, without the replaceable adhesive gel layer, according to an exemplary embodiment of this disclosure.

FIG. 4 is an exploded assembly view of the radiant energy back bandage pad assembly which is subsequently welded and cut-to-shape to provide the radiant energy back bandage pad assembly shown in FIGS. 3A and 3B, without the replaceable adhesive gel layer, according to an exemplary embodiment of this disclosure.

FIGS. 6A, 6B and 6C include a top view, side view and bottom view, respectively, of the radiant energy back bandage pad assembly shown in FIGS. 5A, 5B and 5C, after the bandage pad assembly is cut-to-shape, according to an exemplary embodiment of this disclosure.

FIGS. 19A and 19B are top views and FIGS. 19C and 19D are front views of a first portion and second portion of an adhesive gel refill which attach to the bottom layer of a radiant energy back bandage pad assembly, according to an exemplary embodiment of this disclosure.

FIG. 30 is a perspective view of a radiant energy knee bandage pad assembly adhesive gel refill assembly, according to an exemplary embodiment of this disclosure.

FIG. 31 is an exploded view of the radiant energy knee bandage pad assembly adhesive gel refill assembly shown in FIG. 30.

FIG. 32 is a top view of the radiant energy knee bandage pad assembly adhesive gel refill assembly shown in FIG. 30.

FIGS. 43A-43E are schematics of a radiant energy controller pod, according to an exemplary embodiment of this disclosure.

FIG. 50A is representative of the controller pod-side bandage pad connector; FIG. 50B is representative of a first orientation of the back/knee bandage pad control pod connector; FIG. 50C is an electrical connection state diagram associated with the first orientation of the back/knee pad control pod connector interconnected to the controller pod connector; FIG. 50D is representative of a second orientation, rotated 180 degrees relative to the first orientation, of the back/knee bandage pad control pod connector; and FIG. 50E is an electrical connection state diagram associated with the second orientation of the back/knee pad control pod connector rotated 180 degrees and interconnected to the controller pod connector.

FIGS. 59A, 59B, 59C and 59D include a top view, bottom view, side view and end view, respectively, of the radiant energy back bandage assembly including an operatively connected control pod shown in FIG. 58.

FIGS. 65A, 65B, 65C and 65D include a top view, bottom view, side view and end view, respectively, of the knee bandage pad assembly shown in FIG. 64.

DETAILED DESCRIPTION

Figure 1A:
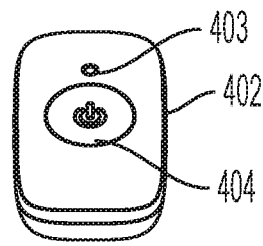
FIGS. 1A, 1B and 1C are perspective views of a radiant energy back bandage pad assembly including a replaceable adhesive gel layer, according to an exemplary embodiment of this disclosure.

This disclosure, and the exemplary embodiments described herein, relate to a radiant energy bandage to be applied to a user treatment area such as, but not limited to a person's back, lumbar, shoulder area, arms, legs, knees, etc. According to the exemplary embodiments described, the radiant energy provided by the bandage is Red and IR (infrared) wavelength radiant energy, however other wavelengths of radiant energy delivery are within the scope of this disclosure.

As described in "Light Therapy Bandage System", U.S. Patent Publication No. US 2014/0277298, by Tapper et al., ('298) and "Light Therapy Bandage System", U.S. Patent Publication No. US 2015/0290470, by Tapper et al., ('470) the basic operation of the presently disclosed radiant energy bandage includes a bandage type structure which includes a plurality of Red/IR LEDs emitting radiation energy through a plurality of intermediate layer apertures through a second set of apertures which are part of a user attachable/removable conformable gel layer, i.e., the conformable gel layer is "refillable". The radiant energy emitted from a bottom surface or exposed surface of the gel layer is directed to the user treatment area. Furthermore, the exposed surface of the applied conformable gel layer is placed on the surface of the user treatment area to maintain a removable adhesion of the radiant energy bandage to the user treatment area. A controller is operatively connected to the bandage type structure and controls the plurality of Red/IR LEDs to provide a dosage amount of radiant energy to the user treatment area.

The present disclosure and exemplary embodiments described herein provide other novel radiant energy bandage structures and method of constructing radiant energy bandage structures. Specifically described herein is a radiant energy back bandage pad assembly, a radiant energy knee bandage pad assembly and a control pod configured to control and power the back bandage pad assembly and knee bandage pad assembly. Similar to the '298 and '470 radiant energy bandages, the presently disclosed bandage structures use a conformable gel layer which is applied to the bandage by a user, where the conformable gel layer and attached bandage are then applied to the user treatment area, such as but not limited to a person's back or knee.

Some distinguishing and novel features of the disclosed radiant energy bandage exemplary embodiments include:

(1) a flexible and conformable shape of the back bandage pad to optimally position the Red/IR LEDs extremely close to the user treatment area to provide efficient radiant/optical energy transmission to the target tissue which may be as much as 20 mm below the user's skin;

(2) a "butterfly" shape of the knee bandage which includes four lobes that provide flexibility and conformability of the knee bandage to guide the Red/IR radiant energy to the tendons around the knee for optimal collagen production and inflammation reduction while avoiding the patella. The multiple lobe bandage design optimally positions the Red/IR LEDs extremely close to the user treatment area to provide efficient radiant/optical energy transmission to the knee area, where the target tissue may be as much as 5 mm or more below the skin of the knee;

(3) a radiant energy bandage pad construction and method of construction which includes a spot welded, perimeter welded and perimeter cut process to encase a flexible PCBA (Printed Circuit Board Assembly) and flexible bandage pad between a flexible bottom layer and flexible radiant energy transparent layer, thereby sealing the flexible PCBA, including the radiant energy LEDs and flexible pad from the external environment and protecting the user/user treatment area from any physical contact with the radiant energy LEDs and associated circuitry;

(4) a magnetic control pod docking/connection arrangement provides a manner of attaching a rigid structure, such as but not limited to a controller or a battery, to a flexible pad assembly such as a radiant energy bandage pad as described herein. In addition to the mating of opposite polarity magnets associated with a bandage pad assembly/control pod interface, electrical spring contacts provide an electrical contact arrangement which can maintain an electrical connection during flexing of the bandage pad assembly; and (5) a bandage pad/control pod interface configuration provides the ability for the control pod to mate with the bandage pad in two distinct different orientations and consistently deliver the required control and power to operate the bandage pad. Specifically, after a bandage pad/control pod radiant energy connection in either orientation, the control pod polls two dual functioning connections associated with the control pod which are connected to the bandage pad. The results of the poll determine the configuration of the dual functioning connections assigned by the pod controller. In other words, the dual function connections of the control pod are "hot-assigned". A symmetrical and dual power/ground contact arrangement provides "reverse polarity" tolerance of the bandage pad/control pod connection orientations.

Some additional distinguishing and novel features of the disclosed radiant energy bandage exemplary embodiments include:

(6) a conformable hydrogel layer adhesive and bandage design which conducts heat generated by radiant energy LEDs to a user treatment area surface in an efficient manner, whereby the gel layer is a homogenous hydrogel with a thermal conductivity much greater than the user treatment area, and the hydrogel layer adheres and conforms to the user treatment area with a zero-air-gap; and (7) a conformable hydrogel layer adhesive and bandage design which efficiently retains heat within a hydrogel layer prior to conduction to the user treatment area utilizing a foam insulating layer located above the hydrogel layer, the user treatment located below the hydrogel layer.

As will be further described below with reference to the drawings, disclosed herein is a radiant energy bandage and assembly structure including a user attachable/removable hydrogel for user placement on a user treatment area to provide light radiation therapy and heat to the user treatment area for relieving pain and/or providing healing treatment. While not limited to a specific wavelength of radiant energy, the overall structure of the light therapy bandage provides an efficient transfer of IR/R (Infrared/Red) radiant energy to a user treatment area and an efficient conduction of heat from the light therapy bandage to the user treatment area. The structure of the disclosed light therapy bandage, according an exemplary embodiment, which can include body profiles such as a back, hip and knee bandage as further described below, includes a PVC encapsulated flexible PCBA with fixed IR/R LEDs which are controlled by an operatively connected controller to provide a dosage of radiant energy to the user treatment area. Furthermore, heat generated by the LEDs is also conductively transferred through the hydrogel later removably attached to the bandage to the user treatment area. The use of the hydrogel provides effectively a no-air-gap or sealed interface between the gel and the user treatment area, and effectively a non-air gap or sealed interface between the light therapy bandage device and the hydrogel layer, thereby providing efficient heat transfer. According to an exemplary embodiment, an IXPE (Irradiated Crosslinked Polyethylene) foam insulating layer is also encapsulated within the light therapy bandage thereby sandwiching the flexible PCBA between the foam layer and the hydrogel. The IXPE foam insulating layer provides for an efficient retention of heat generated by the LEDs within the gel layer, which is then conducted through the gel layer to the user treatment surface. The user of a conductive hydrogel enables heat to conduct both laterally and orthogonally within the gel layer, relative to the user treatment surface.

According to one exemplary embodiment, the gel layer is a clear hydrogel with apertures aligned with the LEDs to transmit or communicate IR/R radiation to the user treatment area. In this embodiment, the IR/R radiation is also radiated to the gel layer through the apertures to the gel layer and then laterally and orthogonally conducted through the gel layer as heat to the user treatment surface. In addition, waste energy generated by the LEDs is conducted by the gel layer to the user treatment surface. The thermal mass of the gel layer also provides for the storage of heat within the radiant energy bandage which contributes to the achieving and maintaining of elevated temperatures on the user treatment site as the user's skin is constantly acting to regulate the temperature of the user's body. The thermal mass of the gel enables the radiant energy bandage device to operate efficiently without the need for additional heat sources or higher energy consumption for a given amount of heat output.

In addition to the structure and operation of the radiant energy bandage device, as explained above, other structure features of the devices provide for an integrated and comprehensive structure to deliver radiant energy from the device to the user treatment area, such as but not limited to, a matte white printed surface on the bottom of the device which has a surface energy greater than the gel layer adhesive surface and the user treatment area surface, thereby enabling the gel layer to properly adhere to the device, and not the user treatment area surface, when the device is removed from the user treatment site. This feature enables the device and attached gel layer to be reused at another time. According to one exemplary embodiment, the surface energy of the matter white printed surface is greater than or equal to 30 dynes. In addition to providing an adhesive surface for the gel layer, according to one exemplary embodiment, this bottom layer or surface of the device is made of a clear PVC which is matte printed in a masked fashion to provide windows through the clear PVC to communicate or transmit the radiant energy from the LEDs through the apertures of the gel layer to the user treatment area. A gradient fade of the matte white printing to generate the window provides improved aesthetics of the device. The matte white printed surface also provides a diffuse (Lambertian) reflection of radiant energy reflected from the user treatment area through the gel layer, this diffuse reflection providing spreading of the diffused reflected IR/R radiant energy throughout the gel layer, without excessive lightbleed through the other components of the device.

Additional features of an exemplary embodiment of the gel layer are directed to the integration of function and ease of use, including the use of a multilayered gel layer which includes a transparent scrim type substrate sandwiched between a top and bottom hydrogel layer, the scrim extending beyond the border of the gel layer at one or more sides, thereby providing a dry tab surface to enable a user to remove the gel layer from the bandage device. The locations of the scrim, relative to the top gel layer and bottom layer, is determined based on the overall profile of the bandage device and associated gel layer. In other words, some profiles, such as a knee bandage profile further described below, necessitate a 60:40 set at the scrim, indicating 60% of the gel weight reaches up the bottom or skin contacting side of the gel. Other profiles, such as a back or hip bandage profile as further described below, necessitate a 50:50 set of the scrim.

With regard to the packaging of the gel layer, the disclosed exemplary embodiments incorporate an integrated structure to provide packaging and applications of the gel layer to the radiant energy bandage. According to an exemplary embodiment, a gel layer carrier includes two symmetrical gel pads removably attached to a backer liner, such as a clear PST backer card which has a siliconized release system on both sides. The gel layers are covered with an opaque siliconized PE upper release liners on the device application side, which are discarded by the user after application of the gel onto the device. The upper release liners include a middle and top portions which create a tabbed surface for removal of the open liners from the gel. To apply the gels to the device, the user removes the upper liners and then locates the gel layers on the device to align the apertures of the gel layers with the appropriate radiant windows on the bottom of the radiant energy bandage device. The clear backer line provides a visual indication of the gel layers locations relative to the window and the clear backer liner is perforated to enable attachment of each gel layer portion separately. After use of the device, a user places the backer liners on the gel layers, which remain attached to the device, for storage until the next time the device is used, when the backer will be removed.

According to an exemplary embodiment of this disclosure, a usable paper-foil laminate pouch provides packaging and storage of the gel layers, and also is sized to store the radiant energy bandage with the gel layers and back liners attached thereto. According to an exemplary embodiment, the pouch is sized to store a folded bandage device with the gel layers and backer layers attached. The external paper surface of the pouch provides for printing of information, including manufacturer product codes, instructions for use of the device and/or application of the gel to the device, etc.

Provided below are further details of exemplary embodiments of a back bandage pad assembly, a knee bandage pad assembly, and a back/knee bandage control pod. It is to be understood that the exemplary embodiments described herein do not limit the scope of the novel and distinctive features provided. Specifically, the bandage pads disclosed can be used in many user treatment areas such as arms, elbows, feet, ankles, etc., and are not limited in their application to the back and knee.

Figure 1B:
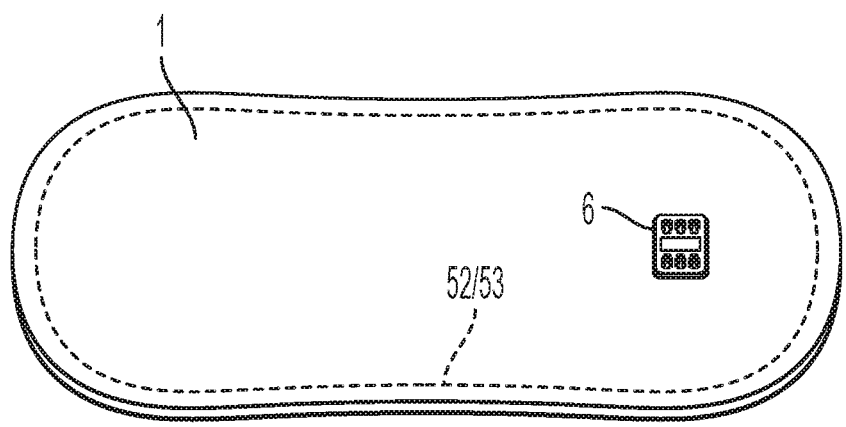
Figure 1C:
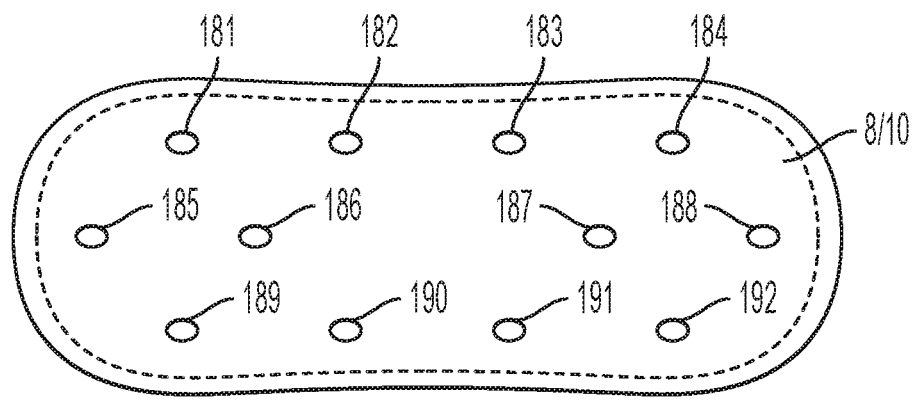

With reference to FIGS. 1A, 1B and 1C, illustrated are perspective views of a radiant energy back bandage pad assembly including a replaceable adhesive gel layer 8/10 according to an exemplary embodiment of this disclosure. As shown, the radiant energy back bandage includes a bandage pad assembly 1 including a plurality of radiant lamps and circuitry encased by a sonic or high frequency (HF) welded 52/53 top and bottom layer, a control pod 402 and an adhesive gel 8/10. The bandage pad assembly 1 includes a control pod interface 6 which is operatively connected to a control pod 402, which includes a user control switch 404 and an indicator LED 403 to indicate a state of the controller. The adhesive gel 8/10 includes a plurality of radiant energy communication areas 181-192 or apertures to allow transmission of a plurality of respective radiant energy lamps to a user treatment area with the radiant energy bandage applied to the user treatment area. During use, the external surface of the adhesive gel 8/10 conforms and adheres to the user treatment area and the user initiates a delivery of a dosage of radiant energy using the control pod switch 404.

Figure 2:
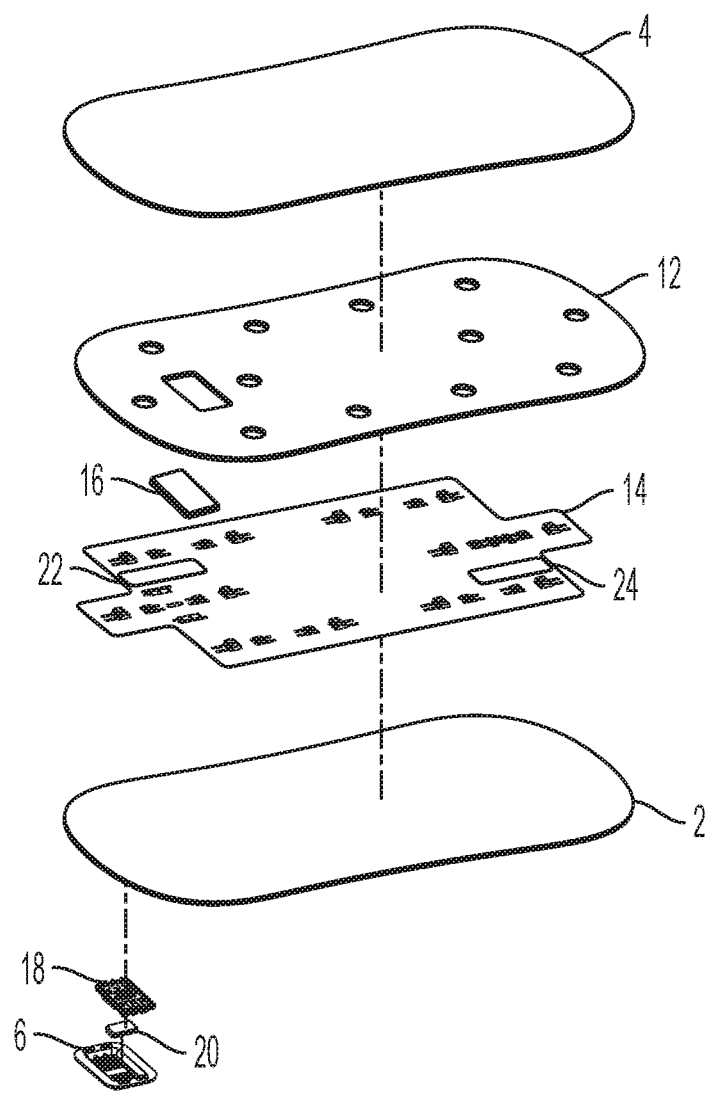
FIG. 2 is an exploded assembly view of the radiant energy back bandage pad assembly shown in FIGS. 1A and 1B, without the replaceable adhesive gel layer, according to an exemplary embodiment of this disclosure.

With reference to FIG. 2 illustrated is an exploded assembly view of the radiant energy back bandage pad assembly shown in FIGS. 1A and 1B, without the replaceable adhesive gel layer 8/10, according to an exemplary embodiment of this disclosure. As shown, the radiant energy back bandage pad assembly 1 includes a control pod interface 6, a control pod docking magnet 20, a control pod interface contact assembly 18, a top layer 2, a flexible PCBA (Printed Circuit Board Assembly) 14, adhesive tapes 22 and 24, a control pod interface base 16, a pad 12, and a transparent bottom layer 4. An adhesive gel layer 8/10 illustrated in FIG. 1C is applied to the bottom layer 4 of the bandage pad assembly 1, where the apertures of the adhesive gel layer 8/10 align with the pad 12 apertures of the bandage pad assembly 1. Radiant energy is generated by a plurality of Red/IR (Infrared) LEDs mounted to the flexible PCBA 14 and which are aligned with the apertures of the pad 12. According to an exemplary embodiment, adhesive strips 22 and 24 fix the pad 12 to the flexible PCBA 14. As will be further described with reference to FIG. 4, the pad 12 and flexible PCBA 14 are encased within top layer 2 and transparent bottom layer 4 providing a sandwich type construction. The control pod interface base 16 extends through the flexible PCBA 14 and top layer 4 to interconnect the control pod interlace contact assembly 18, control pod docking magnet 20 and control pod interface 6.

In addition to the Red/IR LEDs, the flexible PCBA 14 includes associated circuitry and components to drive the Red/IR LEDs, a temperature sensor configured to monitor the temperature of the bandage pad during operation, and an electrical connection interface which is operatively connected to the control pod interface contact assembly 18.

The control pod interface contact assembly 18 and control pod interface 6 establish a user attachable/detachable electrical/structural interlace with a control pod 402 which is configured to provide power and control of the back bandage pad assembly during operation.

With reference to FIGS. 3A and 3B, illustrated are perspective views of the radiant energy back bandage pad assembly shown in FIGS. 1A, 1B and 2, without the replaceable adhesive gel layer 8/10, according to an exemplary embodiment of this disclosure.

With reference to FIG. 4, illustrated is an exploded assembly view of a radiant energy back bandage pad assembly 1A which is subsequently welded and cut-to-shape to provide the radiant energy back bandage pad assembly 1 shown in FIGS. 3A and 3B, without the replaceable adhesive gel layer 8/10, according to an exemplary embodiment of this disclosure. As shown in FIG. 4, initially an over-sized top layer 2A and over-sized bottom layer 4A are provided and used to encase the pad 12 and flexible PCBA 14. Top layer locators/alignment holes 42, 44, 46, 48 and 50 mate with bottom layer locators/alignment holes 32, 34, 36, 38 and 40, respectively, to align and fix the top layer 2A and bottom layer 4A with the pad 12 and flexible PCBA 14 substantially centered and encased within the top layer 2A and bottom layer 4A.

Next, the top layer 2A and bottom layer 4A are sonically or high frequency welded at layer locators/alignment holes 32/42, 34/44, 36/46, 38/48 and 40/50 to attach the top layer 2A to the bottom layer 4A.

Next, the oversized top layer 2A and bottom layer 4A are perimeter welded substantially near and outside the perimeter of the pad 12/flexible PCBA 14. The perimeter weld further encases the pad 12 and flexible PCBA 14 and seals the pad 12 and flexible PCBA from the external environment.

Finally, the perimeter welded top layer 2A and bottom layer 4A are simultaneously cut substantially near and outside the perimeter weld to produce the final back bandage pad assembly 1 including top layer 2 and bottom layer 4 as shown in FIGS. 3A/3B.

Figure 5C:
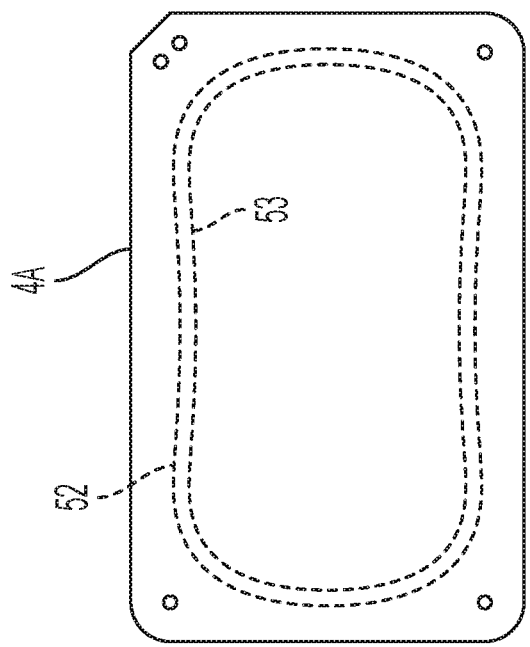
FIGS. 5A, 5B and 5C include a top view, side view and bottom view, respectively, of a radiant energy back bandage pad assembly including a sonic welded top layer and bottom layer prior to cutting-to-shape, according to an exemplary embodiment of this disclosure.
Figure 5B:
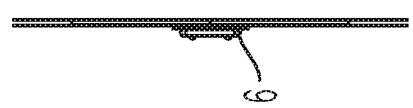
Figure 5A:
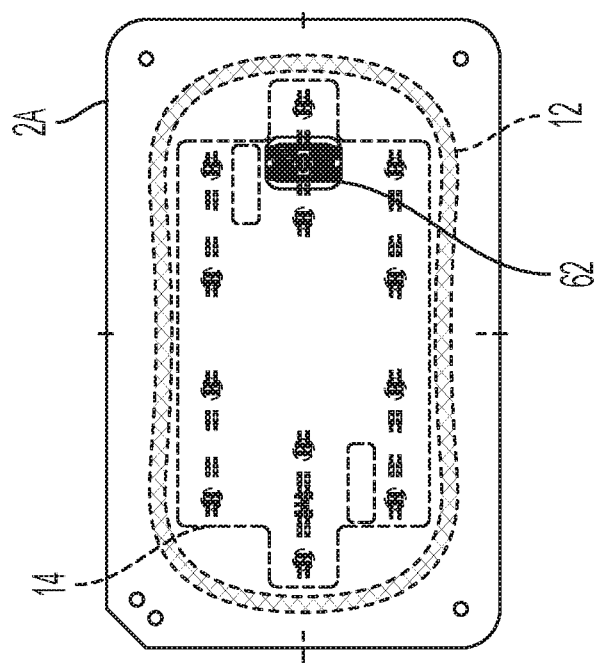

With reference to FIGS. 5A, 5B and 5C, illustrated are a top view, side view and bottom view, respectively, of a radiant energy back bandage pad assembly including a sonic or HF welded welded top layer and bottom layer prior to cutting-to-shape, according to an exemplary embodiment of this disclosure. The oversize top layer 2A is made of a flexible plastic sheet material, such as PVC (Polyvinyl Chloride), and includes a control pod interface clearance hole or window 62 enabling the control pod interface 6 to pass through the top layer 2A. The oversize bottom layer 4A is made of a radiant energy transparent/clear flexible plastic sheet material, such as PVC, and includes a smooth bottom surface after assembly by performing the perimeter sonic or HF welding process 52, 53 on the top layer 2A.

With reference to FIGS. 6A, 6B and 6C, illustrated are a top view, side view and bottom view, respectively, of the radiant energy back bandage pad assembly shown in FIGS. 5A, 5B and 5C including sonic/HF welds 52 and 53, after the bandage pad assembly is cut-to-shape, according to an exemplary embodiment of this disclosure. As shown, the bandage pad assembly 1A is perimeter cut 54 resulting in an encased bandage pad structure including a substantially rectangular shaped flexible top layer 2 and transparent flexible bottom layer 4. The final shape can also be described as being substantially rectangular with curved corners or substantially rectangular including a left lobe and right lobe, where the outside width $W_{LO}$ and $W_{RO}$ of the bandage pad assembly 1 is greater than the inside width $W_I$ of the bandage pad assembly 1 to provide flexibility and conformability of the bandage pad assembly 1 to a user treatment surface. FIG. 6C shows the relative locations of LED 1-LED 24 to the overall bandage pad assembly 1.

According to an exemplary embodiment of the bandage pad assembly 1, the overall length of the bandage pad is 180-230 mm and the overall width of the bandage pad is 80-130 mm, however, the bandage pad assembly can be of any size provided the number and placement of radiant energy lamps, i.e., LEDs 1-24, and the associated flexible PCBA are configured to provide radiant energy to the user treatment area covered by the bandage pad assembly and attached flexible conformable adhesive gel layer.

Figure 7:
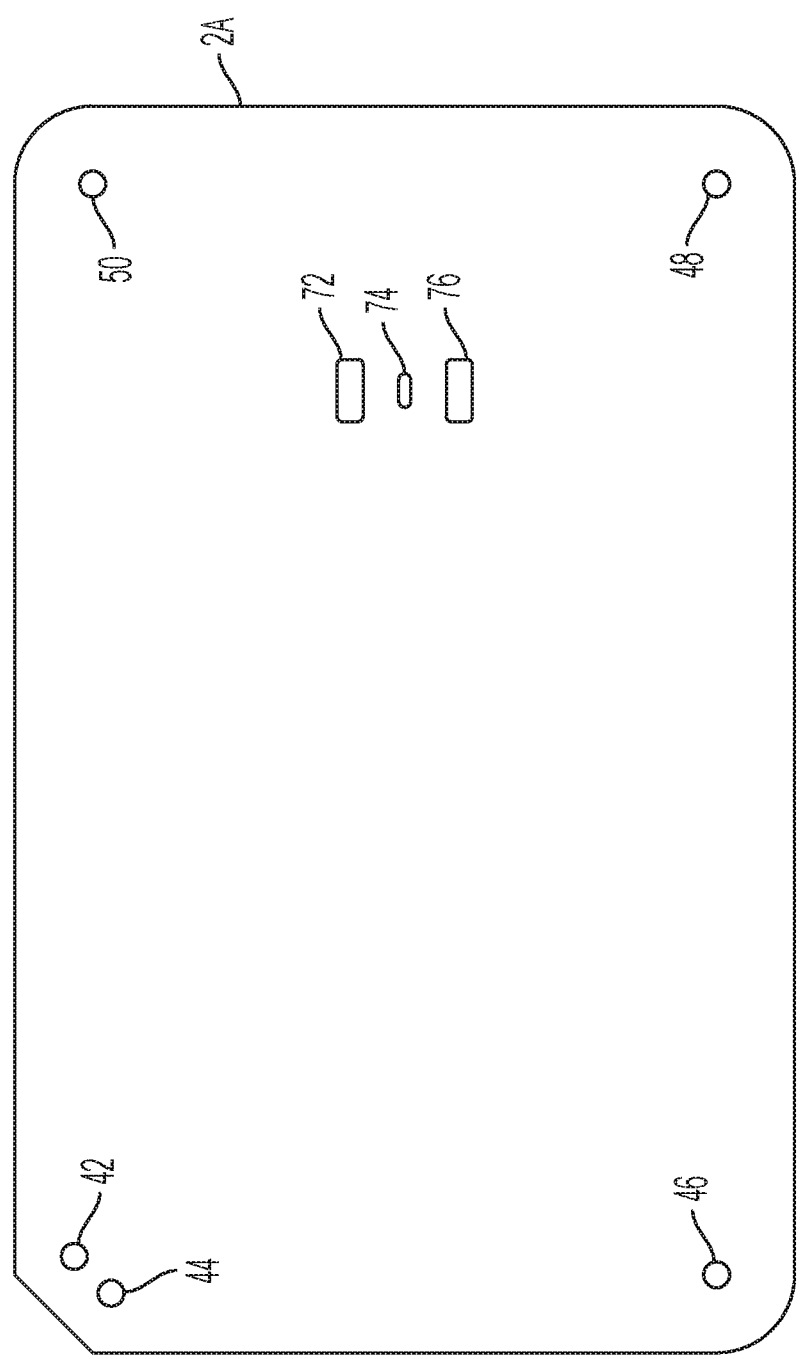
FIG. 7 is a top view of a radiant energy back bandage pad top layer, according to an exemplary embodiment of this disclosure.

With reference to FIG. 7, illustrated is a top view of a radiant energy back bandage pad oversize top layer, according to an exemplary embodiment of this disclosure. As shown, the oversize top layer 2A includes locator alignment holes 42, 44, 46, 48 and 50, which are used to mate with corresponding locator alignment holes of the oversize bottom layer 4A during assembly of the pad assembly and control pod interface clearance holes 72, 74 and 76.

Figure 8:
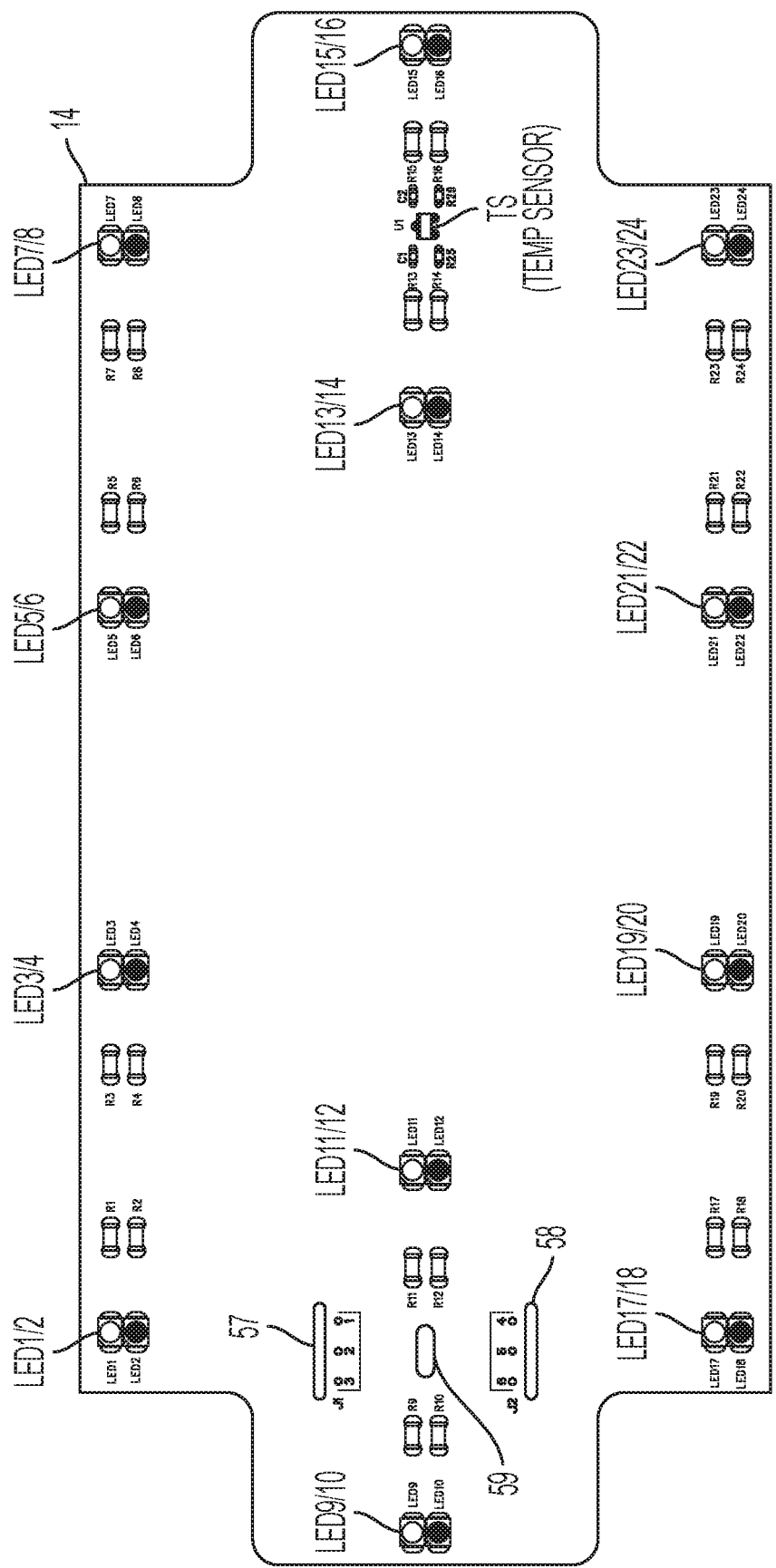
FIG. 8 is a bottom view of a radiant energy back bandage pad assembly flexible PCBA, according to an exemplary embodiment of this disclosure.

With reference to FIG. 8, illustrated is a bottom view of a radiant energy back bandage pad assembly flexible PCBA 14, according to an exemplary embodiment of this disclosure. The flexible PCBA 14 is made of a flexible PCBA substrate including conductive tracks and electrical component mounting holes/surfaces. The flexible PCBA 14 also includes control pod interface connection point blocks 57 and 58, each block providing three independent connection points/terminals to electrically connect to the control pod interface contact assembly 18 using electrical conductors/terminals. Feedthrough hole 59 is provided to extend the control pod interface base 16 from the bottom surface of the flexible PCBA 14 through the feedthrough hole 59 and top layer 2 to operatively attach the control pod interface contact assembly 18 to the bandage pad assembly 1.

LEDs 1-24 and temp sensor TS are mounted to the flexible PCBA 14 along with other associated components such as resistors/capacitors. Each pair of LEDs, i.e., LED 1/2, LED 3/4, LED 5/6, LED 7/8, LED 9/10, LED 11/12, LED 13/14, LED 15/16, LED 17/18, LED 19/20, LED 21/22 and LED 23/24, includes a Red wavelength radiant energy emitting LED and an IR wavelength radiant energy emitting LED. According to an exemplary embodiment, the Red LED specifications include a peak wavelength of 620-640 μm, peak power of >1000 uW and total power of >22.1 mW; the IR LEDs specifications include a peak wavelength of 820-880 μm, peak power of >400 uW and total power of 15.4 mW; and the temperature sensor TS is an analog temperature sensor outputting 10 mV/° C.

The overall shape and size of the flexible PCBA is relatively smaller than the top layer 2/2A and transparent bottom layer 4/4A to enable the flexible PCBA 14 to be encased within the top layer 2 and transparent bottom layer 4 after these layers are spot welded—perimeter welded—perimeter cut as previously described.

While the flexible PCBA 14 exemplary embodiment described includes Red/IR LEDs and an analog temperature sensor, other LEDs and temperature sensor types are within the scope of this disclosure. For example, LEDs which emit radiant energy at other wavelengths/power and other temperature sensors such as digital temperature sensors.

Figure 9:
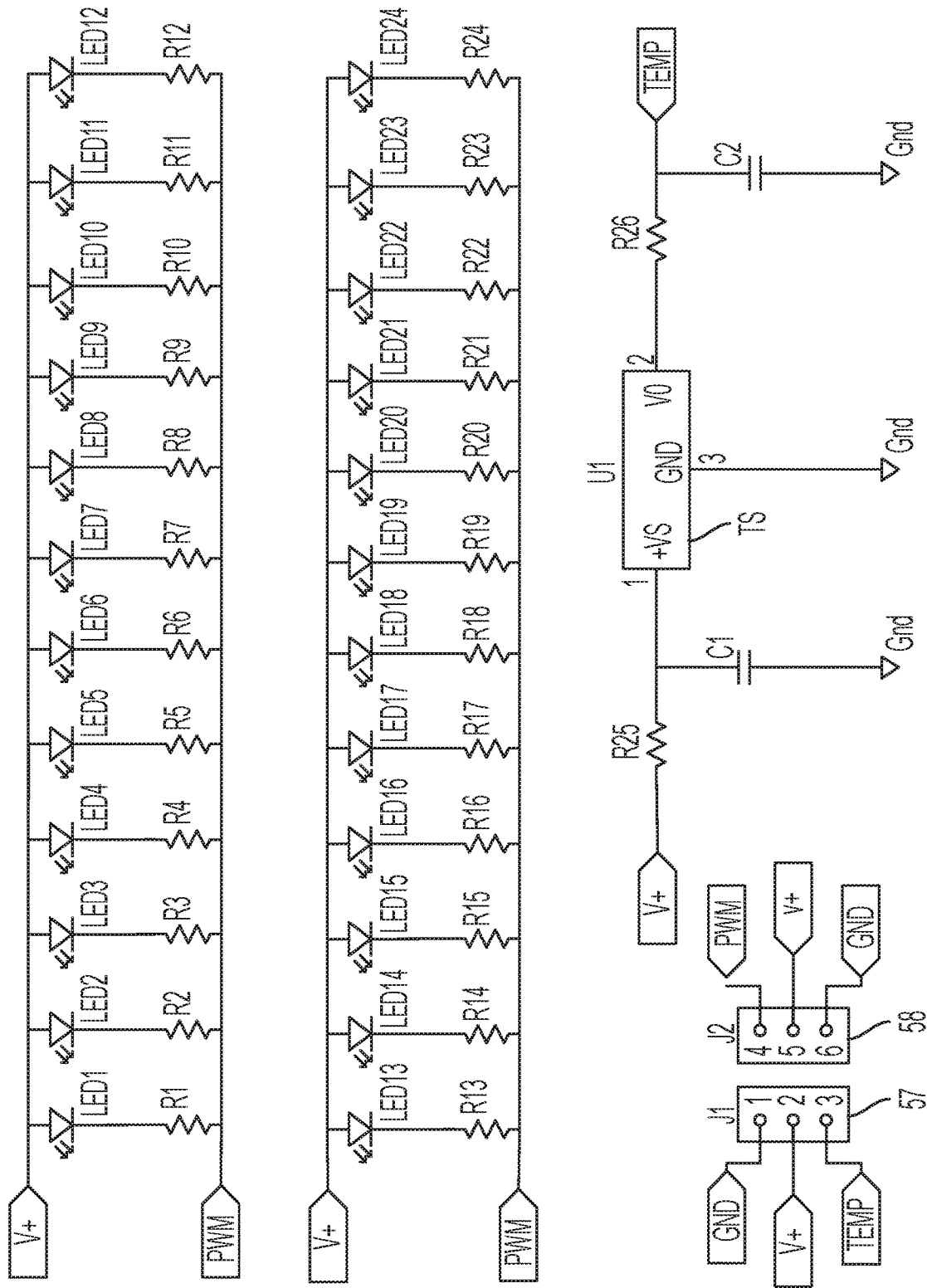
FIG. 9 is a schematic of the radiant energy back bandage pad flexible PCBA shown in FIG. 8.

With reference to FIG. 9, illustrated is an electrical schematic of the radiant energy back bandage pad flexible PCBA 14 shown in FIG. 8. As shown, a PWM (Pulse Width Modulated) signal is used to drive LEDs 1-24. Other electrical components include resistors R1-R6, capacitors C1 and C2, control pod interface connection point blocks J1 (57) and J2 (58), and analog temperature sensor U1 (TS). As will be further described below, a controller is operatively connected to connection point blocks J1 (57) and J2 (58) to power and control the LEDs to emit radiant energy to a user treatment area.

Figure 10:
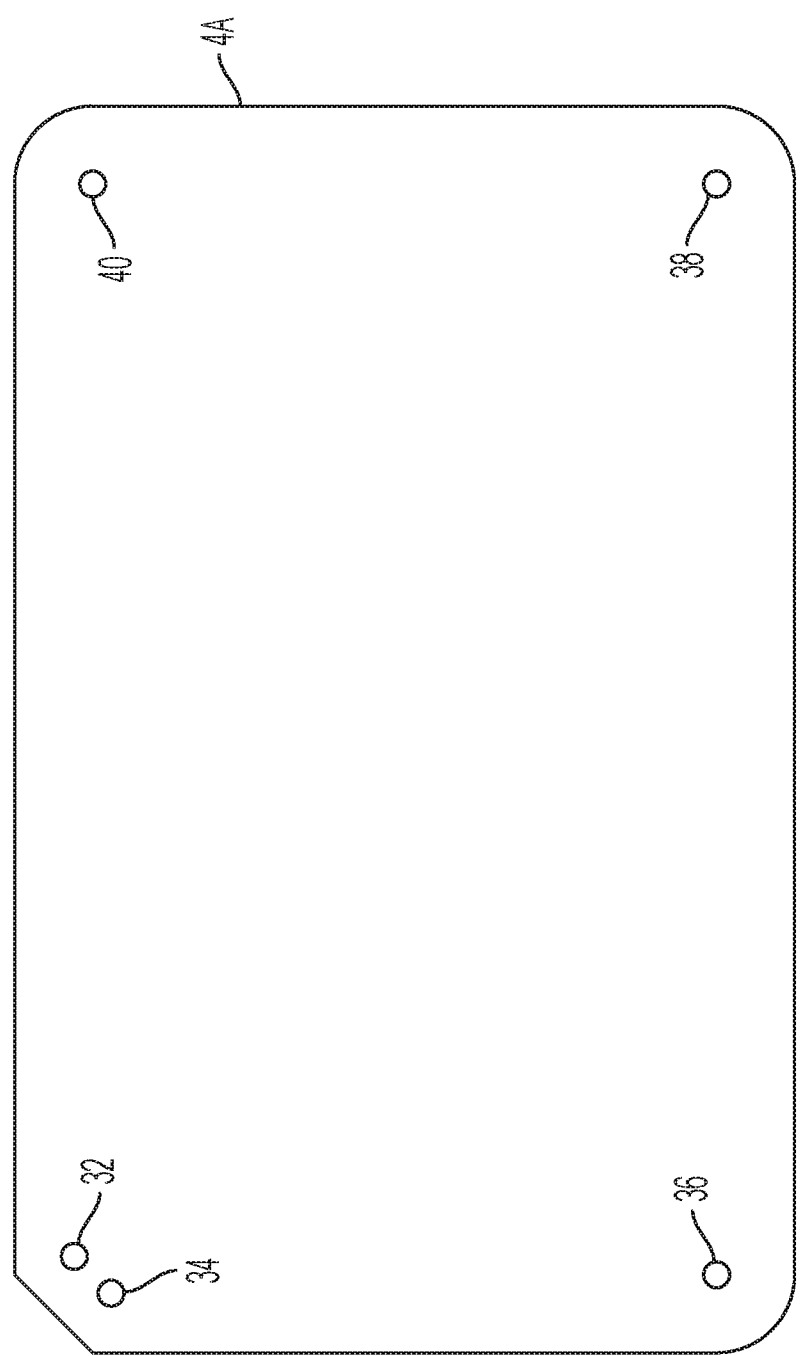
FIG. 10 shows a radiant energy back bandage pad assembly bottom layer, according to an exemplary embodiment of this disclosure.

With reference to FIG. 10, illustrated is a radiant energy back bandage pad assembly oversize bottom layer 4A including pad assembly locator/alignment holes 32, 34, 36, 38 and 40 which are mated with corresponding to top layer 2A locator alignment holes during assembly of the pad assembly 1, according to an exemplary embodiment of this disclosure.

Figure 11:
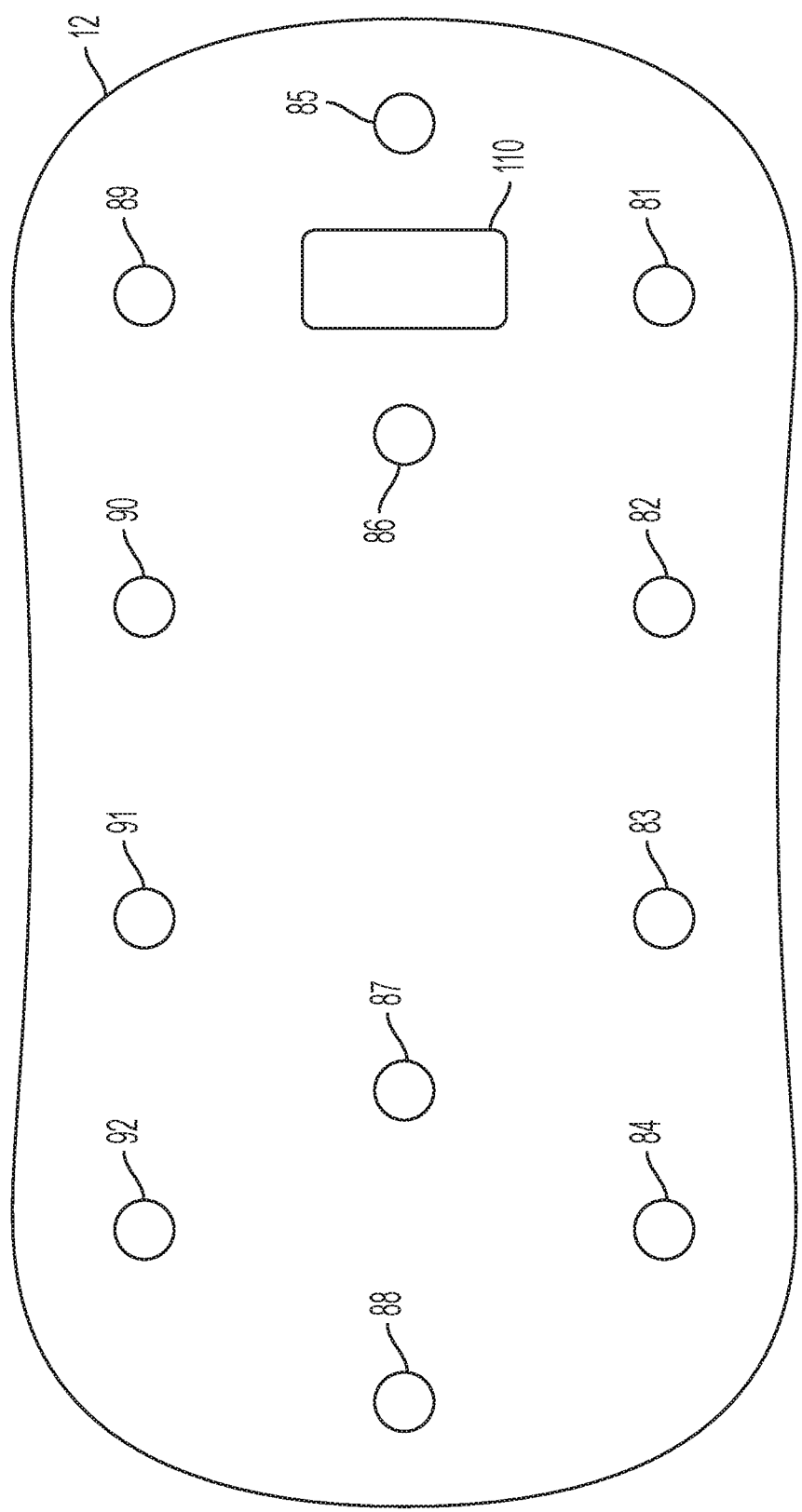
FIG. 11 shows a radiant energy back bandage pad, according to an exemplary embodiment of this disclosure.

With reference to FIG. 11, illustrated is a radiant energy back bandage pad, according to an exemplary embodiment of this disclosure. As shown, the radiant energy back bandage pad includes a plurality of apertures 81-92 which extend through the top surface of the bandage pad 12 and bottom surface of the bandage pad 12. The locations of the pad apertures 81-92 correspond and align with the locations of the flexible PCBA LEDs 1-24 such that the Red/IR wavelength energy emitted from LEDs 1-24 is guided through the bandage pad apertures 81-92, and then through the transparent bottom layer 4 and adhesive gel layer apertures 181-192. (FIG. 1C) A control pod interface clearance hole 110 provides structural clearance within the pad 12 to accommodate the control pod interface base 16.

According to an exemplary embodiment, the flexible bandage pad 12 is a multiple layer structure including a PE (Polyethylene) foam and a radiant energy reflective top surface made of mica which is oriented towards the flexible transparent top layer 2 and provides radiant energy reflective properties to reflect/contain radiant energy and heat between the reflective surface and the user treatment area with the bandage assembly applied to the user treatment area using an adhesive conformable gel layer 8/10.

According to another exemplary embodiment, the flexible bandage pad is a single layer of 5 mm to 20 mm thick PE foam or IXPE (Irradiated crosslinked polyethylene foam) with a very fine closed-cell structure. According to an exemplary embodiment, the foam pad 12 is a 1 mm thick IXPE foam pad.

Figure 12:
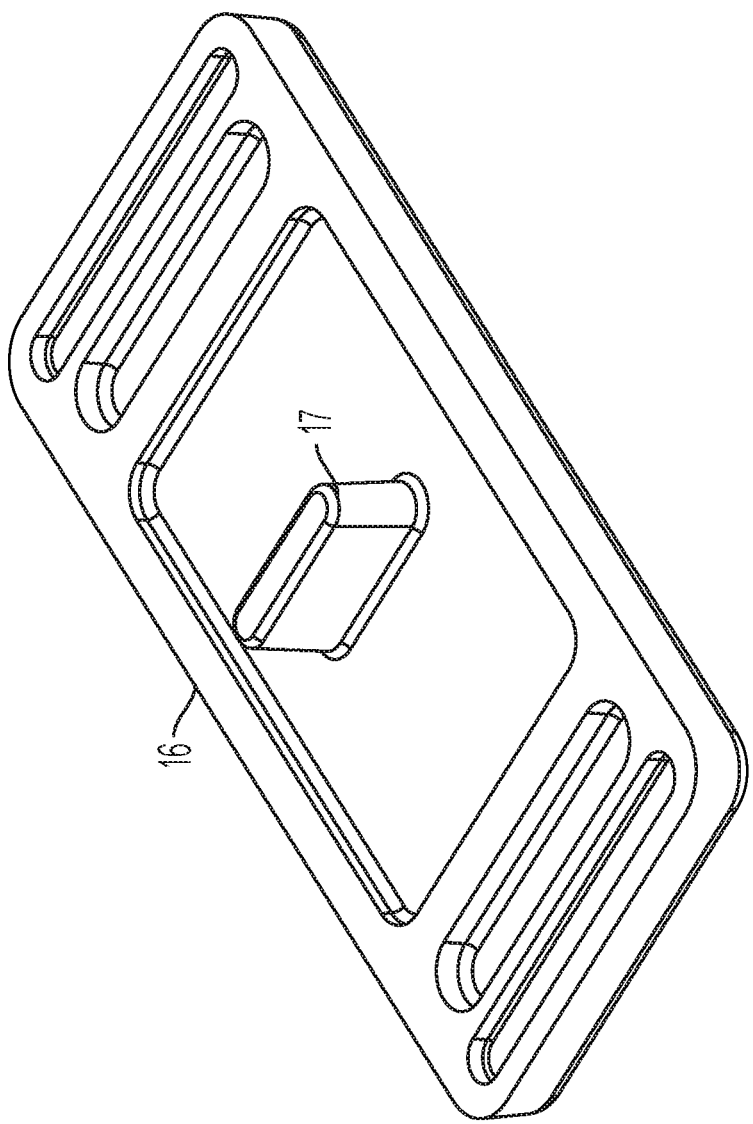
FIG. 12 is a perspective view of a pad/pod connection base plate, according to an exemplary embodiment of this disclosure.

With reference to FIG. 12, illustrated is a perspective view of a pad/pod connection base plate 16, according to an exemplary embodiment of this disclosure. As shown, and previously described, the base plate 16 includes a post/protruding member 17 that extends through the flexible PCBA 14 to mate with the control pod interface contact assembly 18. According to an exemplary embodiment, the pad/pod connection base plate is made of a plastic material.

Figure 13B:
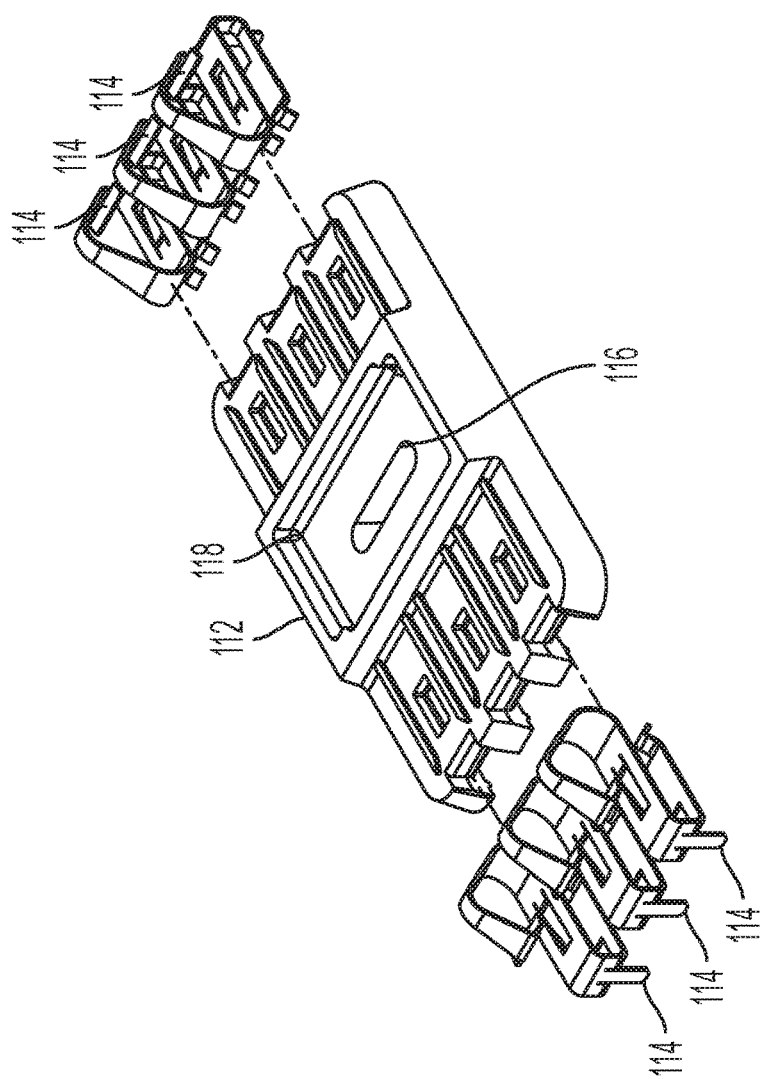
FIGS. 13A and 13B are perspective views of a control pod interface contact assembly, according to an exemplary embodiment of this disclosure.
Figure 13A:
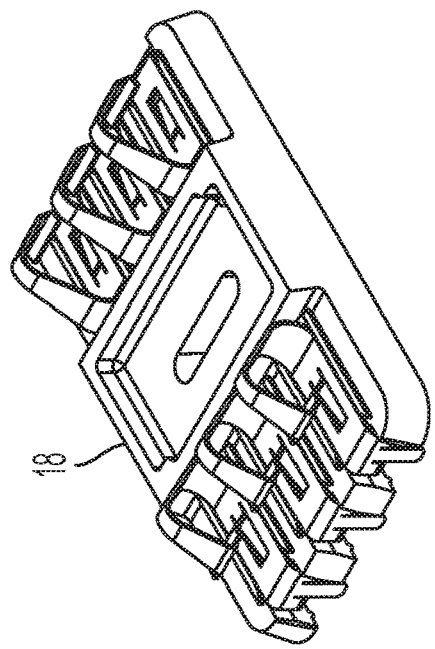

With reference to FIGS. 13A and 13B, illustrated are perspective views of a control pod interface contact assembly 18, according to an exemplary embodiment of this disclosure. As shown, the control pod interface contact assembly 18 includes a control pod support 112 and a plurality of spring contacts 114 attached to the control pod support 112. The spring contacts 114 are electrically connected to PCBA 14 connection point blocks 57/58. A feed through hole 116 receives the pad/pod connection base plate post 17 and a control pod docking magnet receiver 118 is configured to retain the control pod docking magnet 20, which is of a polarity opposite to a docking magnet retained by the control pod to enable an attractive docking force for docking/connecting the bandage pad assembly 1 to the control pod 402. According to an exemplary embodiment, the control pod support 112 is made of a plastic material and the spring contacts 114 are made of a conductive material such as copper, silver, gold and brass.

Figure 14:
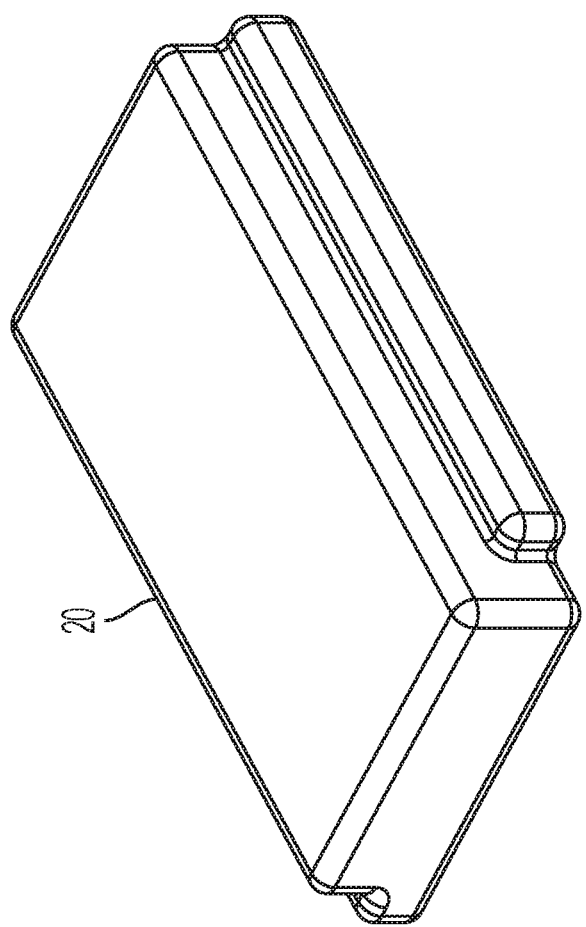
FIG. 14 is a perspective view of a back bandage pad assembly block magnet, according to an exemplary embodiment of this disclosure.

With reference to FIG. 14, illustrated is a perspective view of a back bandage pad assembly block magnet 20, according to an exemplary embodiment of this disclosure. As shown, the block magnet 20 includes protruding side members which are slidably engaged to receiver slots of the control pod magnet receiver 118 to retain the block magnet 20. According to an exemplary embodiment, the block magnet 20 is a sintered neodymium iron-boron (NdFeB) permanent magnet with a minimum 11.1N (2.5 Lb) pull force.

Figure 15A:
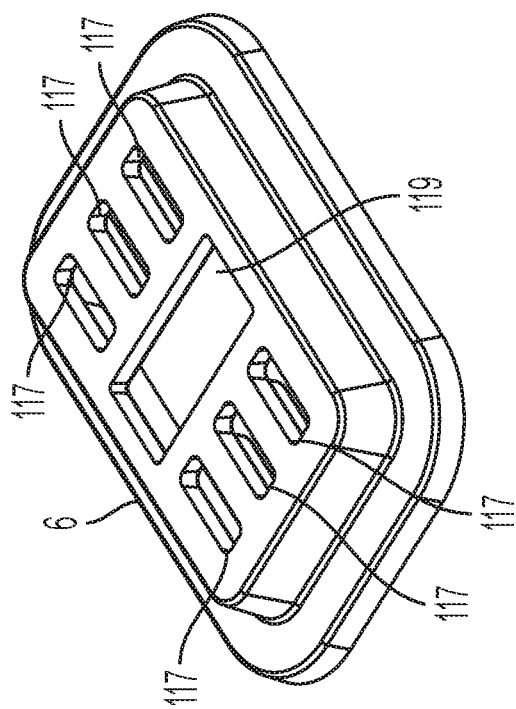
FIGS. 15A and 15B include a top perspective view and a bottom perspective view of a control pod interface upper housing, according to an exemplary embodiment of this disclosure.
Figure 15B:
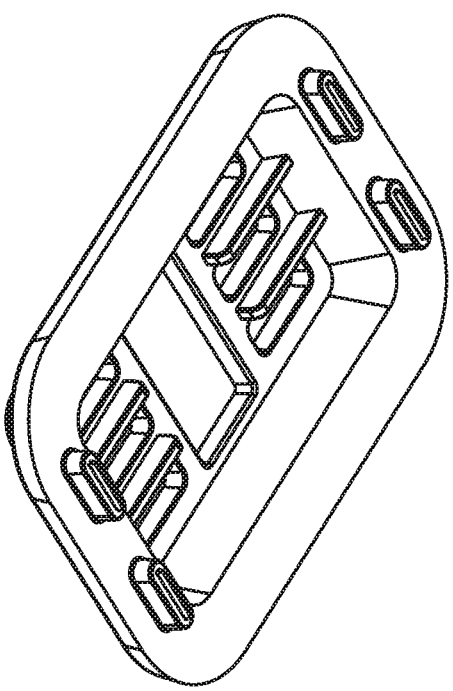

With reference to FIGS. 15A and 15B, illustrated are a top perspective view and a bottom perspective view of a control pod interface upper housing 6, according to an exemplary embodiment of this disclosure. As shown, the upper housing 6 includes a window 119 to expose the block magnet 20 for mating with the control pod magnet and the upper housing 6 includes a plurality of beveled feedthrough holes 117 to enable electrical connection of the spring contacts 114 to the control pod while protecting the spring contacts 114 with a control pod connected. According to an exemplary embodiment the control pod interface upper housing 6 is made of a plastic material.

Figure 18:
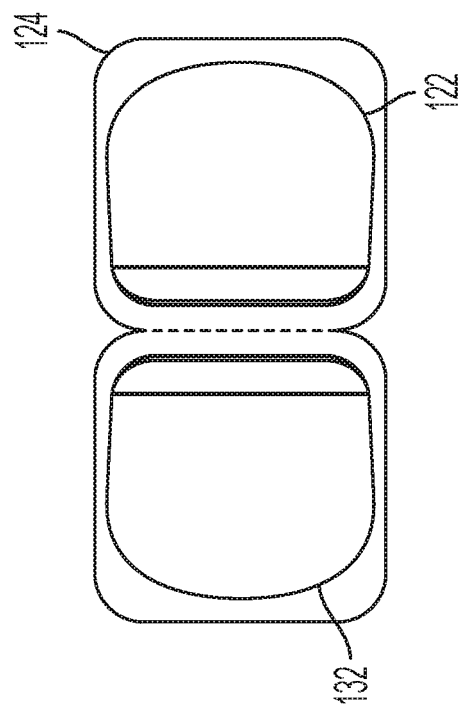
FIG. 18 is a top view of the radiant energy back bandage pad assembly adhesive gel refill assembly shown in FIG. 16.
Figure 16:
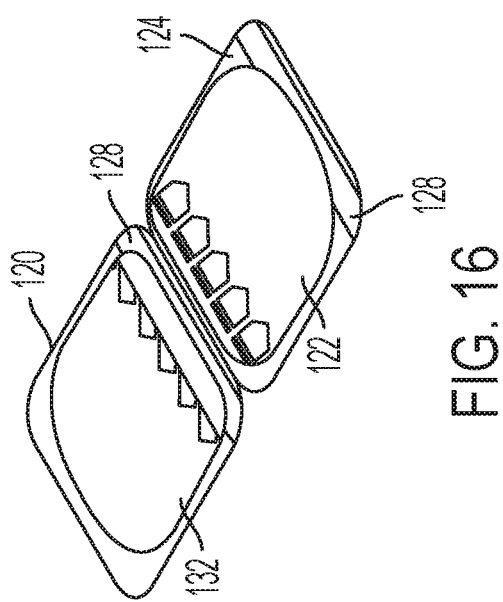
FIG. 16 is a perspective view of a radiant energy back bandage pad assembly adhesive gel refill assembly, according to an exemplary embodiment of this disclosure.
Figure 17:
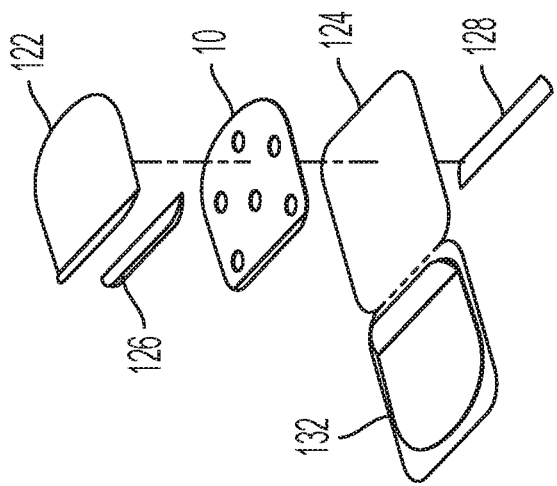
FIG. 17 is an exploded view of the radiant energy back bandage pad assembly adhesive gel refill assembly shown in FIG. 16.

With reference to FIGS. 16, 17 and 18, FIG. 16, illustrated, is a perspective view of a radiant energy back bandage pad assembly adhesive gel refill assembly, according to an exemplary embodiment of this disclosure, FIG. 17 is an exploded view of the radiant energy back bandage pad assembly adhesive gel refill assembly shown in FIG. 16; and FIG. 18 is a top view of the radiant energy back bandage pad assembly adhesive gel refill assembly shown in FIG. 16. The adhesive gel refill 120 includes a first adhesive gel layer 8 and a second adhesive gel layer 10 packaged in a foldable booklet type arrangement. The right side of the gel refill 120 includes a top liner 122, a middle liner 126, an adhesive gel layer 10, a backer 124 and a tape strip 128. The left side of the refill includes a top liner 132, a middle layer (not shown), an adhesive gel layer 8 (not shown), a backer (not shown) and a tape strip (not shown). The gel refill 120 is perforated between the first and second gel layers 8/10 to enable a user to separate each gel layer from the other, while keeping each gel layer on their respective backers for placement on the radiant energy back bandage bottom layer 4 for use.

With reference to FIGS. 19A and 19B, illustrated are top views of a first portion 8 and second portion 10 of an adhesive gel refill which attach to the bottom layer of a radiant energy back bandage pad assembly, according to an exemplary embodiment of this disclosure. As shown, each of the first and second portions of the adhesive gel refill includes a plurality of apertures. The first adhesive gel layer 8 includes apertures 181, 182, 185, 186, 189 and 190, and the second adhesive gel layer 10 includes apertures 183, 184, 187, 188, 191 and 192.

According to an exemplary embodiment, the adhesive gel layers 8 and 10 are made of a high tack double-sided reinforced hydrogel with a minimum thickness of 1.0 mm. The composition of the adhesive gel layers 8 and 10 provides a flexible conformable and heat conducting surface to apply the radiant energy bandage pad assembly to a user treatment area. The gel layer apertures 181-192 are aligned with the bandage pad apertures 81-92 to guide radiant energy from LEDs 1-24 to the user treatment area.

Furthermore, the conformable surface of the gel layers 8 and 10 adheres to the radiant energy bandage pad bottom layer 4 and the user treatment area to provide zero-air-gap heat conduction interfaces to efficiently transfer heat generated from the LEDs through the gel layers to the user treatment area. According to an exemplary embodiment of this disclosure, the gel layers are made of a clear transparent homogeneous hydrogel with a thermal conductivity of approximately 0.59 W/m-K (Watts per meter-Kelvin), such as is available from First Water, a Scapa® Healthcare Company, as Product Adhesive Gel Back Bandage.

With reference to FIGS. 19C and 19D, illustrated are front views of an adhesive gel first portion 8 and second portion 10 according to another exemplary embodiment of this disclosure. As shown, the adhesive gel layers include a multiple layer composition including top layers of a clear 8A/10A, bottom layers of the clear hydrogel 8B/10B and a middle transparent substrate 9/11 sandwiched between the top and bottom hydro gel layers. According to an exemplary embodiment, the middle transparent substrate is a non-woven polyester scrim which extends beyond one side of each hydro gel portion to create a dry, non-sticky user handling tab for removing of the adhesive adhesive gel layers 8/10 from the radiant energy back bandage assembly 1. According to an exemplary embodiment, the middle substrates are set at 50:50, where the middle substrate is located with equal amounts of the gel layer on the top and bottom of the middle substrate, where the thickness $T_{GLT}$ of the top clear hydrogel layers 8A/10A is approximately equivalent to the thickness $T_{GLB}$ of the bottom clear hydrogel layers 8B/10B while the exemplary embodiment described includes a 50:50 set of the middle substrate, also referred to a scrim, other sets are within the scope of this disclosure, for example a set of 55:45, 60:40, 65:35, etc. The set of the scrim can be selected depending on the desired adhesive and conformably performance of the adhesive gel layers to the user treatment surface, as well as the desired ease of removability of the adhesive gel layers from the radiant energy bandage assembly bottom layer or gel/bandage interface.

Figure 20A:
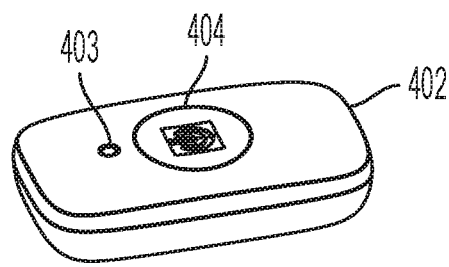
FIGS. 20A, 20B and 20C are perspective views of a radiant energy knee bandage pad assembly including a replaceable adhesive gel layer, according to an exemplary embodiment of this disclosure.
Figure 20B:
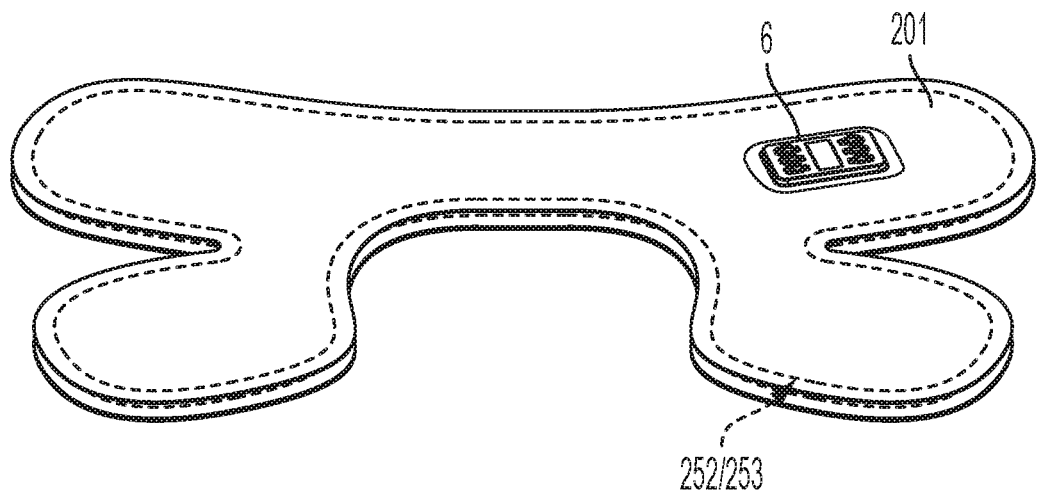
Figure 20C:
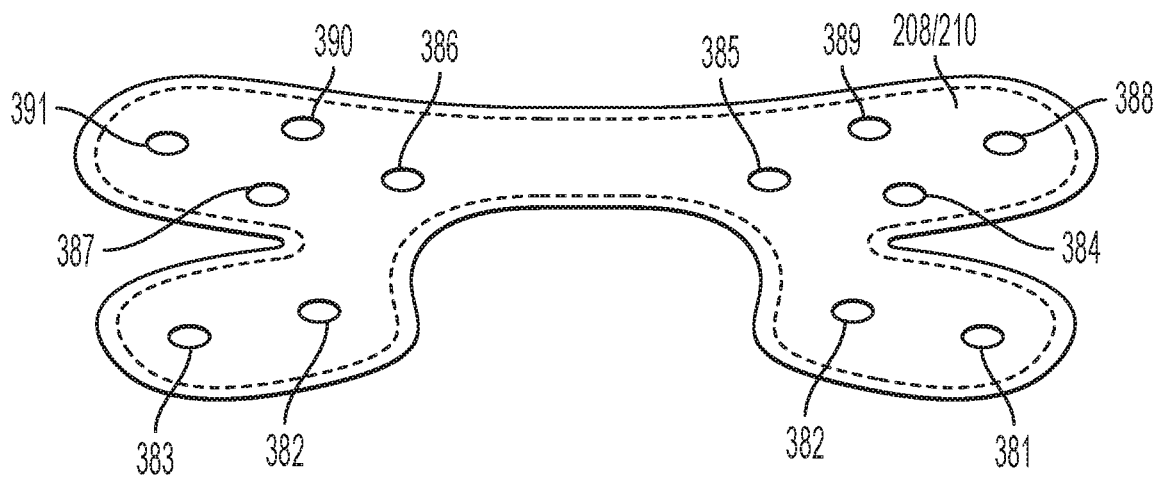

With reference to FIGS. 20A, 20B and 20C, illustrated are perspective views of a radiant energy knee bandage pad assembly 201 including a replaceable adhesive gel layer 208/210, according to an exemplary embodiment of this disclosure. As shown, the radiant energy knee bandage includes a bandage pad assembly including a plurality of radiant lamps and circuitry encased by a sonic or HF welded 252/253 top and bottom layer, a control pod 402 and an adhesive gel 208/210. The bandage pad assembly 201 includes a control pod interface 6 which is operatively connected to a control pod 402, which includes a user control switch 404 and an indicator LED 403 to indicate a state of the controller. The adhesive gel 208/210 includes a plurality of radiant energy communication areas 381-392 or apertures to allow transmission of a plurality of respective radiant energy lamps to a user treatment area with the radiant energy bandage applied to the user treatment area. During use, the external surface of the adhesive gel 208/210 conforms and adheres to the user treatment area and the user initiates a delivery of a dosage of radiant energy using the control pod switch 404.

Figure 21:
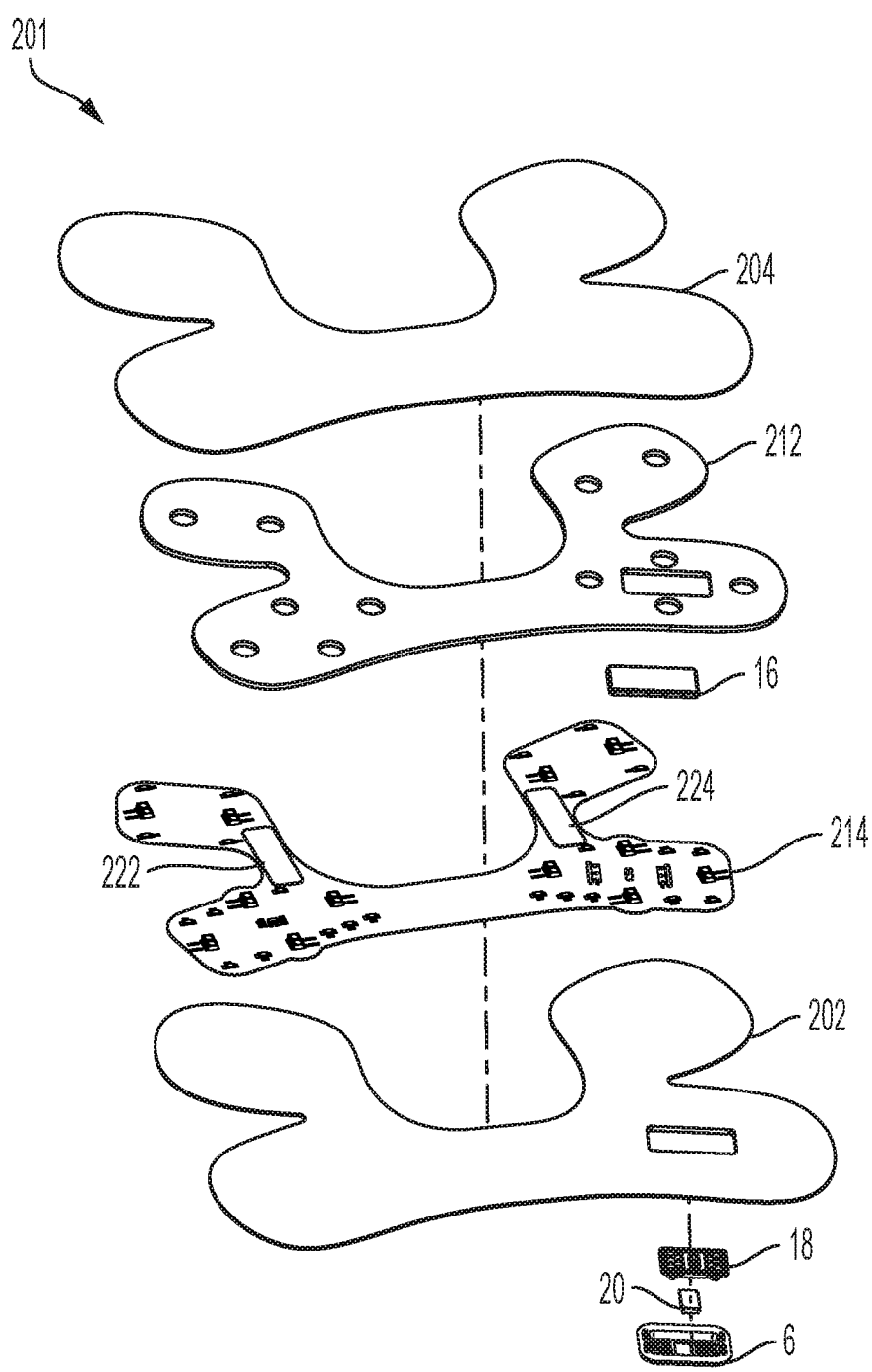
FIG. 21 is an exploded assembly view of the radiant energy knee bandage pad assembly shown in FIGS. 20A and 20B, including a replaceable adhesive gel layer, according to an exemplary embodiment of this disclosure.

With reference to FIG. 21, illustrated is an exploded assembly view of the radiant energy knee bandage pad assembly shown in FIGS. 20A and 20B, without a replaceable adhesive gel layer 208/210 according to an exemplary embodiment of this disclosure. As shown, the radiant energy knee bandage pad assembly 201 includes a control pod interface 6, a control pod docking magnet 20, a control pod interface contact assembly 18, a top layer 202, a flexible PCBA (Printed Circuit Board Assembly) 214, adhesive tapes 222 and 224, a control pod interface base 16, a pad 212, and a transparent bottom layer 204. An adhesive gel layer 208/210 illustrated in FIG. 20C is applied to the bottom layer 204 of the bandage pad assembly 201, where the apertures of the adhesive gel layer 208/210 align with the reflective pad 212 apertures of the bandage pad assembly 201. Radiant energy is generated by a plurality of Red/IR (Infrared) LEDs mounted to the flexible PCBA 214 which are aligned with the apertures of the pad 212. According to an exemplary embodiment, adhesive strips 222 and 224 fix the pad 212 to the flexible PCBA 214. As will be further described with reference to FIG. 23, the pad 212 and flexible PCBA 214 are encased within top layer 202 and transparent bottom layer 204 providing a sandwich type construction. The control pod interface base 16 extends through the flexible PCBA 214 and top layer 204 to interconnect the control pod interface contact assembly 18, control pod docking magnet 20 and control pod interface 6.

In addition to the Red/IR LEDs, the flexible PCBA 214 includes associated circuitry and components to drive the Red/IR LEDs, a temperature sensor configured to monitor the temperature of the bandage pad during operation, and an electrical connection interface which is operatively connected to the control pod interface contact assembly 18.

Figure 22B:
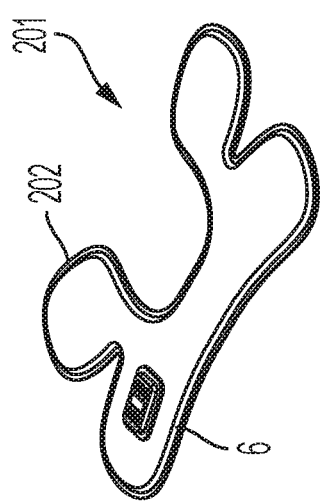
FIGS. 22A and 22B are perspective views of the radiant energy knee bandage pad assembly shown in FIGS. 20A, 20B and 21, without the replaceable adhesive gel layer, according to an exemplary embodiment of this disclosure.
Figure 22A:
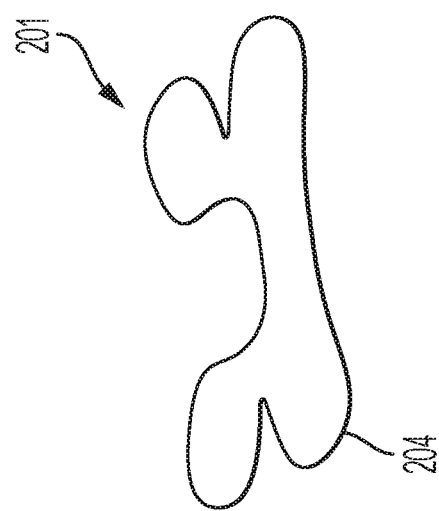

With reference to FIGS. 22A and 22B, illustrated are perspective views of the radiant energy knee bandage pad assembly shown in FIGS. 20A, 20B and 21, without the replaceable adhesive gel layer 208/210, according to an exemplary embodiment of this disclosure.

Figure 23:
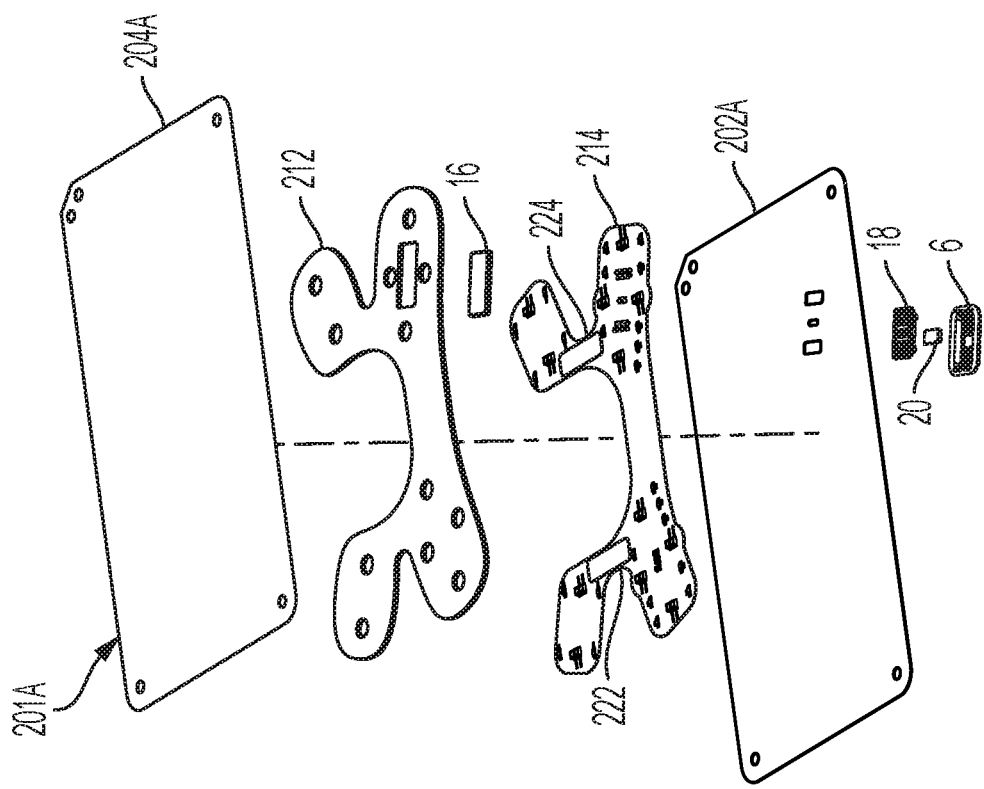
FIG. 23 is an exploded assembly view of the radiant energy knee bandage pad assembly shown in FIGS. 22A and 22B, without the replaceable adhesive gel layer, according to an exemplary embodiment of this disclosure.

With reference to FIG. 23, illustrated is an exploded assembly view of a radiant energy knee bandage pad assembly 201A which is subsequently sonically or HF welded and cut-to-shape to provide the radiant energy knee bandage pad assembly 201 shown in FIGS. 22A and 22B, without the replaceable adhesive gel layer, according to an exemplary embodiment of this disclosure. As shown in FIG. 23, initially an over-sized top layer 202A and over-sized bottom layer 204 are provided and used to encase the pad 212 and flexible PCBA 214. Top layer locators/alignment holes 242, 244, 246, 248 and 250 mate with bottom layer locators/alignment holes 232, 234, 236, 238 and 240, respectively, to align the top layer 202A and bottom layer 204A with the pad 212 and flexible PCBA 214 substantially centered and encased within the top layer 202A and bottom layer 204A.

Next, the top layer 202A and bottom layer 204A are sonically or HF welded at layer locators/alignment holes 232/242, 234/244, 236/246, 238/248 and 240/250 to attach the top layer 202A to the bottom layer 204A.

Next, the oversized top layer 202A and bottom layer 204A are perimeter welded 252/253 substantially near and outside the perimeter of pad 212/flexible PCBA 214. The perimeter welds 252/253 further encases the pad 242 and flexible PCBA 214 and seals the pad 212 and flexible PCBA 214 from the external environment.

Finally, the perimeter welded top layer 202A and bottom layer 204A are simultaneously cut substantially near and outside the perimeter weld to produce the final knee bandage pad assembly 201 including top layer 202 and bottom layer 204 as shown in FIGS. 22A/22B.

Figure 24C:
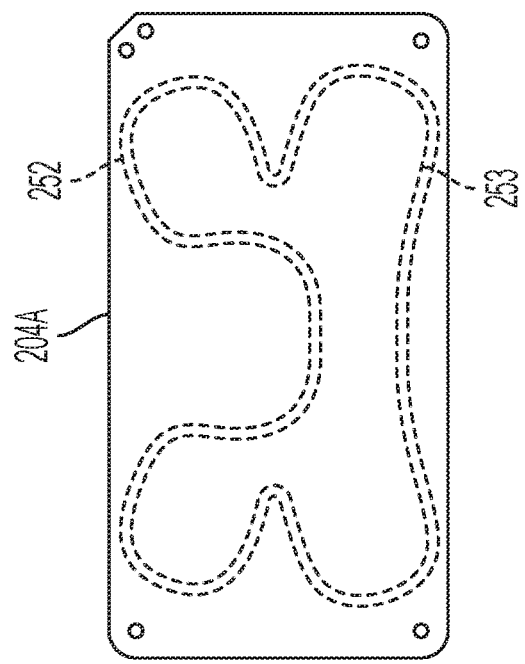
FIGS. 24A, 24B and 24C include a top view, side view and bottom view, respectively, of a radiant energy knee bandage pad assembly including a sonic welded top layer and bottom layer prior to cutting-to-shape, according to an exemplary embodiment of this disclosure.
Figure 24B:
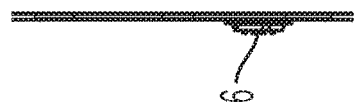
Figure 24A:
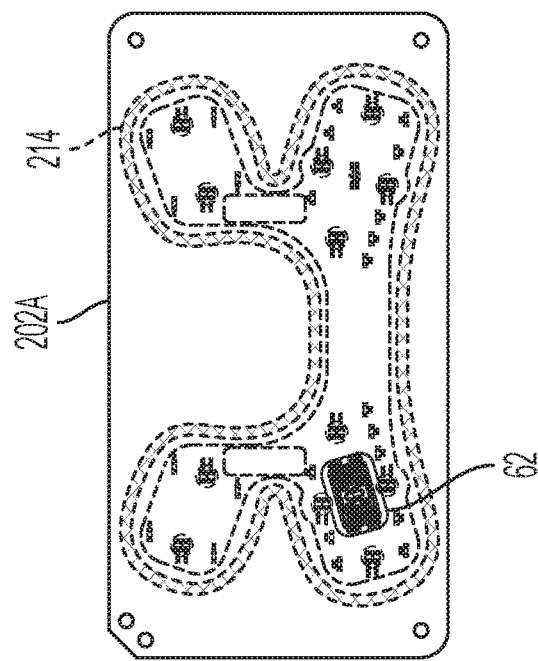

With reference to FIGS. 24A, 24B and 24C, illustrated are a top view, side view and bottom view, respectively, of a radiant energy knee bandage pad assembly 202A including a sonic or HF welded 252/253 top layer and bottom layer prior to cutting-to-shape, according to an exemplary embodiment of this disclosure.

Figures 25A, 25B, 25C:
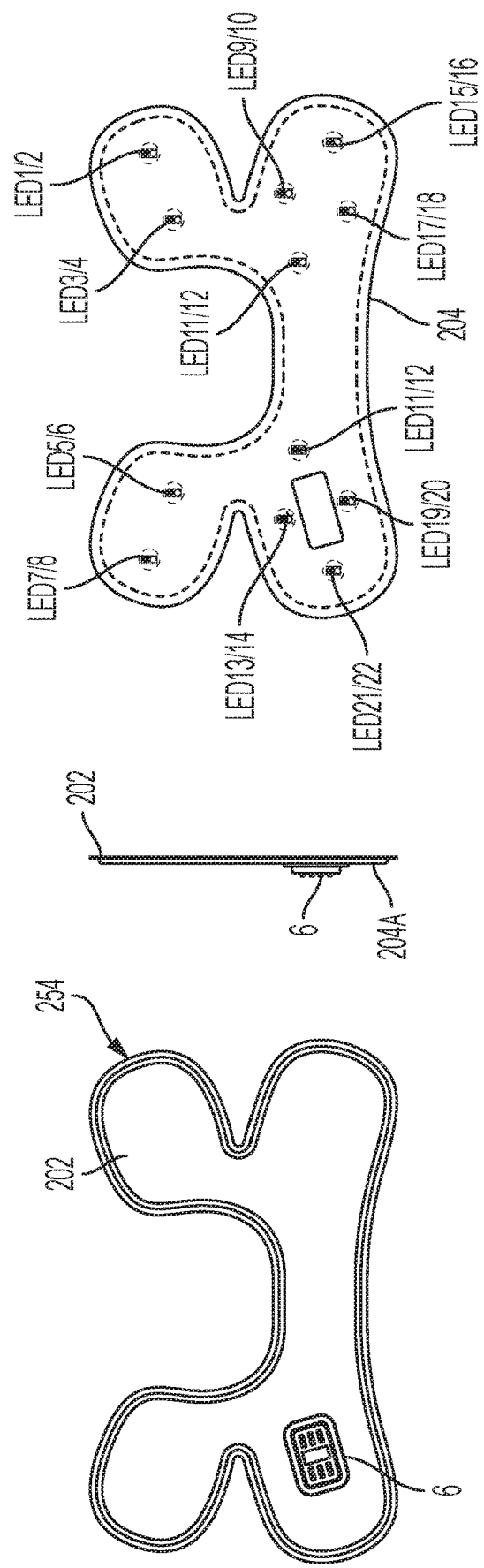
FIGS. 25A, 25B and 25C include a top view, side view and bottom view, respectively, of the radiant energy knee bandage pad assembly shown in FIGS. 24A, 24B and 24C, after the bandage pad assembly is cut-to-shape, according to an exemplary embodiment of this disclosure.

With reference to FIGS. 25A, 25B and 25C, illustrated are a top view, side view and bottom view, respectively, of the radiant energy knee bandage pad assembly shown in FIGS. 24A, 24B and 24C, after the bandage pad assembly 202A is cut-to-shape, according to an exemplary embodiment of this disclosure. As shown, the bandage pad assembly 201A is perimeter cut 254 resulting in an encased bandage pad structure including a multiple lobed or butterfly shaped flexible top layer 202 and multiple lobed transparent flexible bottom layer 204. The final shape can also be described as being substantially symmetrically u-shaped including a right region and left region, each of the right region and left region including a first lobe and second lobe to provide flexibility and conformability of the knee bandage pad assembly 201 to a user treatment surface. FIG. 25C shows the relative locations of LEDs 1-24 to the overall bandage pad assembly 201.

According to an exemplary embodiment of the bandage pad assembly 201, the overall length of the bandage pad is 160-220 mm and the overall width of the bandage pad is 80-130 mm, however, the bandage pad assembly can be of any size provided the number and placement of radiant energy lamps, i.e., LEDs 1-24, and the associated flexible PCBA 214 are configured to provide radiant energy to the user treatment area covered by the bandage pad assembly and attached flexible conformable adhesive gel layer.

Figure 26:
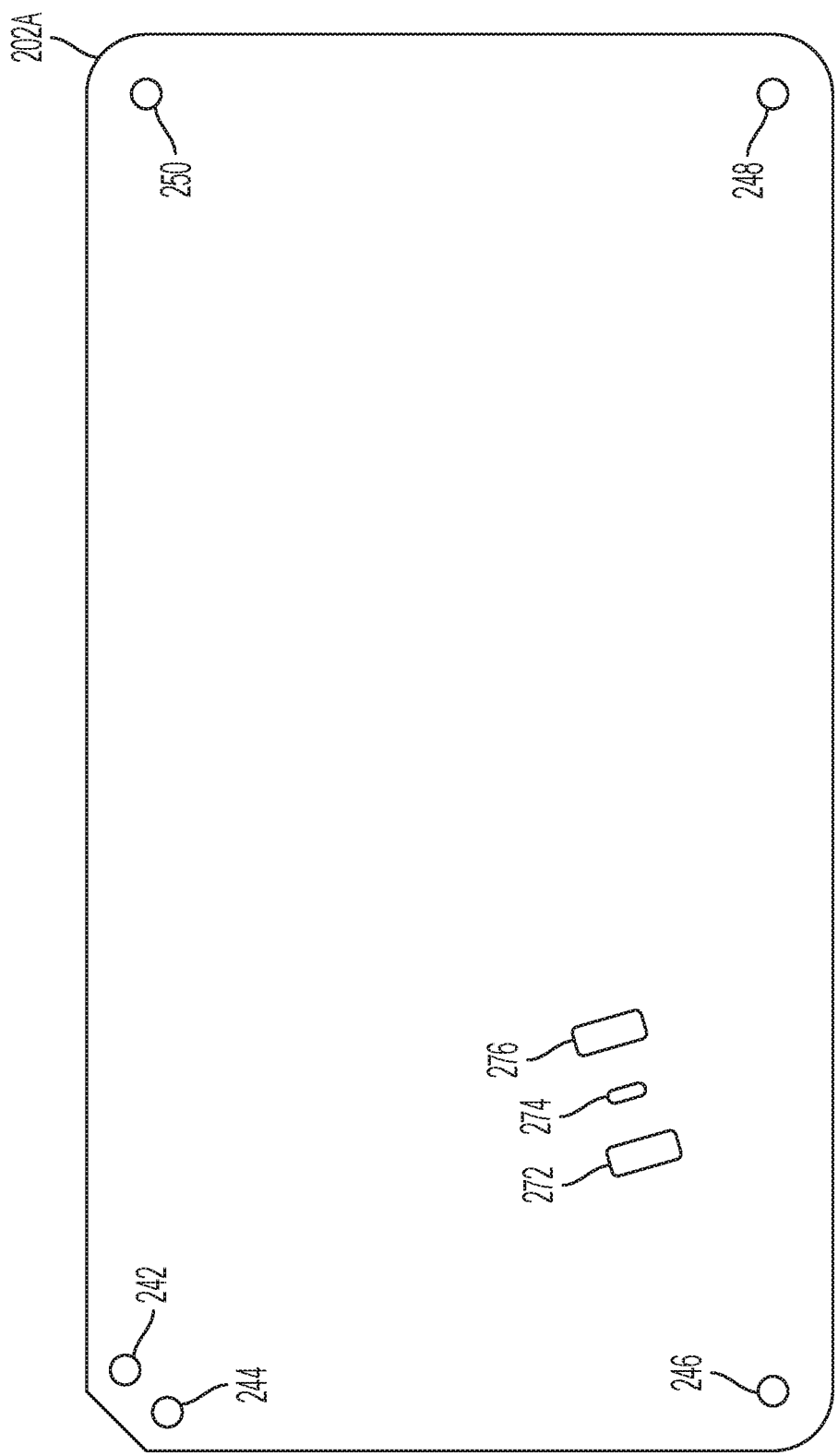
FIG. 26 is a top view of a radiant energy knee bandage pad assembly top layer, according to an exemplary embodiment of this disclosure.

With reference to FIG. 26, illustrated is a top view of a radiant energy knee bandage pad assembly oversize top layer 202A, according to an exemplary embodiment of this disclosure. As shown, the oversize top layer 202A includes locator/alignment holes 242, 244, 246, 248 and 250, and control pod interface clearance holes 272, 274 and 276.

Figure 27:
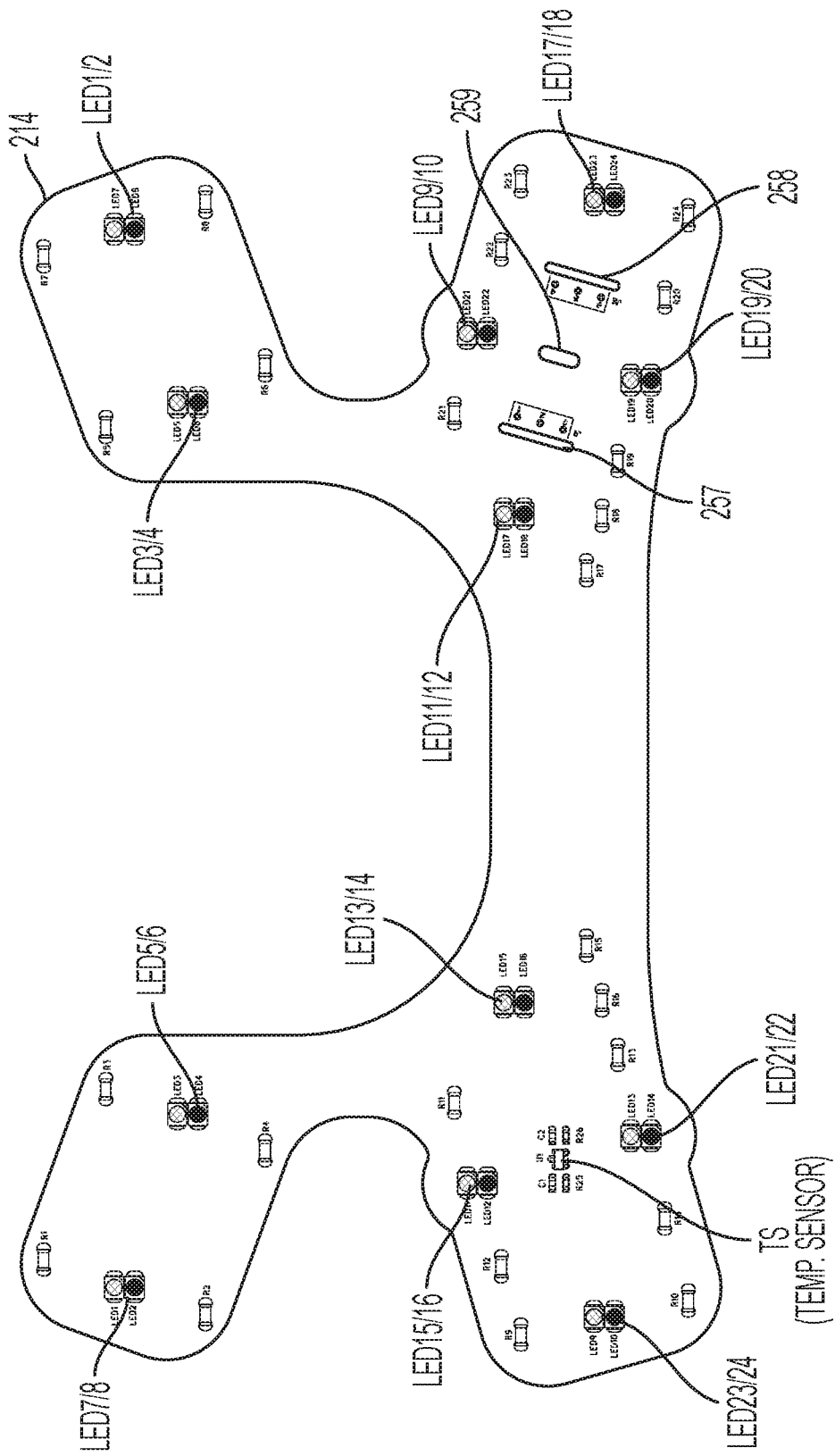
FIG. 27 is a bottom view of a radiant energy knee bandage pad assembly flexible PCBA, according to an exemplary embodiment of this disclosure.

With reference to FIG. 27, illustrated is a bottom view of a radiant energy knee bandage pad assembly flexible PCBA 214, according to an exemplary embodiment of this disclosure. The flexible PCBA 214 is made of a flexible PCBA substrate including conductive tracks and electrical component mounting holes/surfaces. The flexible PCBA also includes control pod interface connection point blocks 257 and 258, each block providing three independent connection points/terminals to electrically connect to the control pod interface contact assembly 218 using electrical conductors/ terminals. Feedthrough hole 259 is provided to extend the control pod interface base 216 from the bottom surface of the flexible PCBA through the feedthrough hole 259 and top layer 202 to operatively attach the control pod interface contact assembly 218 to the bandage pad assembly 201.

LEDs 1-24 and temp sensor TS are mounted to the flexible PCBA along with other associated components such as resistors/capacitors. Each pair of LEDs, i.e., LED 1/2, LED 3/4, LED 5/6, LED 7/8, LED 9/10, LED 11/12, LED 13/14, LED 15/16, LED 17/18, LED 19/20, LED 21/22 and LED 23/24, includes a Red wavelength radiant energy emitting LED and an IR wavelength radiant energy emitting LED. According to an exemplary embodiment, the Red LED specifications include a peak wavelength of 620-640 μm, peak power of >1000 uW and total power of >22.1 mW; the IR LEDs specifications include a peak wavelength of 820-880 μm, peak power of >400 uW and total power of 15.4 mW; and the temperature sensor TS is an analog temperature sensor outputting 10 mV/° C.

The overall shape and size of the flexible PCBA is relatively smaller than the top layer 202/202A and transparent bottom layer 204/204A to enable the flexible PCBA to be encased within the top layer 202 and transparent bottom layer 204 after these layers are spot welded—perimeter welded—perimeter cut as previously described.

While the flexible PCB/PCBA exemplary embodiment described includes Red/IR LEDs and an analog temperature sensor, other LEDs and temperature sensor types are within the scope of this disclosure. For example, LEDs which emit radiant energy at other wavelengths/power and other temperature sensors such as digital temperature sensors.

As previously described with reference to the back bandage pad assembly flexible PCBA 14, FIG. 9 illustrates an electrical schematic of the radiant energy knee bandage pad flexible PCBA 214. As will be further described below, a controller is operatively connected to connection blocks J1 (57) and J2 (58) to power and control the LEDs to emit radiant energy to a user treatment area.

Figure 28:
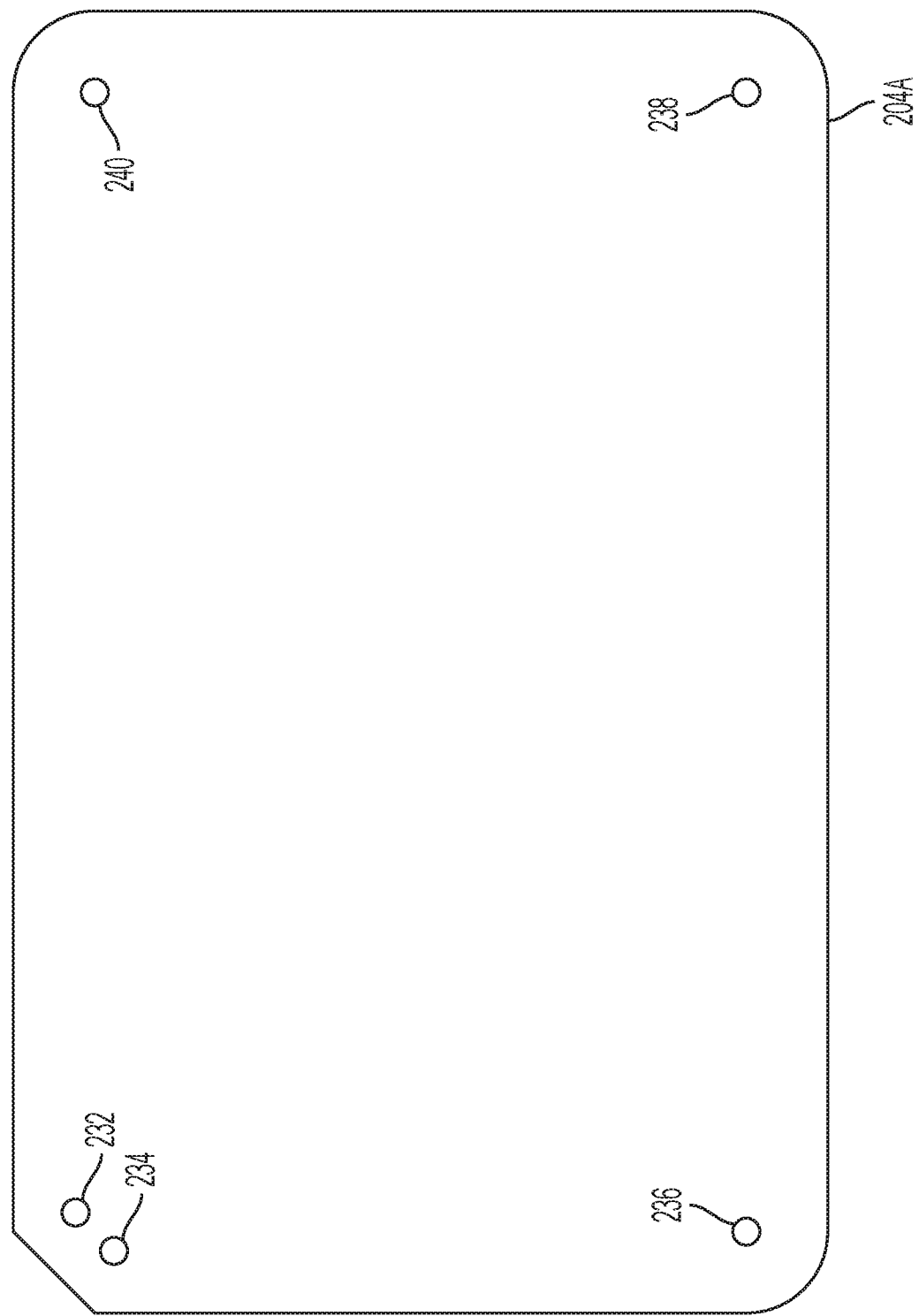
FIG. 28 shows a radiant energy knee bandage pad assembly bottom layer, according to an exemplary embodiment of this disclosure.

With reference to FIG. 28, illustrated is a radiant energy knee bandage pad assembly bottom layer including pad assembly locator/alignment holes 232, 234, 236, 238 and 240 which are mated with corresponding top layer 202A locator alignment holes during assembly of the pad assembly 201, according to an exemplary embodiment of this disclosure.

Figure 29:
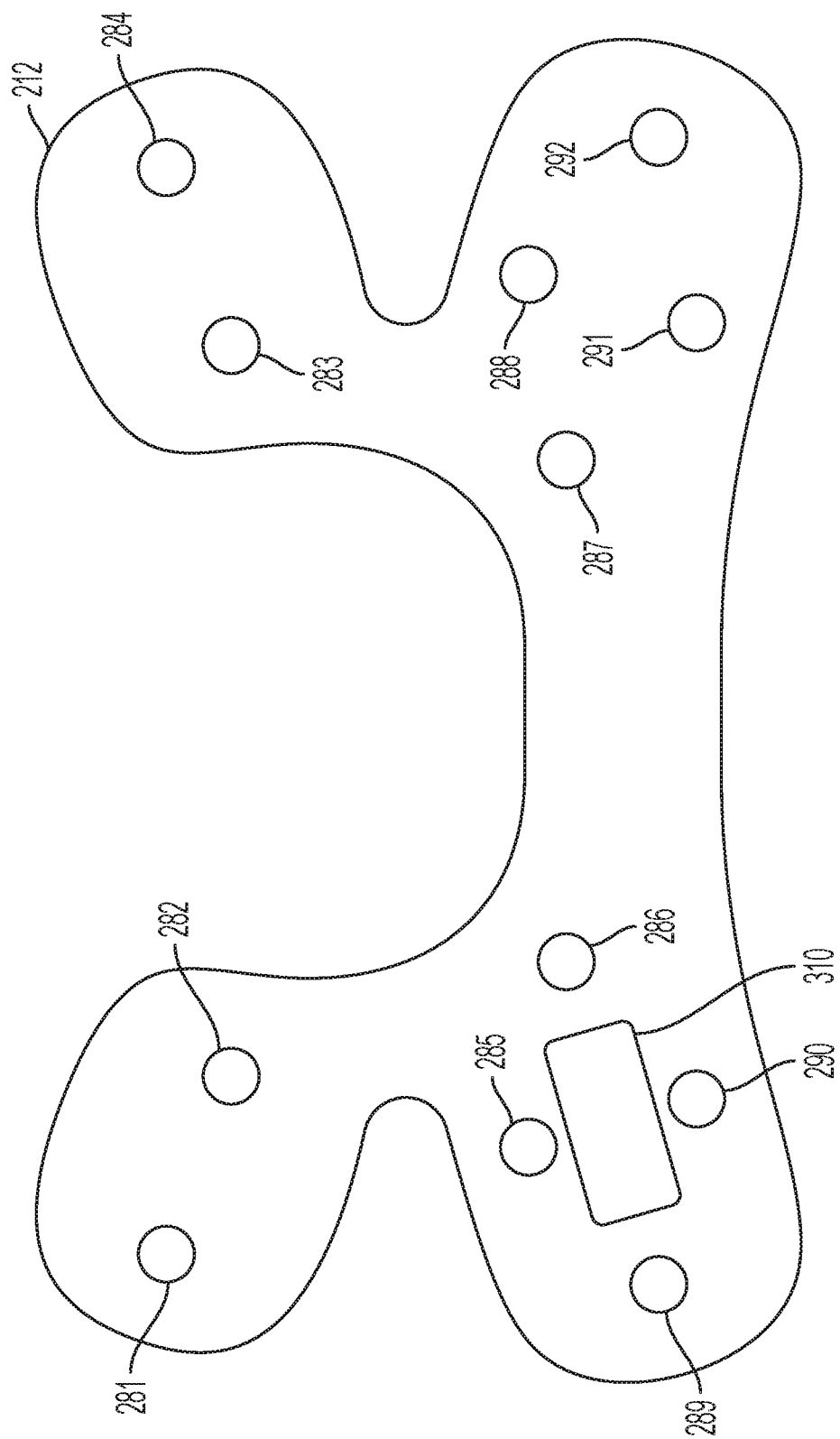
FIG. 29 shows a radiant energy knee bandage pad assembly, according to an exemplary embodiment of this disclosure.

With reference to FIG. 29, illustrated is a radiant energy knee bandage pad 121, according to an exemplary embodiment of this disclosure. As shown, the radiant energy knee bandage pad 212 includes a plurality of apertures 281-292 which extend through the top surface of the bandage pad 212 and bottom surface of the bandage pad 212. The locations of the pad apertures 281-292 correspond and align with the locations of the flexible PCBA 214 LEDs 1-24 such that the Red/IR wavelength energy emitted from LEDs 1-24 is guided through the bandage pad apertures 381-392, and then through the transparent bottom layer 204 and adhesive gel layer apertures 281-292. (FIG. 200) A control pod interface clearance hole 310 provides structural clearance within the pad 212 to accommodate the control pod interface base 216.

According to an exemplary embodiment, the flexible bandage pad 212 is a multiple layer structure including a PE foam and a radiant energy reflective top surface made of mica which is oriented towards the flexible transparent top layer 202 and provides radiant energy reflective properties to reflect/contain radiant energy and heat between the reflective surface and the user treatment area with the bandage assembly applied to the user treatment area using an adhesive conformable gel layer 208/210.

According to another exemplary embodiment, the flexible bandage pad is a single layer of 1 mm to 20 mm thick PE foam or IXPE (Irradiated crosslinked polyethylene foam) with a very fine closed-cell structure. According to an exemplary embodiment, the foam pad 12 is a 1 mm thick IXPE foam pad.

With reference to FIGS. 30, 31 and 32, FIG. 30 illustrates a perspective view of a radiant energy knee bandage pad assembly adhesive gel refill assembly 320 according to an exemplary embodiment of this disclosure; FIG. 31 illustrates an exploded view of the radiant energy knee bandage pad assembly adhesive gel refill assembly 320 shown in FIG. 30; and FIG. 32 illustrates a top view of the radiant energy knee bandage pad assembly adhesive gel refill assembly 320 shown in FIG. 30. The adhesive gel refill assembly 320 includes a first adhesive gel layer 208 and a second adhesive gel layer 210, packaged in a foldable booklet type arrangement. The right side of the gel refill assembly 320 includes a top liner 322, a middle liner 326, an adhesive gel layer 210, a backer 324 and a tape strip 328. The left side of the refill includes a top liner 332, a middle layer (not shown), an adhesive gel layer 208 (not shown), a backer (not shown) and a tape strip (not shown). The gel refill 320 is perforated between the first and second gel layers 208/210 to enable a user to separate each gel layer from the other.

Figure 33B:
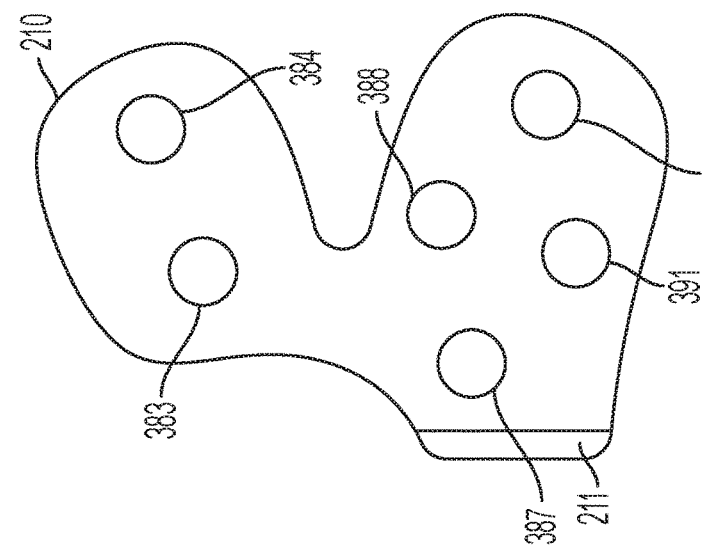
FIGS. 33A and 33B are top views and FIGS. 33C and 33D are front views of a first portion and second portion of an adhesive gel refill which attach to the bottom layer of a radiant energy knee bandage pad assembly, according to an exemplary embodiment of this disclosure.
Figure 33D:
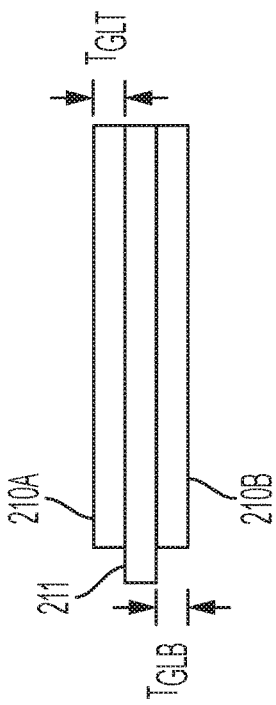
Figure 33A:
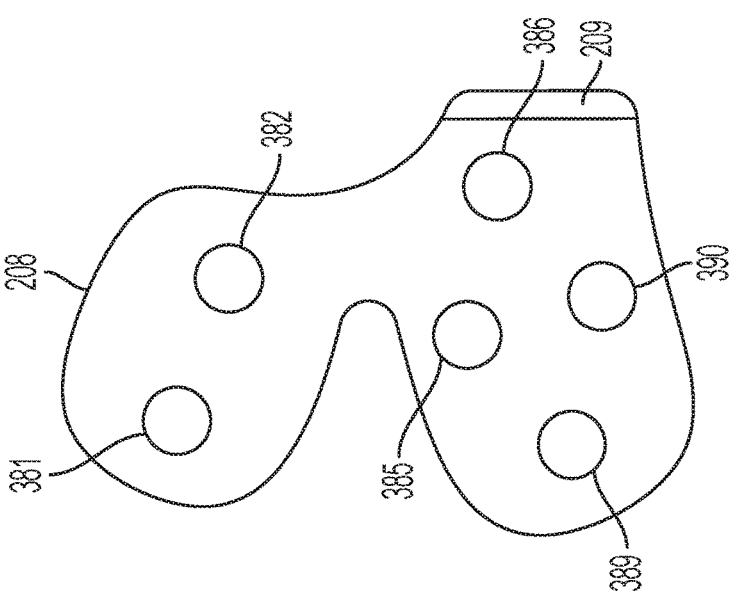

With reference to FIGS. 33A and 33B, illustrated are top views of a first portion 208 and second portion 210 of an adhesive gel refill which attach to the bottom layer of a radiant energy knee bandage pad assembly, according to an exemplary embodiment of this disclosure.

As shown, each of the first and second portions of the adhesive gel refill includes a plurality of apertures. The first adhesive gel layer 208 includes apertures 381, 382, 385, 386, 389 and 390, and the second adhesive gel layer 210 includes apertures 383, 384, 387, 388, 391 and 392.

According to an exemplary embodiment, the adhesive gel layers 208 and 210 are made of a high tack double-sided reinforced hydrogel with a minimum thickness of 1.0 mm. The composition of the adhesive gel layers 208 and 210 provides a flexible conformable surface to apply the radiant energy bandage pad assembly to a user treatment area. The gel layer apertures 381-392 are aligned with the bandage pad apertures 281-292 to guide radiant energy from LEDs 1-24 to the user treatment area.

Furthermore, the conformable surface of the gel layers 8 and 10 adheres to the radiant energy bandage pad bottom layer 4 and the user treatment area to provide zero-air-gap heat conduction interfaces to efficiently transfer heat generated from the LEDs through the gel layers to the user treatment area. According to an exemplary embodiment of this disclosure, the gel layers are made of a clear transparent homogeneous hydrogel with a thermal conductivity of approximately 0.59 W/m-K (Watts per meter-Kelvin), such as is available from © First Water Limited, 2015 (a © Scapa 2018 Healthcare Company) as Product Adhesive Gel Back Bandage.

Figure 33C:
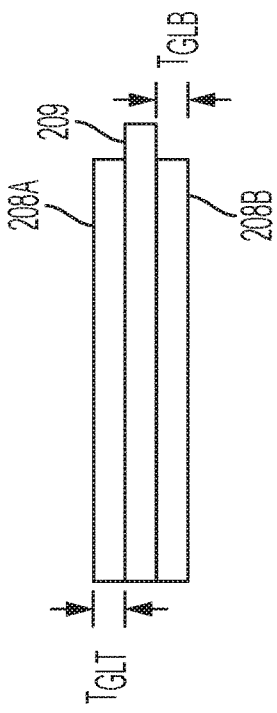

With reference to FIGS. 33C and 33D, illustrated are front views of an adhesive gel first portion 208 and second portion 210 according to another exemplary embodiment of this disclosure. As shown, the adhesive gel layers include a multiple layer composition including top layers of a clear hydrogel 209A/210A, bottom layers of the clear hydrogel and a middle transparent substrate 209/211 sandwiched between the top and bottom hydro gel layers. According to an exemplary embodiment, the middle transparent substrate is a non-woven polyester scrim which extends beyond one side of each hydro gel portion to create a dry, non-sticky user handling tab for removing of the adhesive adhesive gel layers 208/210 from the radiant energy back bandage assembly 201. According to an exemplary embodiment, the middle substrates are set at 60:40, where the middle substrate is located where the thickness $T_{GLT}$ of the top clear hydrogel layers 208A/210A is approximately 60% and the thickness $T_{GLB}$ of the bottom clear hydrogel layers 208B/210B is 40%. While the exemplary embodiment described includes a 60:40 set of the middle substrate, also referred to a scrim, other sets are within the scope of this disclosure, for example a set of 50:50, 55:45, 65:35, etc. The set of the scrim can be selected depending on the desired adhesive and conformably performance of the adhesive gel layers to the user treatment surface, as well as the desired ease of removability of the adhesive gel layers from the radiant energy bandage assembly bottom layer or gel/bandage interface.

Figure 35:
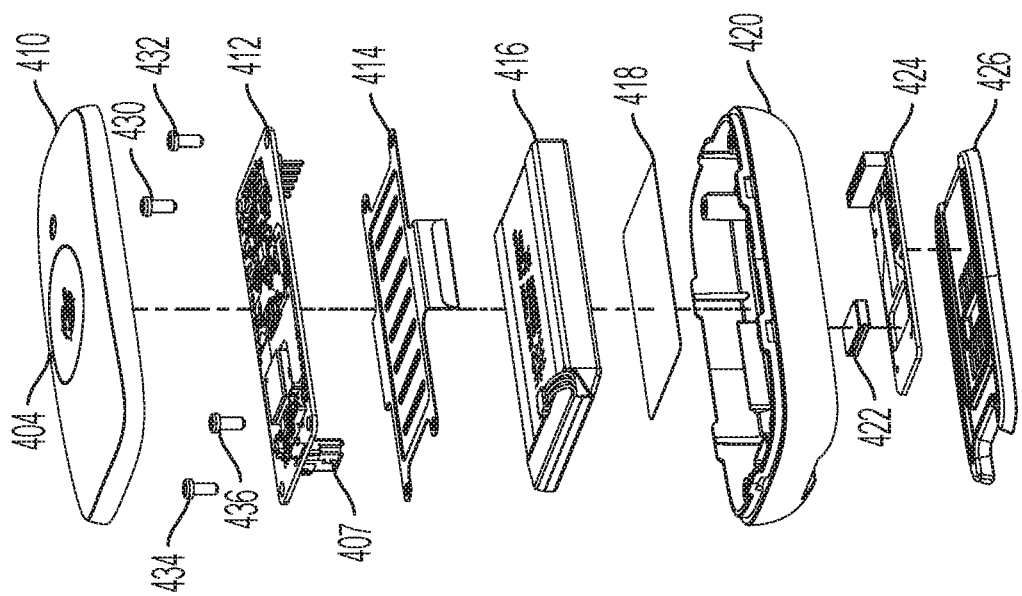
FIG. 35 is an exploded assembly view of the radiant energy bandage pad controller shown in FIGS. 34A and 34B.
Figure 34B:
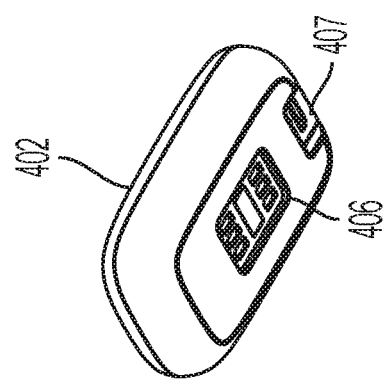
FIGS. 34A and 34B are top and bottom perspective views, respectively, of a radiant energy bandage pad controller, according to an exemplary embodiment of this disclosure.
Figure 34A:
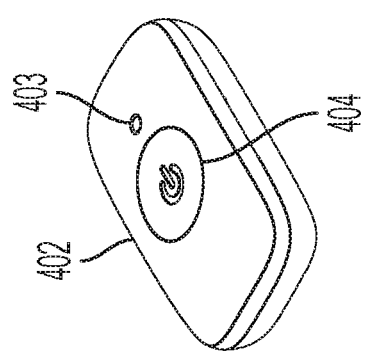

With reference to FIGS. 34A and 34B, illustrated are top and bottom perspective views, respectively, of a radiant energy bandage pad controller 402, according to an exemplary embodiment of this disclosure, and FIG. 35 is an exploded assembly view of the radiant energy bandage pad controller 402 shown in FIGS. 34A and 34B. As shown, the external surfaces of the control pod 402 include a user control switch/button 404, an indicator LED 403, a control pod/bandage interface 406 and a USB connection interface 407. The construction of the control pod 402 includes a top housing 410 and a bottom housing 420 which encase a main PCBA 412, a battery plate 414, and a Li—Po battery assembly 416. Fasteners 430, 432, 434 and 436 attach the main PCBA 412 to the bottom housing 420 and the battery 416 is attached to the bottom housing 420 with an adhesive strip 418. Attached underneath the bottom housing 420 is a weld plate 426, daughter PCBA 424 and block magnet 422 which provide docking/mating of the control pod 402 to a radiant energy bandage pad assembly, such as a back bandage pad assembly 1 and knee bandage pad assembly 201 as previously described.

Figure 37:
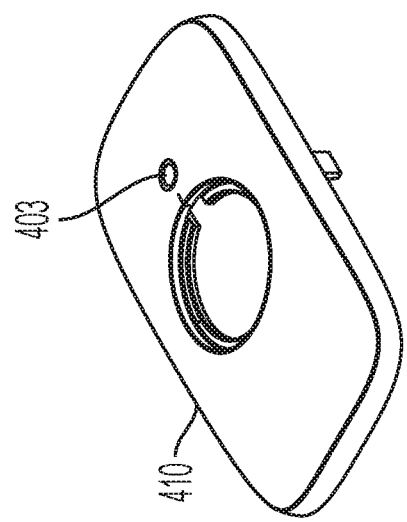
FIG. 37 is another perspective view of the radiant energy controller pod upper housing shown in FIGS. 36A and 36B.
Figure 36B:
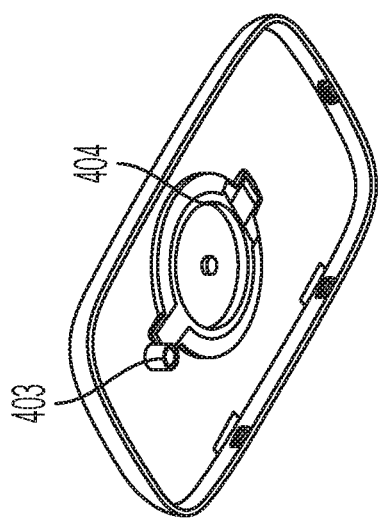
FIGS. 36A and 36B are perspective views of a radiant energy controller pod upper housing, according to an exemplary embodiment of this disclosure.
Figure 36A:
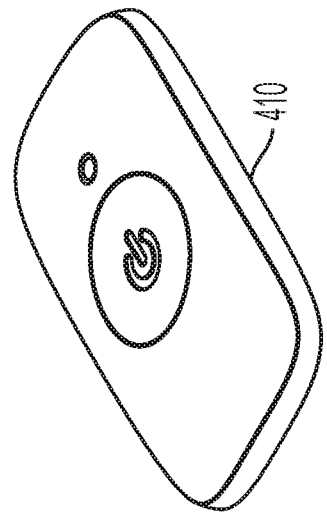

With reference to FIGS. 36A and 36B, illustrated are additional perspective views of a radiant energy controller pod upper housing 410, according to an exemplary embodiment of this disclosure, and FIG. 37 is another perspective view of the radiant energy controller pod upper housing 410 shown in FIGS. 36A and 36B.

Figure 38:
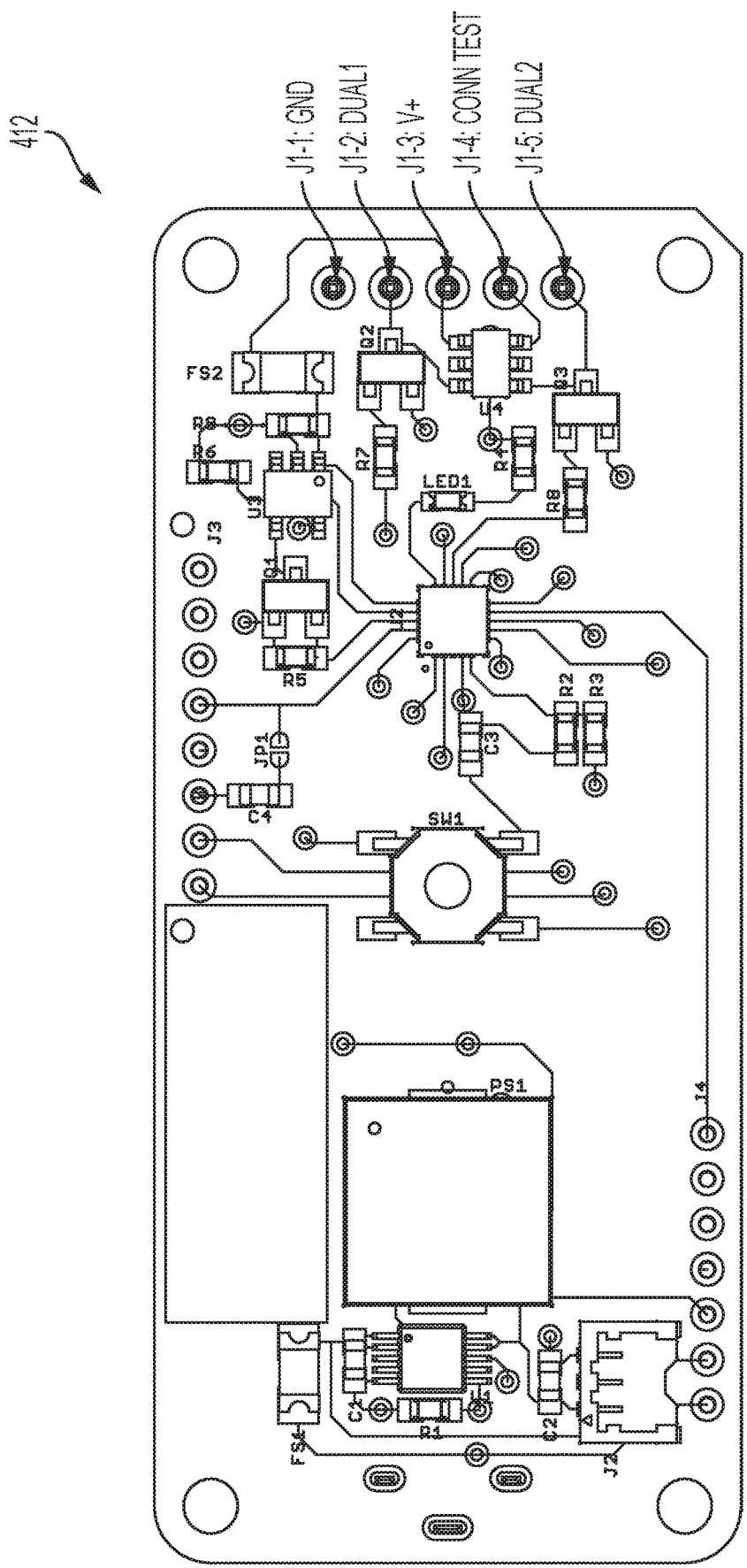
FIG. 38 is a top view of a control pod main PCBA, according to an exemplary embodiment of this disclosure.

With reference to FIG. 38, illustrated is a top view of a control pod main PCBA 412, according to an exemplary embodiment of this disclosure. As shown, the main PCBA includes a plurality of interface connection points, including J1-1, J1-2, J1-3, J1-4 and J1-5 which operatively connected to the daughter PCBA 424 shown in FIGS. 41A-C. The daughter PCBA 424 provides electrical pads 417 to establish electrical connections with the bandage pad assembly spring contacts 114.

Figure 39B:
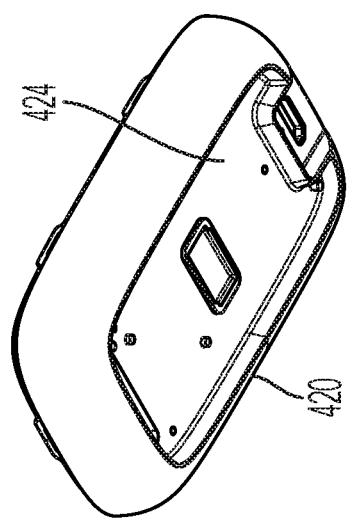
FIGS. 39A and 39B are perspective views of a radiant energy controller pod lower housing, according to an exemplary embodiment of this disclosure.
Figure 39A:
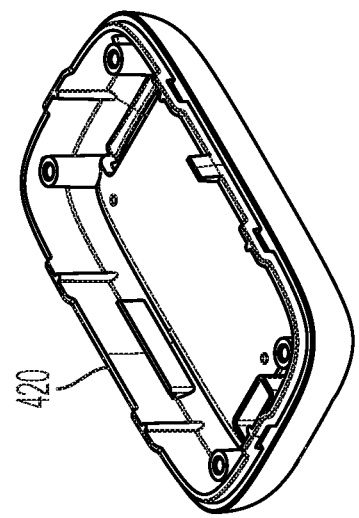

With reference to FIGS. 39A and 39B, illustrated are additional perspective views of a radiant energy controller pod lower housing 420, according to an exemplary embodiment of this disclosure.

Figure 40:
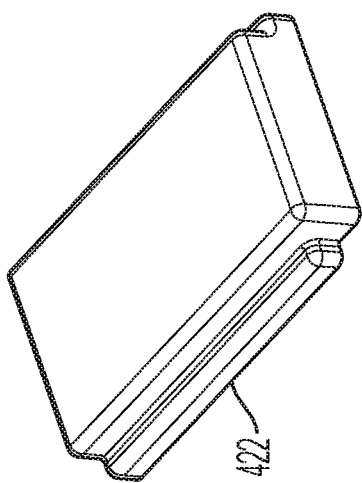
FIG. 40 is a perspective view of a radiant energy controller pod block magnet, according to an exemplary embodiment of this disclosure.

With reference to FIG. 40, illustrated is a perspective view of a radiant energy controller pod block magnet 422, according to an exemplary embodiment of this disclosure. As shown, the block magnet 422 includes protruding side members which retain the block magnet 422 between the control pod lower housing 420 and the daughter PCBA 424/weld plate 426. According to an exemplary embodiment, the block magnet 422 is a sintered neodymium iron boron (NdFeB) permanent magnet with a minimum 11.1 N (2.5 Lb) pull force.

Figure 41A:
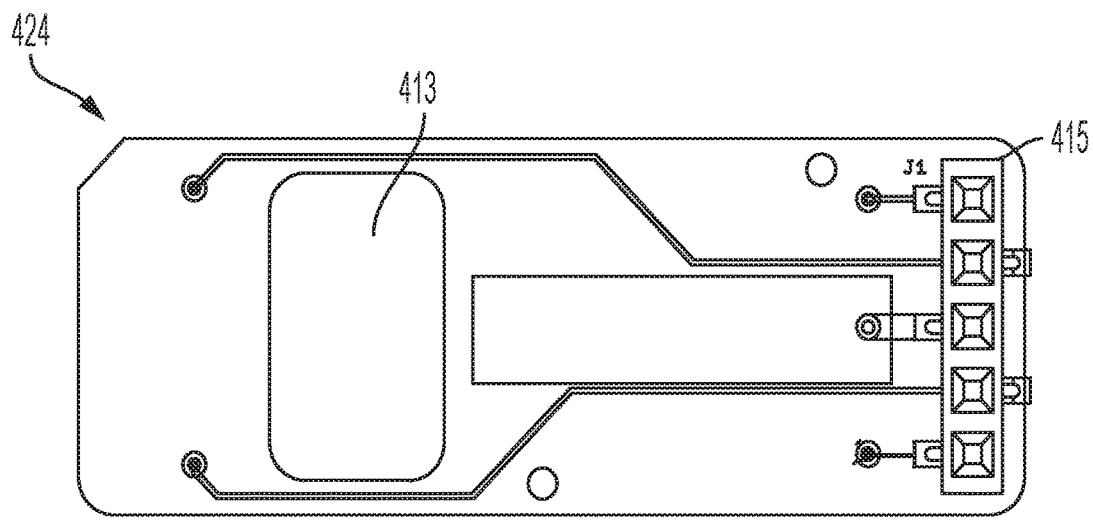
FIGS. 41A, 41B and 41C are a bottom view, side view and top view, respectively, of a control pod daughter PCBA, according to an exemplary embodiment of this disclosure.
Figure 41B:
Figure 41C:
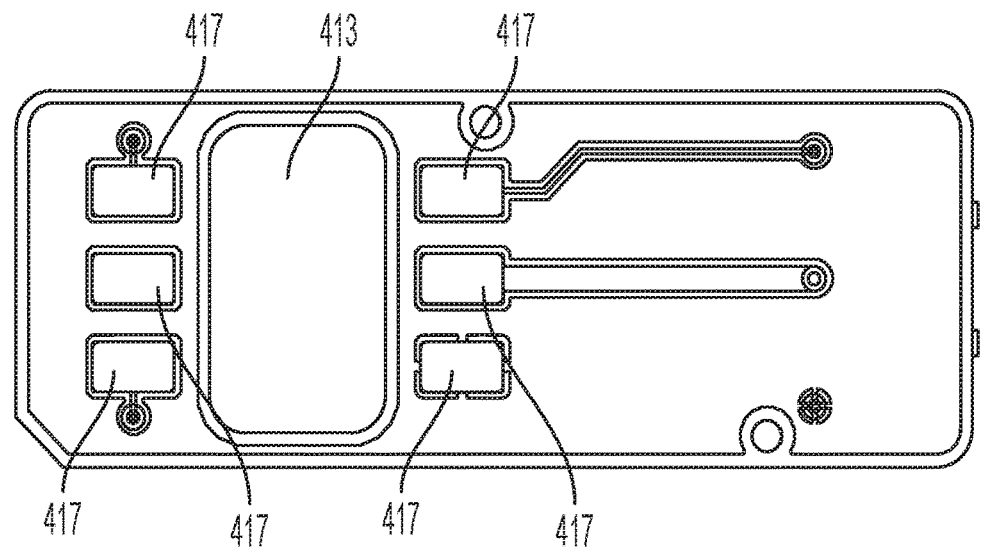

With reference to FIGS. 41A, 41B and 41C, illustrated are a bottom view, side view and top view, respectively, of a control pod daughter PCBA 424, according to an exemplary embodiment of this disclosure. As shown, the control pod block magnet receiving window 413 exposes a face of the block magnet 416 to provide docking/mating of the bandage pad assembly electrical spring contacts 114 to the conductive pads 417. Electrical connection terminals 415 mate with J1 connection points on the main PCBA 412.

Figure 42B:
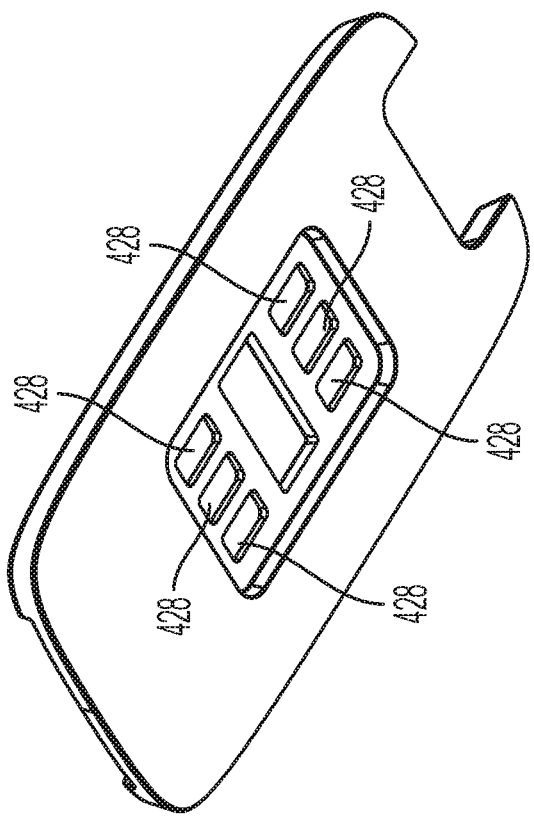
FIGS. 42A and 42B are perspective views of a radiant energy controller pod weld plate, according to an exemplary embodiment of this disclosure.
Figure 42A:
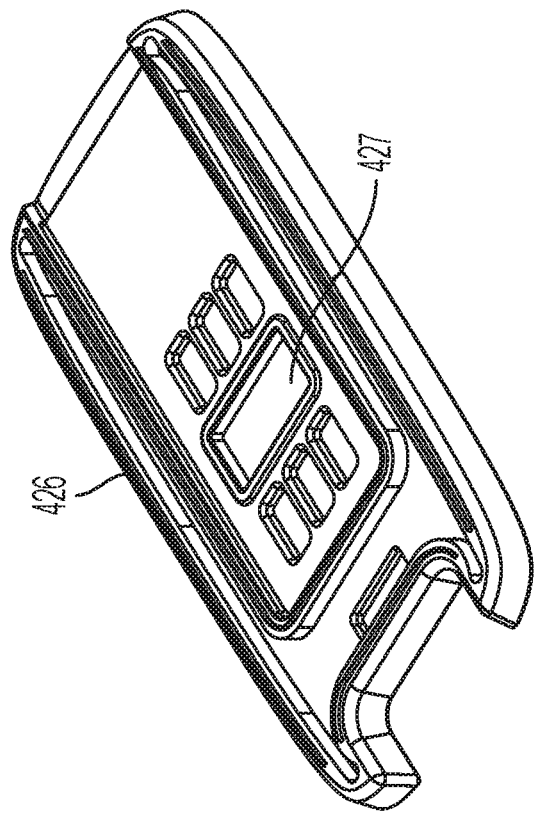
Figure 43B:
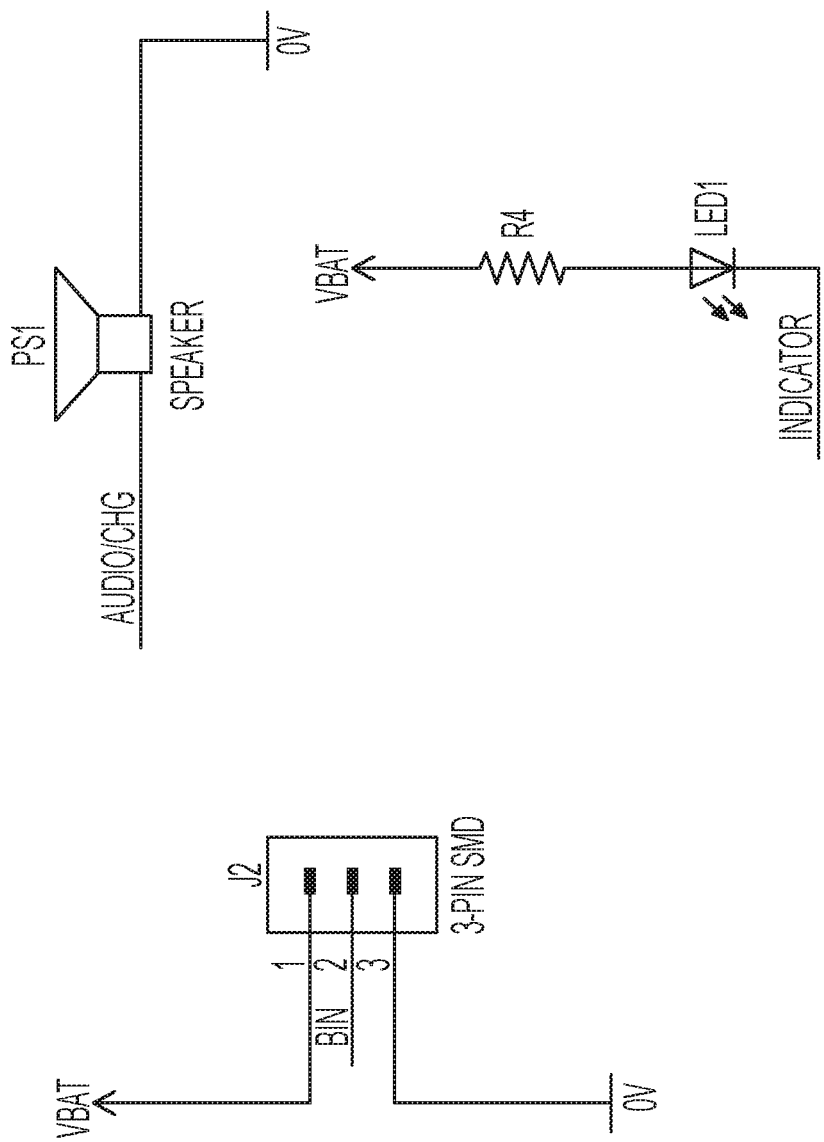
Figure 43C:
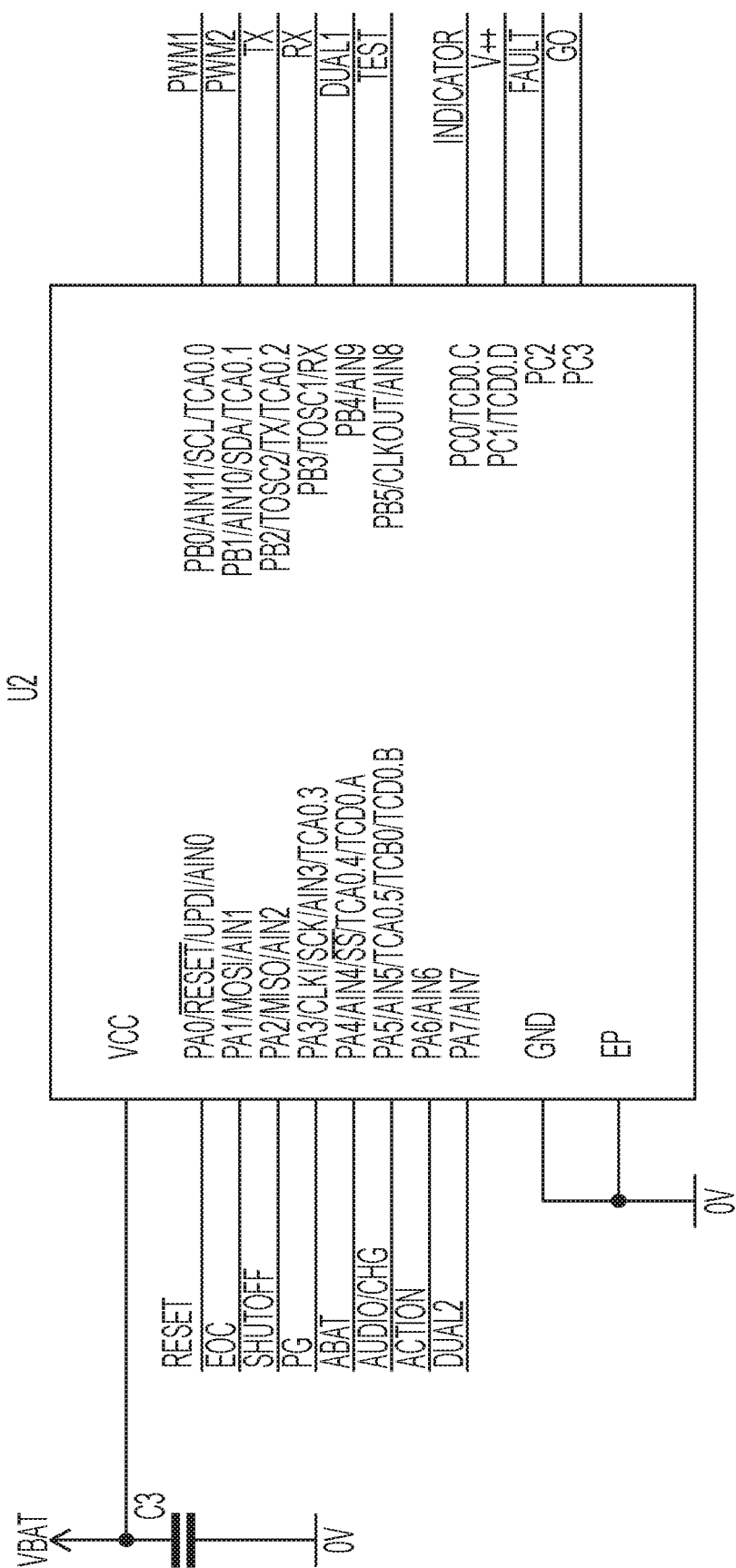
Figure 43D:
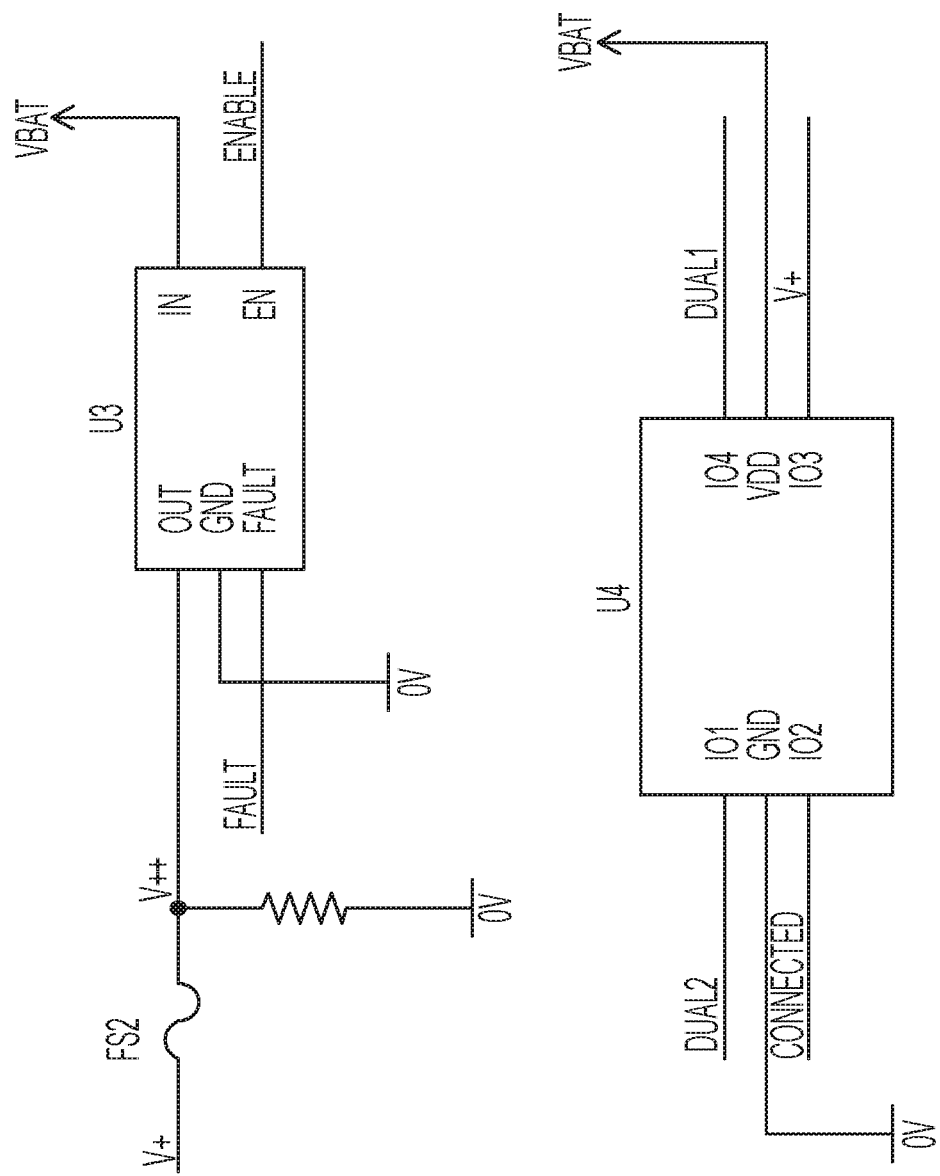
Figure 43E:
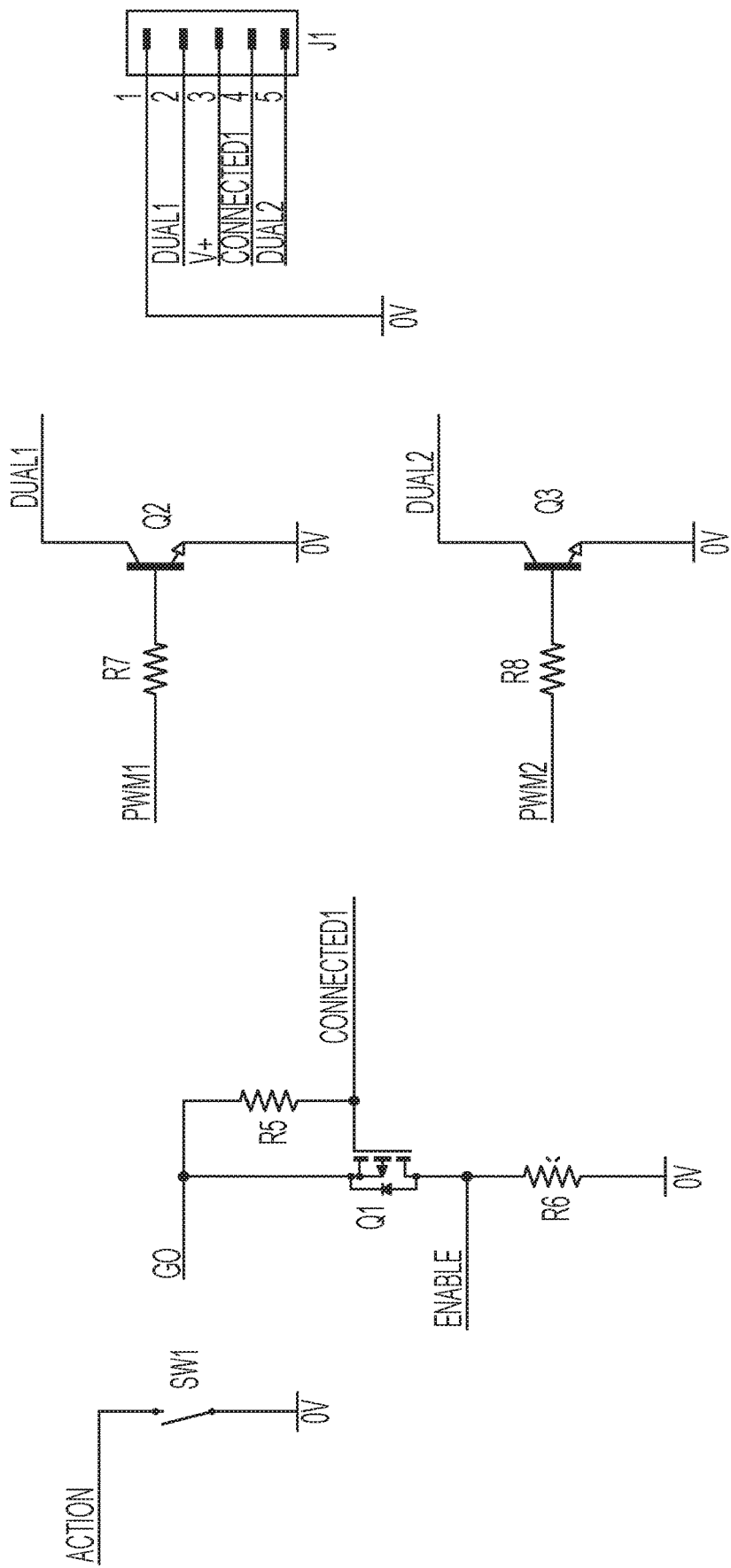

With reference to FIGS. 42A and 42B, illustrated are perspective views of a radiant energy controller pod weld plate 426, according to an exemplary embodiment of this disclosure. As shown, the control pod weld plate 426 includes a block magnet clearance window 427 to expose a face of the block magnet and feedthrough holes 428 to provide a protected electrical interface of the daughter PCBA connection pads 417 to the bandage pad spring contacts 114.

With reference to FIGS. 43A-43E, illustrated is a schematic of a radiant energy controller pod 402, according to an exemplary embodiment of this disclosure. As shown, the control pod main PCBA 412 includes a main controller U2 operatively associated with a USB interface, user control switch SW1, battery monitoring circuit U1, an audio speaker circuit PS1, indicator LED circuit U3/R9, PWM LED driver circuits Q2/R7 and Q3/R8, a connection state circuit Q1/R5/56 and U4, and daughter PCBA 424 interface J1.

Figure 44A:
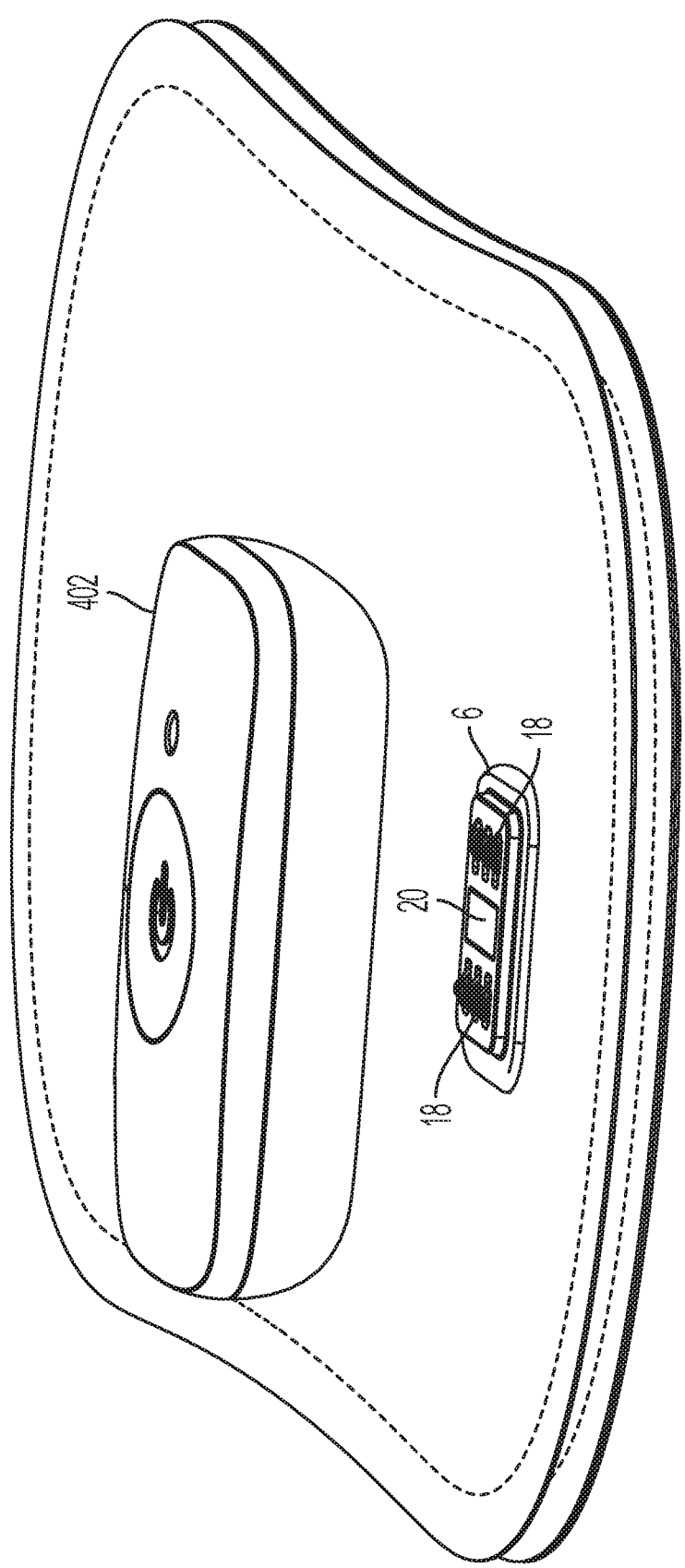
FIGS. 44A-44E are various views of a magnetic docking/connection of a control pod to a bandage pad assembly, according to an exemplary embodiment of this disclosure.
Figure 44B:
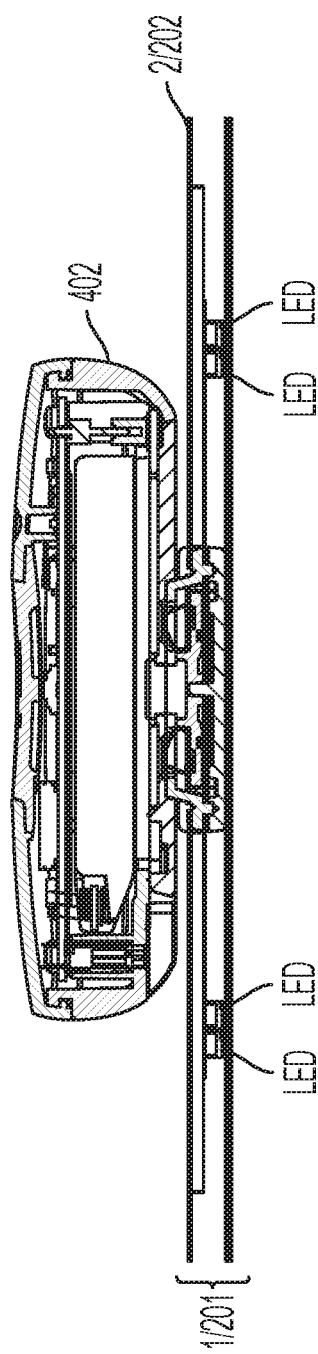
Figure 44C:
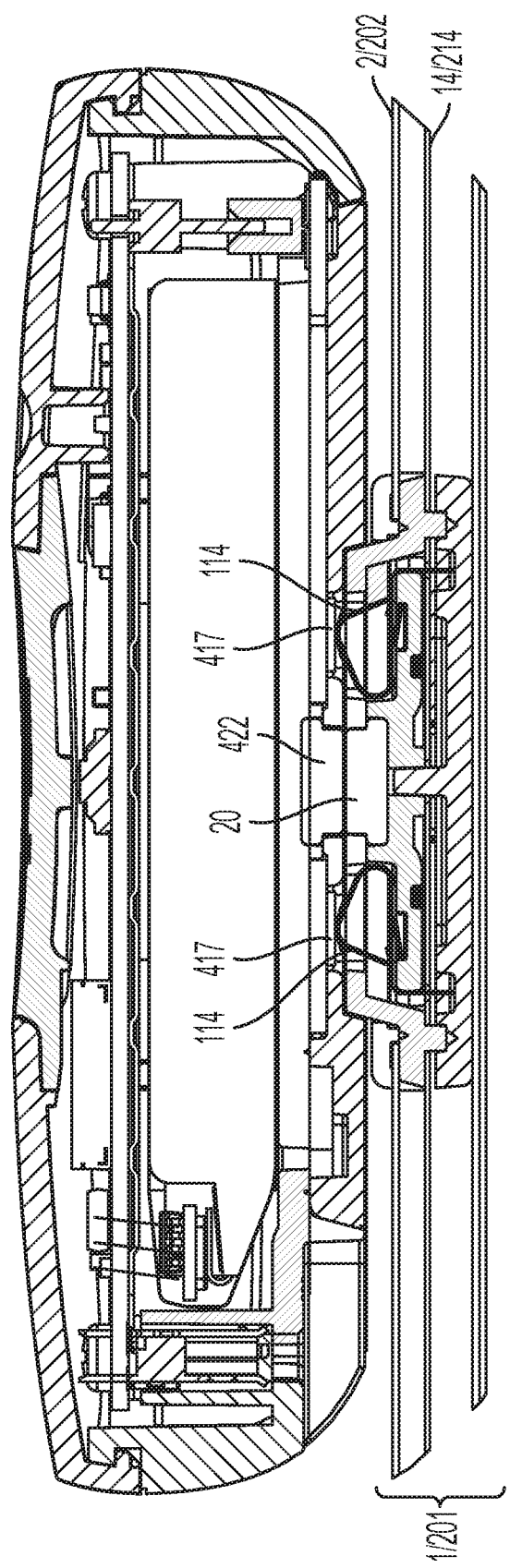
Figure 44D:
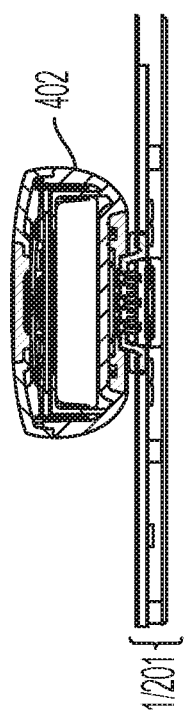
Figure 44E:
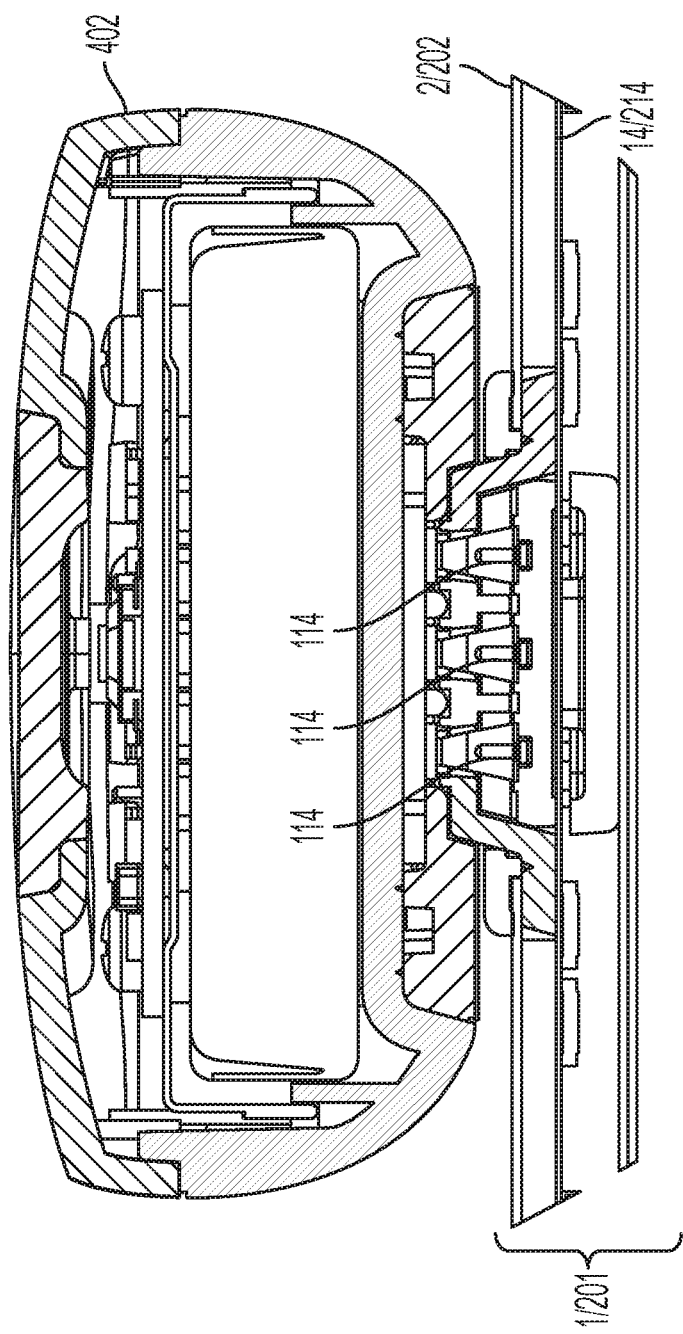

With reference to FIGS. 44A-44E, illustrated are various detail views of a magnetic docking/connection of a control pod to a bandage pad assembly, according to an exemplary embodiment of this disclosure. FIG. 44A is a perspective view of the relative alignment of a control pod 402 (as shown or rotated 180 degrees) and radiant energy bandage pad assembly control pod interface to operatively connect the control pod and bandage pad assembly; FIGS. 44B and 44C are detailed views of the engagement of the pad spring contacts 114, control pod connection pads 417, and relationship of the pad block magnet 20/control pod block magnet 422 with the control pod 402 connected to a bandage pad assembly 2/202; and FIGS. 44D and 44E are orthogonal detail views, relative to FIGS. 44B and 44C, of the control pod 402 connected to a bandage pad assembly 2/202.

Figure 45A:
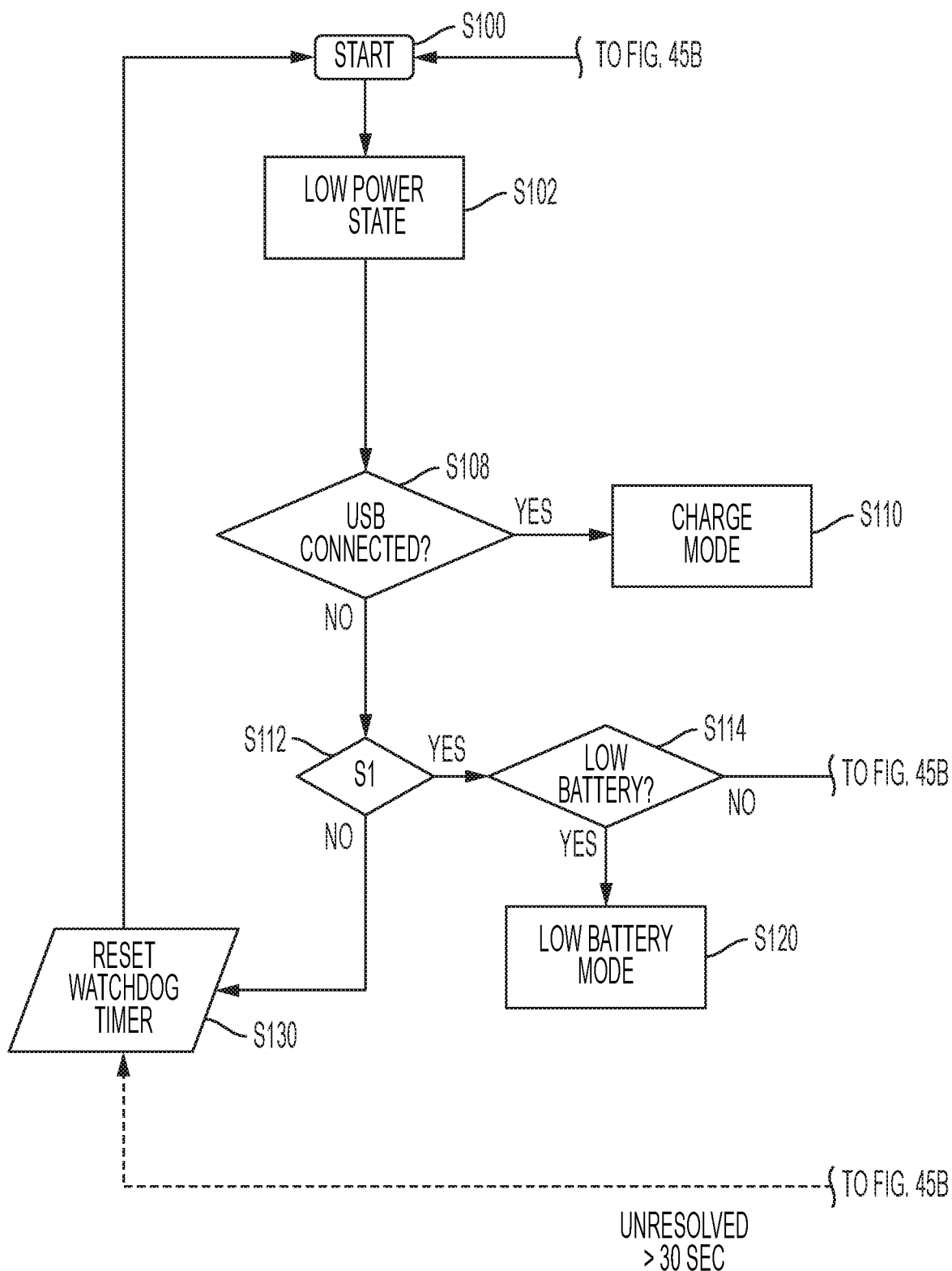
FIGS. 45A and 45B illustrate a radiant energy bandage operation associated with a radiant energy back/knee bandage pad assembly operatively connected to a control pod, according to an exemplary embodiment of this disclosure.
Figure 45:
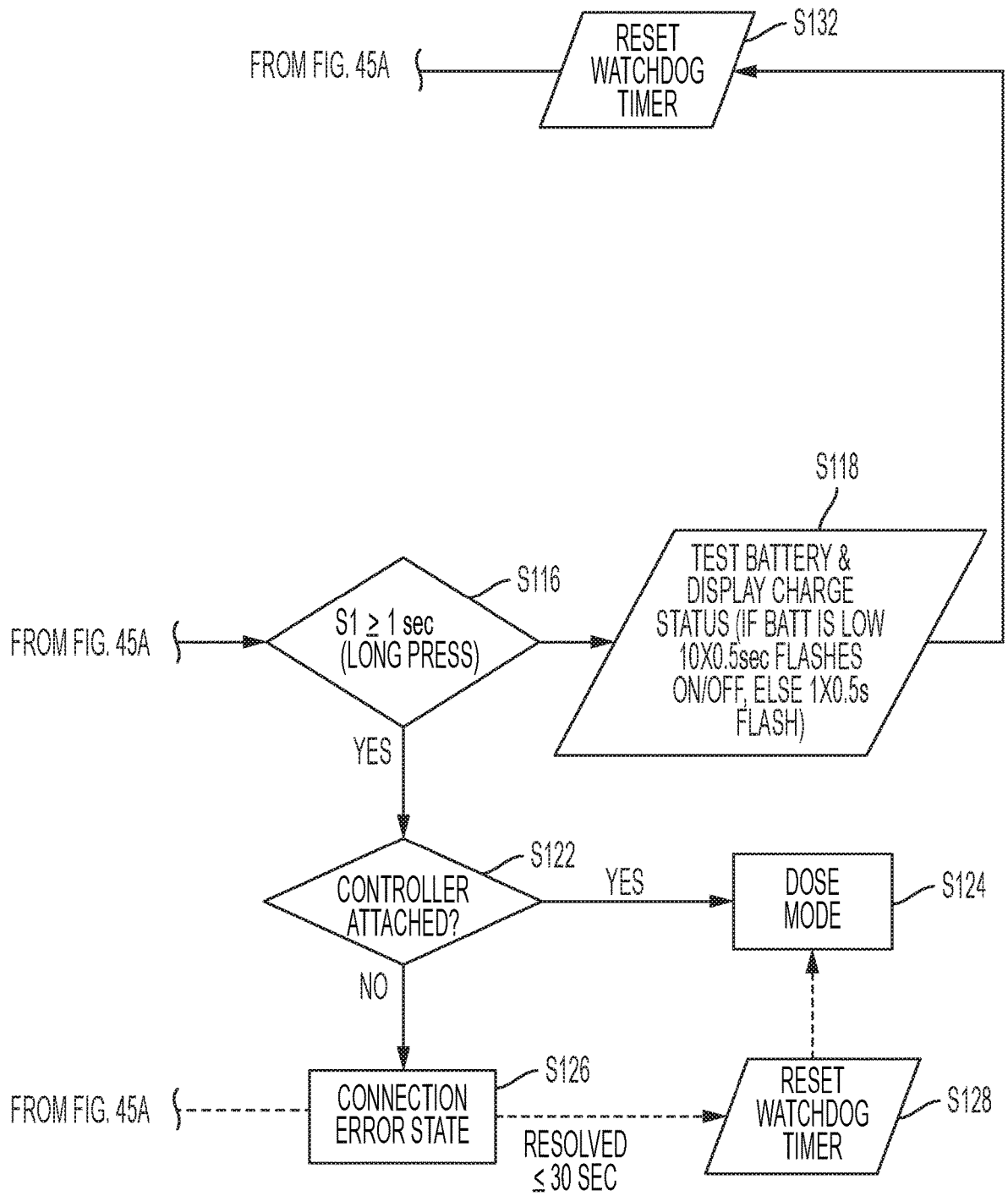

With reference to FIGS. 45A and 45B, illustrated is a radiant energy bandage operation associated with a radiant energy back/knee bandage pad assembly operatively connected to a control pod, according to an exemplary embodiment of this disclosure.

Initially, at step S100, control program starts.

Next, at step S102, the control program determines if a low power state of the battery is present. If the power state of the battery is acceptable, the control program continues to S108. If the control program determines a low battery state exists, a low battery state program is performed as described with reference to FIG. 46 below.

At step S108, the control program determines if a USB communication device is connected to the control pod. If a USB connection is established, the control program performs a controller charging state program as will be described with reference to FIG. 47 below. If a USB connection state is not established, the control program executes step S112.

At step S112, the control program determines if the user control switch S1 is closed. If SW1 is not closed, the control program executes step S130 and resets a watchdog timer and returns to the start of the control program S100. If the user control switch is closed, the control program performs a test of the battery condition of step S114.

At step S114, the control program executes the low battery mode program if a low battery condition exists, otherwise, the control program executes step S116.

At step S116, the control program determines if the user control switch SW1 has been pressed for a "long period of time", for example, greater than or equal to 1 second. If user control switch SW1 is pressed less than 1 second, the control program executes step S118 and tests the battery display's charge status, resets watchdog timer S132 and returns to the start of the control program S100. If user control switch SW1 is pressed for a "long period of time", the control program executes step S122.

At step S122, the control program determines if the pod controller is operatively connected to a bandage pad assembly. If the pod controller is not operatively connected to a bandage pad assembly, the controller performs a connection error state program at step S126 which either resolves the connection error and resets the watchdog timer at step S128, or generates an indication of an unresolved connection error state, resets the watchdog timer at step S130 and returns to the start of the control program at step S100. If at step S122 the control program determines the control pod is appropriately operatively connected to the bandage pad assembly or the connection error state is resolved and the watchdog timer is reset at step S128, the control program executes a dose mode program to power and control the bandage pad assembly to deliver a dose of radiant energy to the user treatment area.

Figure 46:
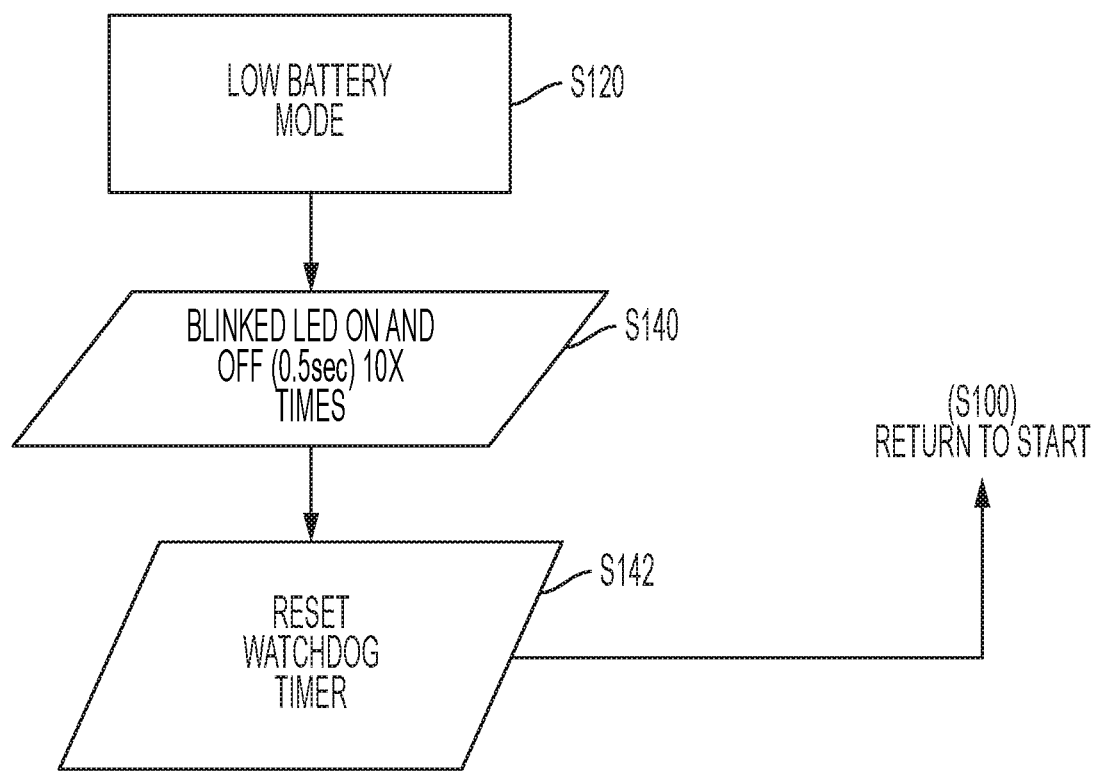
FIG. 46 is a control pod operational flow chart of a low battery state associated with a radiant energy back/knee bandage pad assembly operatively connected to a control pod, according to an exemplary embodiment of this disclosure.

With reference to FIG. 46, illustrated is a control pod operational flow chart of a low battery state associated with a radiant energy back/knee bandage pad assembly operatively connected to a control pod, according to an exemplary embodiment of this disclosure.

After entering the low battery mode at step S120, the low battery state control program executes step S140 to provide an indication to the user the controller is in a low battery state.

At step S140, the low battery state control program blinks the indicator LED, for example, 10 times at 0.5 second intervals. Then, the low battery state control program resets the watchdog timer at step S142 and returns to the start of the main control program at step S100.

Figure 47:
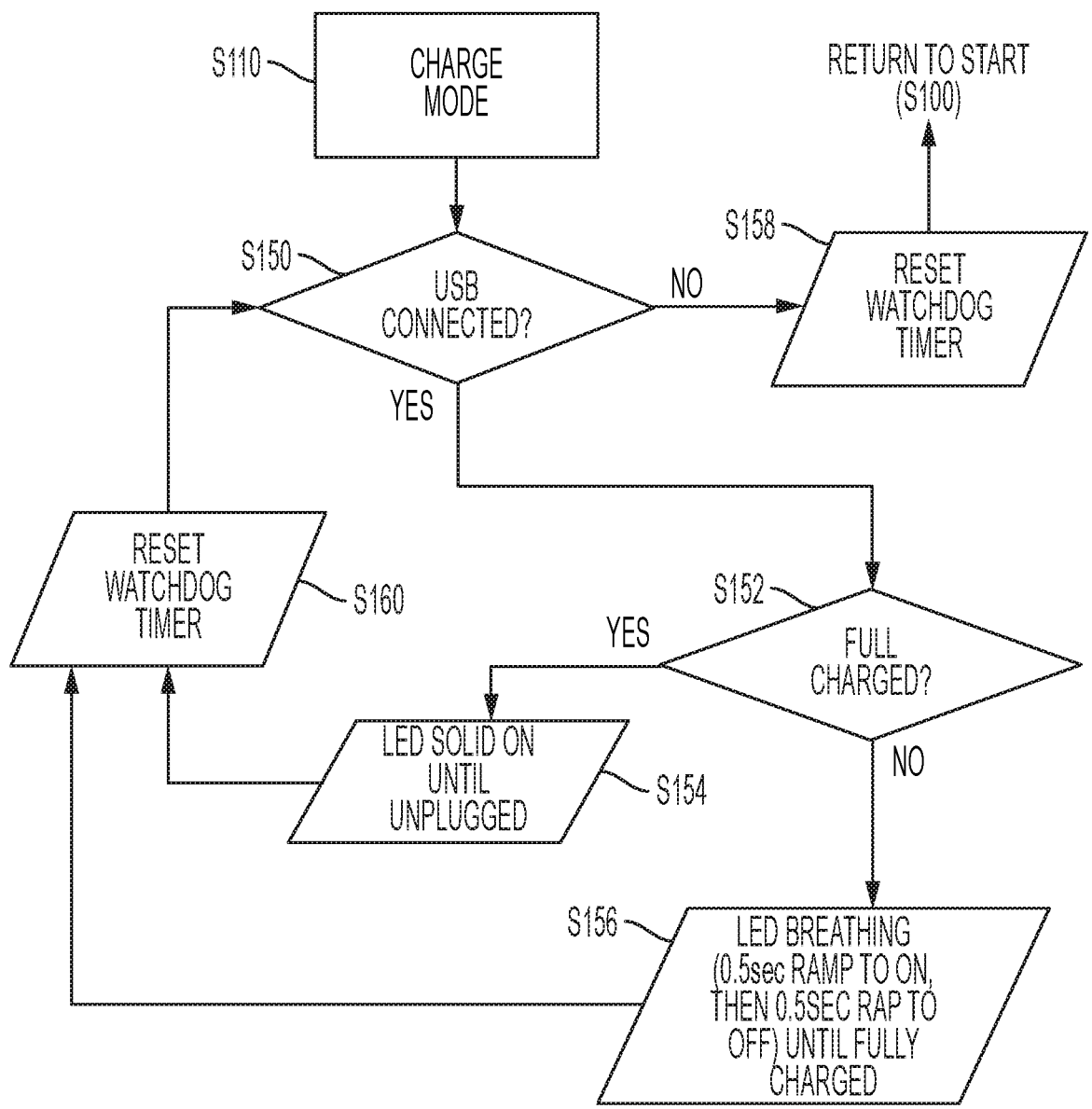
FIG. 47 is a control pod operational flow chart of a controller charging state associated with a radiant energy back/knee bandage pad assembly operatively connected to a control pod, according to an exemplary embodiment of this disclosure.

With reference to FIG. 47, illustrated is a control pod operational flow chart of a controller charging state associated with a radiant energy back/knee bandage pad assembly operatively connected to a control pod, according to an exemplary embodiment of this disclosure.

After entering the controller charging state mode at step S110, the charging state control program executes step S150 to determine if a USB device is operatively connected to the control pod. If a USB device is not operatively connected, the charging state control program resets the watchdog timer at step S152 and returns to the start of the main control program at step S100. If a USB device is operatively connected to the pod controller, the charging state control program executes step S152 to determine if the battery is fully charged.

At step S152, if the battery is determined to be fully charged, the charging state control program performs step S154 to continuously light the indicator LED until the USB device is disconnected from the control pod, at which time the charging state control program resets the watchdog timer at step S160 and returns to step S150 to determine if a USB device is operatively connected. If at step S152, the battery is not fully charged, the charging state control program executes step S156 to charge the battery.

At step S156, the charging state control program charges the battery and activates the indicator LED to indicate the pod controller battery is charging. For example, providing a LED "breathing" indication where the indicator LED is ramped to "ON" and then ramped to "OFF" in a repetitive cycle. Steps S154, S160 and S150 are continuously executed while the battery is charging until the battery is fully charged or the USB device is disconnected from the control pod, at which time the charging state control program returns to the start of the main control program at step S100 after resetting the watchdog timer at step S158.

Figure 48:
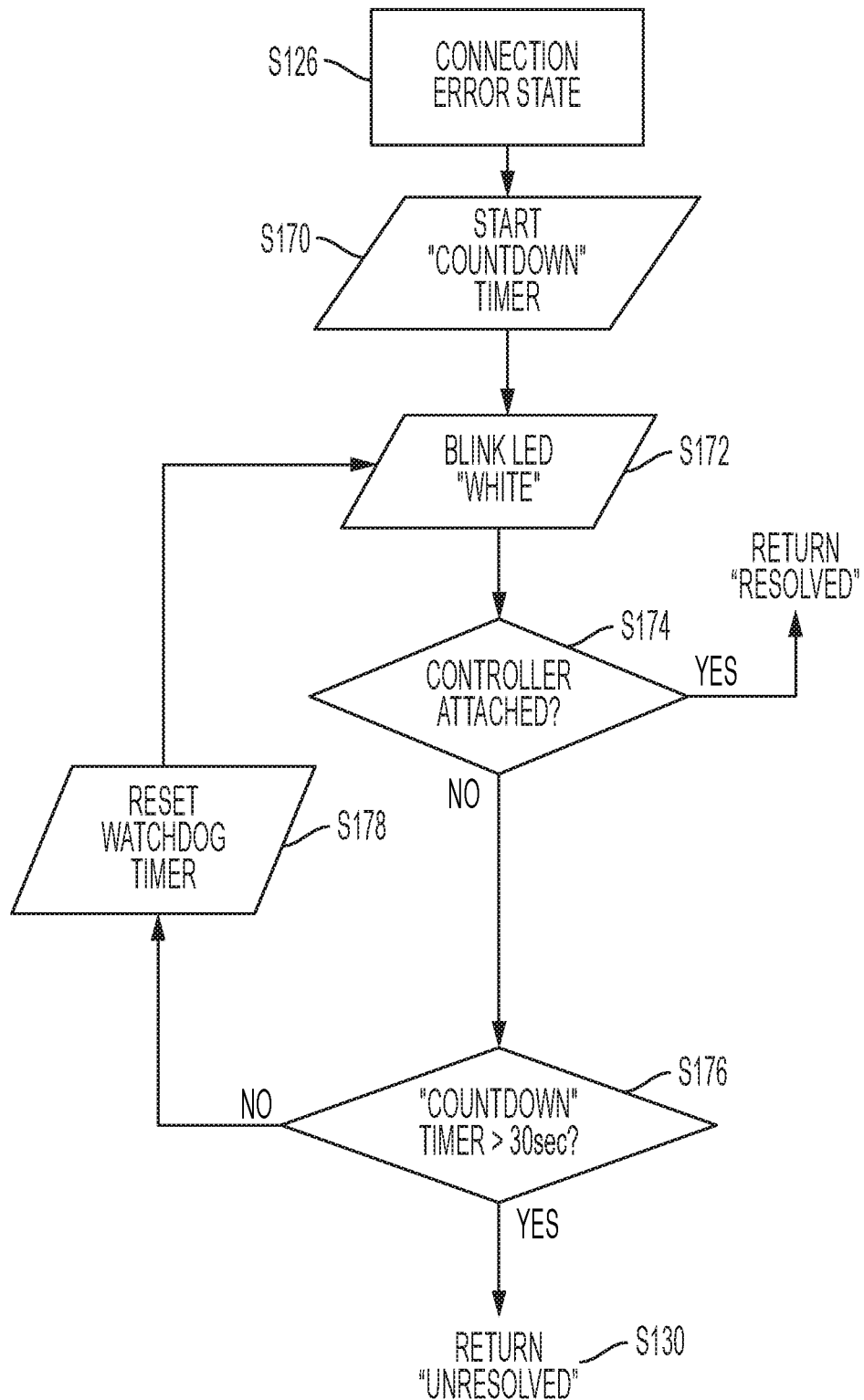
FIG. 48 is a control pod operational flow chart of a controller/bandage connection error state associated with a radiant energy back/knee bandage pad assembly operatively connected to a control pod, according to an exemplary embodiment of this disclosure.

With reference to FIG. 48, illustrated is a control pod operational flow chart of a controller/bandage connection error state associated with a radiant energy back/knee bandage pad assembly operatively connected to a control pod, according to an exemplary embodiment of this disclosure.

After entering the connection error state control program at step S126, the connection error state control program performs step S170 starting a countdown time, then blinks the indicator LED at step S172 and executes a program to resolve the connection error state.

At step S174, if the connection error state control program resolves the pod/controller connection state, the program returns to the main control program and resets the watchdog timer at step S128, then enters dose mode at step S124. If the connection error state control program is unable to resolve before the expiration of the countdown timer at step S176, the program returns to the main control program and resets the watchdog timer at step S130, then returns to the start of the control program at step S100.

During the execution of the connection error state control program to resolve the connection state at step S174, the connection error state control program executes steps S176, S178 and S172 to monitor the countdown time, reset the watchdog timer and blink the indicator LED white as the error connection state is attempted to be resolved.

Figure 49A:
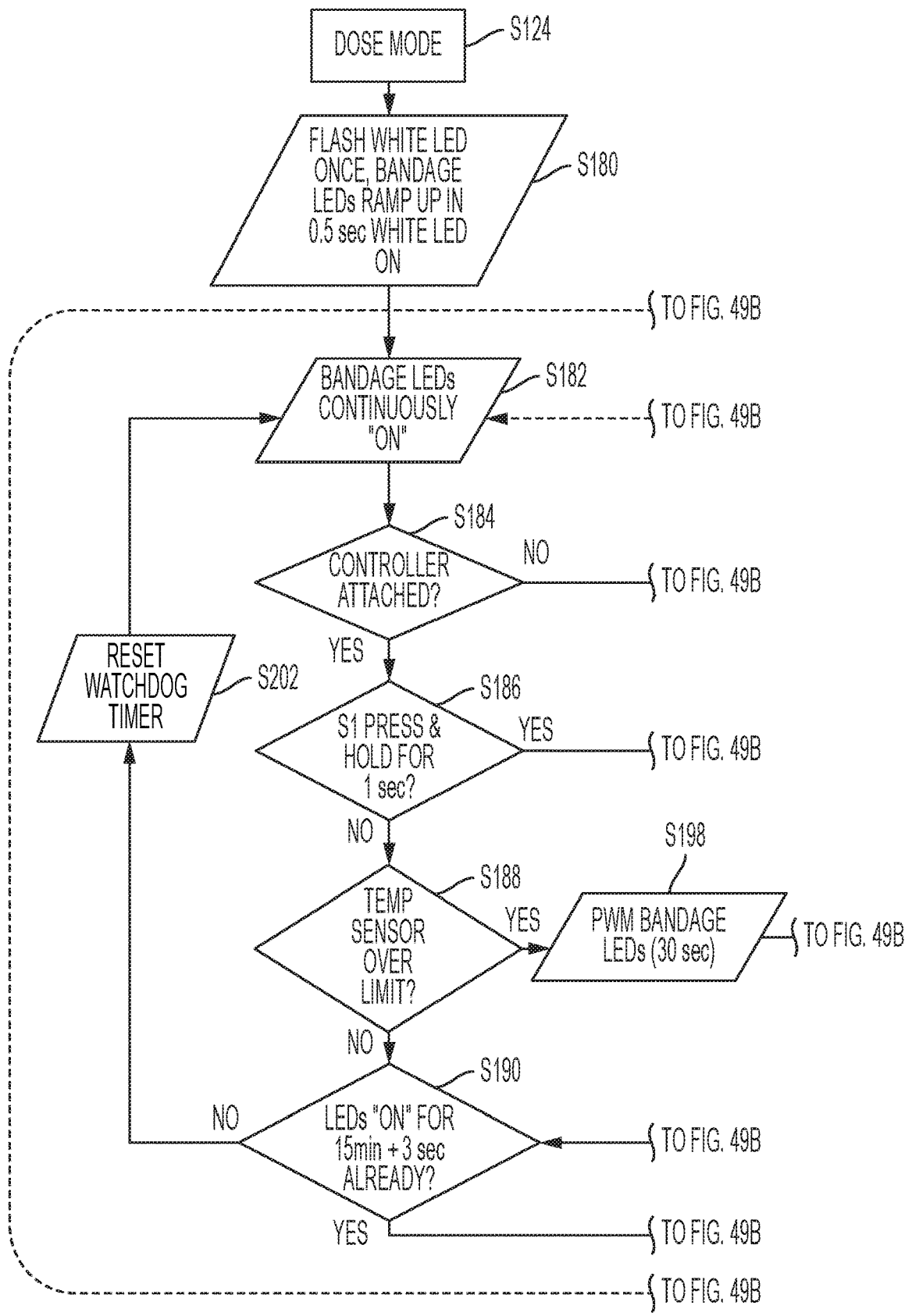
FIGS. 49A and 49B illustrate a control pod operational flow chart of a radiant energy dose mode associated with a radiant energy back/knee bandage pad assembly operatively connected to a control pod, according to an exemplary embodiment of this disclosure.
Figure 49B:
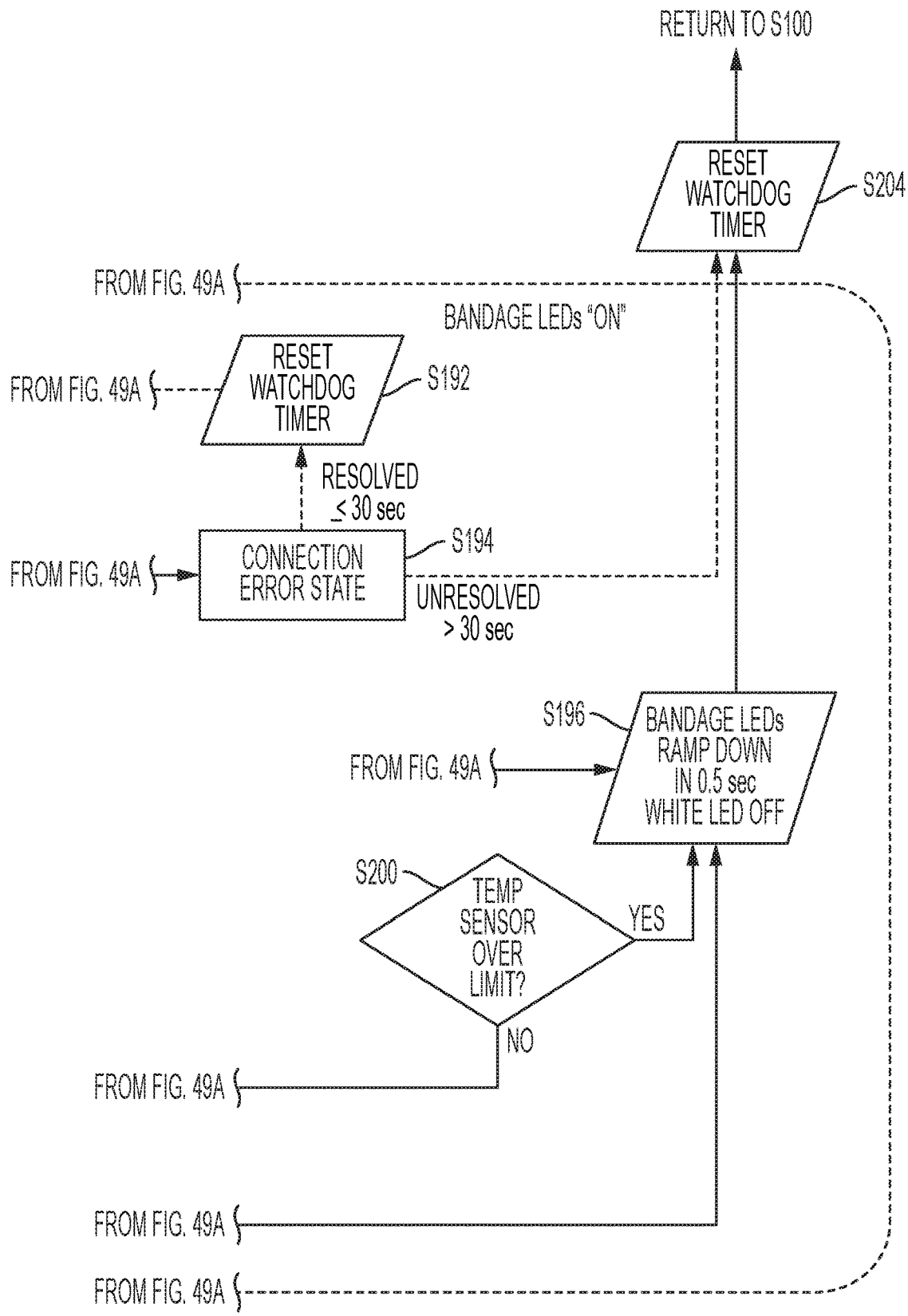

With reference to FIGS. 49A and 49B, illustrated is a control pod operational flow chart of a radiant energy dose mode associated with a radiant energy back/knee bandage pad assembly operatively connected to a control pod, according to an exemplary embodiment of this disclosure.

After entering the dose mode control program at step S124, the dose mode control program executes step S180 to flash the white indicator LED once as the bandage LEDs ramp up to deliver a radiant energy treatment and then the white LED is continuously on during the dosage session.

Next, at step S182, the bandage pad assembly LEDs are controlled to be continuously on. During the dosage delivery, the dose mode control program executes step S184 to determine if the pod controller is operatively connected to the bandage pad assembly, executes step S186 to monitor the user control switch SW1 to terminate the dosage session if switch SW1 is pressed longer than 1 second, executes step S188 to determine if the bandage pad is too hot, i.e., temperature sensor over limit, and determines if the bandage pad assembly LEDs have been turned on for longer than a predetermined period, i.e., approximately 15 minutes, ending the dosage session.

During the execution of radiant energy dosage delivery, if the controller is determined to be operatively disconnected from the bandage pad assembly, the dose mode control program executes step S194 to attempt to resolve the connection error state. If the connection error state is resolved, the watchdog timer is reset S192 and the dose mode control program returns to step S182 to turn on the bandage pad LEDs. If the connection error state is not resolved at step S194, the dose mode control program resets the watchdog timer at step S204 and returns to the start of the main control program at step S100.

During the execution of radiant energy dosage delivery, if the user switch is pressed and held, the dose mode controller executes step S196 to ramp down the bandage LEDs, reset the watchdog timer at step S204 and returns to the start of the main control program at step S100.

During the execution of radiant energy dosage delivery, if at step S188 the dose mode control program determines the temperature sensor is over limit, step S198 is executed for 30 seconds to lower the power to the bandage LEDs, and then step S200 is executed to determine if the temperature is still over limit. If the temperature decreases to an acceptable level, the dose mode control program returns to execute radiant energy dosage delivery. If the temperature remains over limit, the dose mode control program performs step S196 to ramp down the power to the bandage pad LEDs, resets the watchdog timer and returns to the start of the main control program at step S100.

During the execution of radiant energy dosage delivery, if at step S190 the dose mode control program determines the bandage pad LEDs have been turned on for greater than a predetermined period, for example, 15 minutes, the dose mode control program executes step S196 to ramp down the power to the bandage pad LEDs, resets the watchdog timer at step S204 and returns to the start of the main control program at step S100.

Figure 50A:
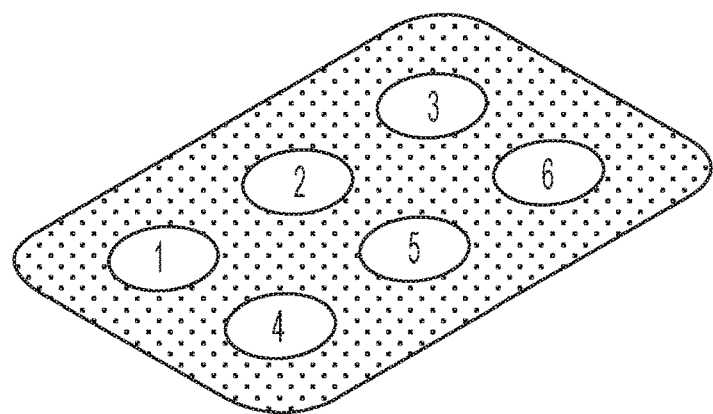
FIGS. 50A-50E include connection state views associated with potential electrical bandage pad controller pod connection configurations.
Figure 50B:
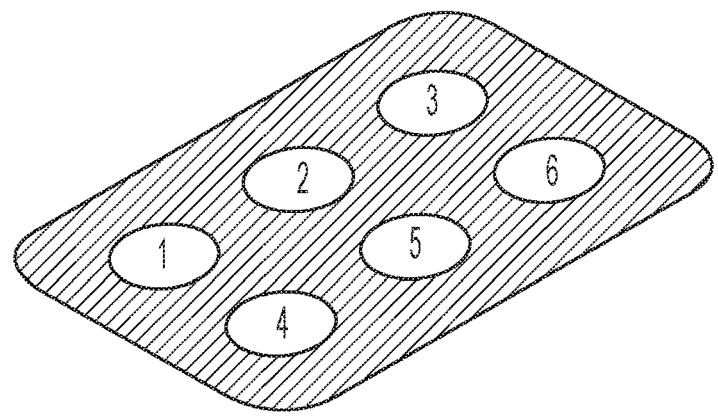
Figure 50D:
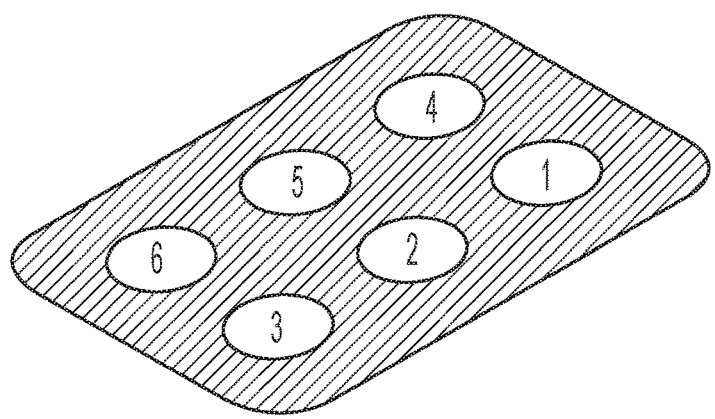
Figure 50C:
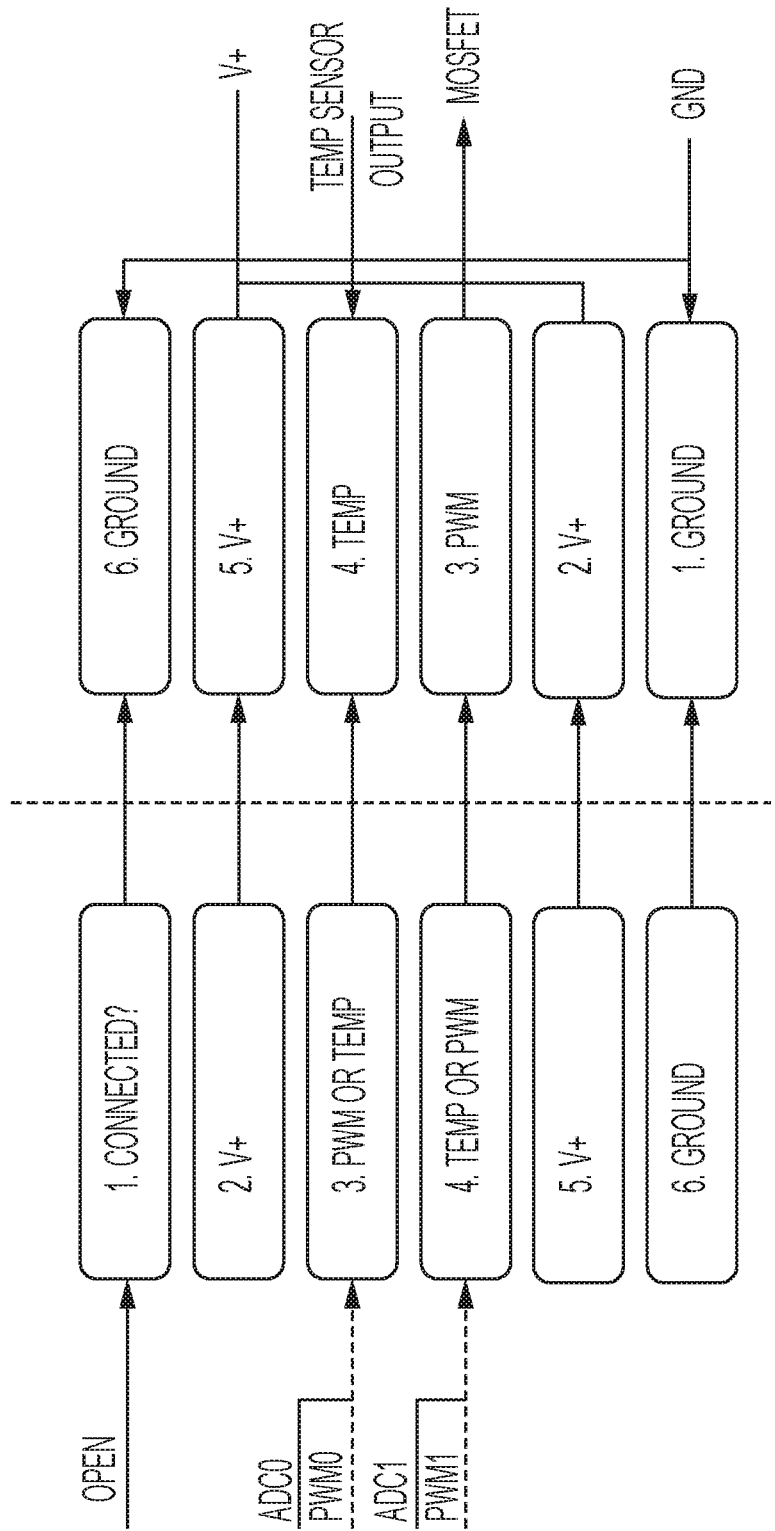
Figure 50E:
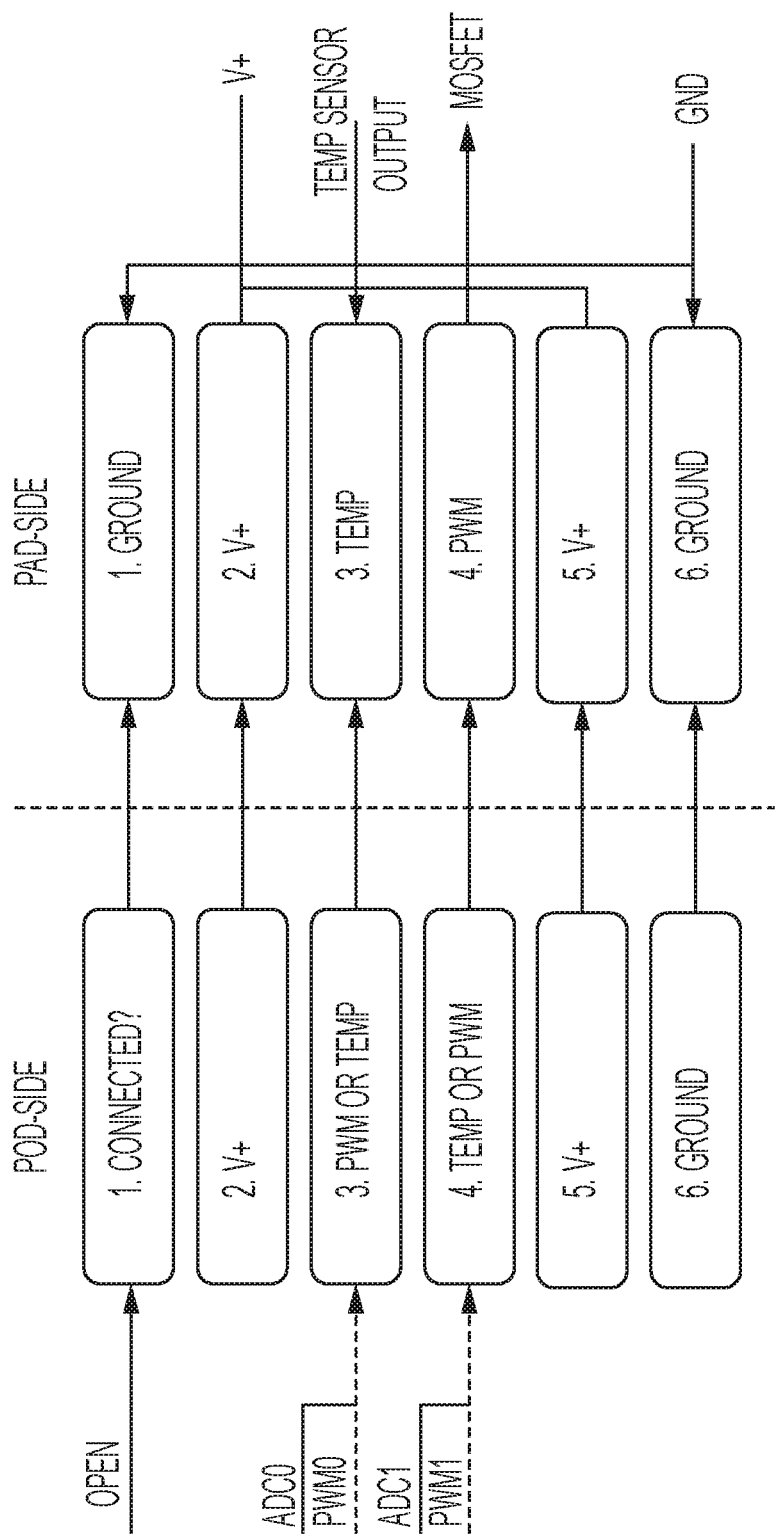

With reference to FIGS. 50A-50E and FIG. 51, illustrated are connection state views associated with potential electrical bandage pad controller pod connection configurations and a control pod operational flow chart of a connection state resolution algorithm, respectively, according to an exemplary embodiment of this disclosure. FIG. 50A is representative of the controller pod-side bandage pad connector; FIG. 50B is representative of a first orientation of the back/knee bandage pad control pod connector; FIG. 50C is an electrical connection state diagram associated with the first orientation of the back/knee pad control pod connector interconnected to the controller pod connector; FIG. 50D is representative of a second orientation, rotated 180 degrees relative to the first orientation, of the back/knee bandage pad control pod connector; and FIG. 50E is an electrical connection state diagram associated with the second orientation of the back/knee pad control pod connector rotated 180 degrees and interconnected to the controller pod connector.

For Pad/Pod orientation detection, the controller IC takes a "poll" of the connections "DUAL1" and "DUAL2." It has two I/O pins for each "DUAL" connection point . . . both a PWM pin (output) and an Analog/Digital Converter (input) . . . but they aren't "assigned" by default. The software will "hot-assign" which pin to use based on the results of the "poll."

The Temp Sensor puts out a "HIGH" voltage while the PWM mosfet gives a "LOW" reading, providing a basis to determine the orientation of the connection.

The "poll" stores values from the DUAL1 and DUAL2 pins, and finds out which pin is "LOW." The "LOW" signal is assigned to a PWM pin, and the "HIGH" signal is assigned to an ADC pin, thereby determining the connection state.

For Ground Connection Determination via only the hardware, the "Connected?" pin looks for a ground-loop to trigger the Q1 mosfet inside the Controller Pod. If the ground-loop is closed (through the bandage), the Q1 mosfet sends the "enable" signal to the load switch U3, and everything can run. If the ground-loop is open, load switch U3 is not "enabled" and won't open.

Figure 51:
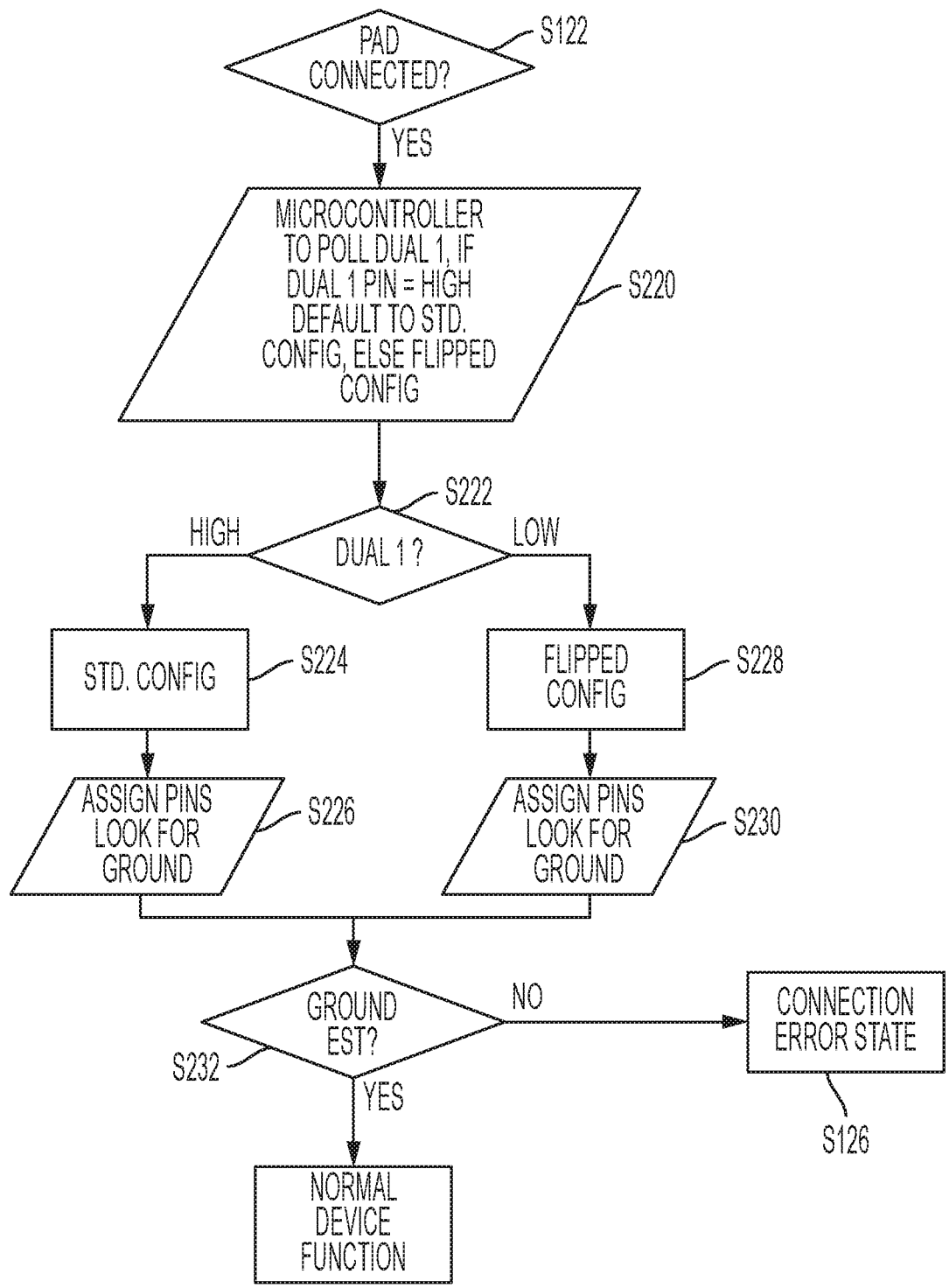
FIG. 51 is a control pod operational flow chart of a connection state resolution algorithm, according to an exemplary embodiment of this disclosure.

As shown in the control pod operational flow chart illustrated in FIG. 51, after entering the Pad/Connected?/Controller Attached? mode control program at step S122, the control program executes steps S220 and S222 to poll the dual functioning outputs.

At step S220 and step S222, if the control program determines Dual 1 pin is high, the control program defaults to a standard, 1st orientation configuration S224, otherwise the control program flips to 2nd orientation configuration S228.

At steps S226 and S230, the dual functioning connections/pins are assigned the appropriate functions, i.e., ADC input or PWM output, and a ground detection determination is performed.

If at step S232 the control program determines a ground connection is not established, the control program proceeds to connection error state mode S126. If the control program determines a ground connection is established, the control program proceeds to normal device function.

Figure 52:
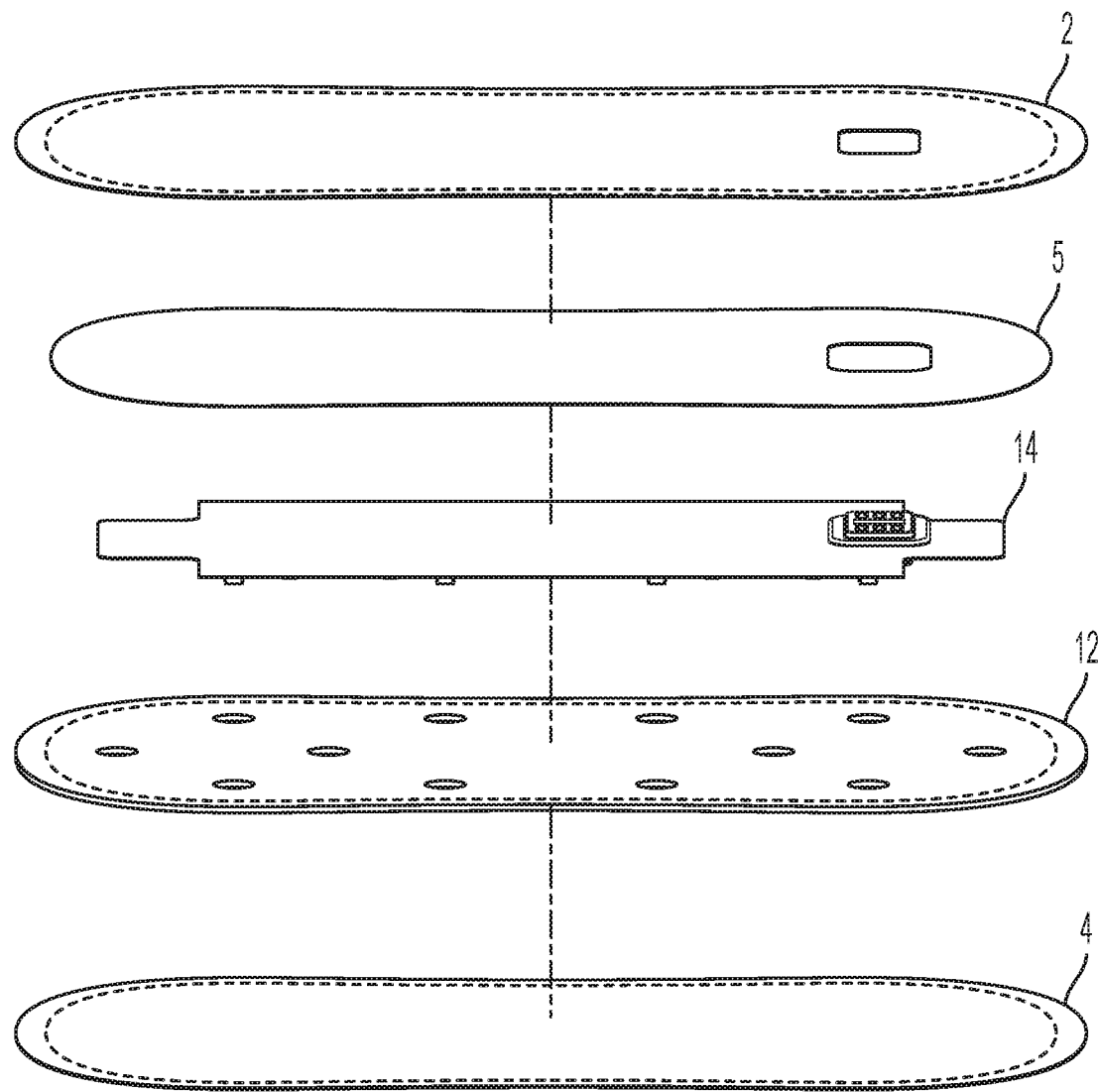
FIG. 52 is an assembly view of a radiant energy back bandage pad assembly, according to an exemplary embodiment of this disclosure, including an opaque PVC PCBA cover layer 5 located between the top layer 2 and the flexible PCBA 14, and a foam pad layer 12 with LED aligned apertures located between the flexible PCBA 14 and the transparent bottom layer 4.

With reference to FIG. 52, illustrated is an assembly view of a radiant energy back bandage pad assembly, according to an exemplary embodiment of this disclosure, including an opaque PVC PCBA cover layer 5 located between the top layer 2 and the flexible PCBA 14, and a foam pad layer 12 with LED aligned apertures located between the flexible PCBA 14 and the transparent bottom layer 4.

Figure 53:
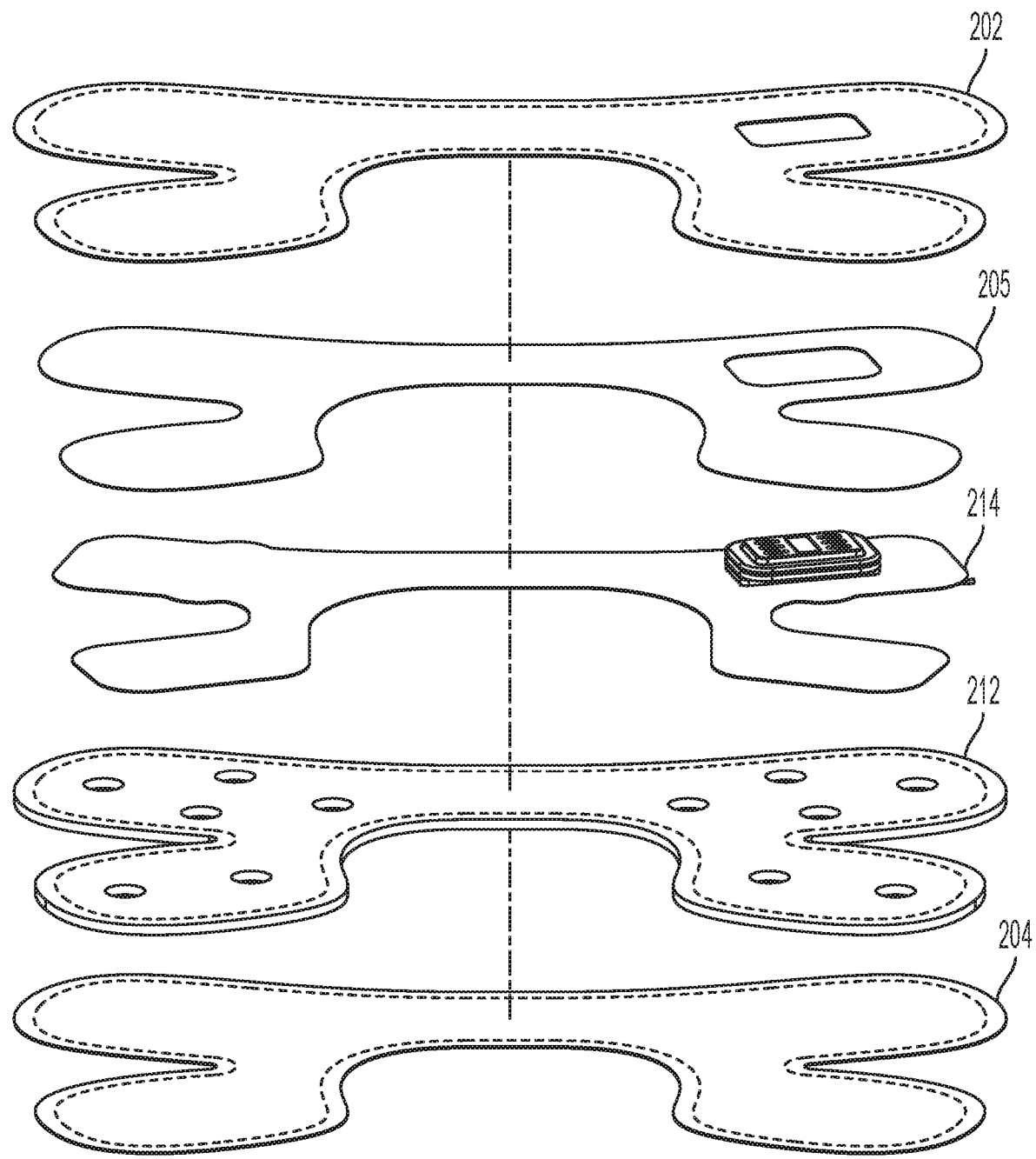
FIG. 53 is an assembly view of a radiant energy knee bandage pad assembly, according to another exemplary embodiment of this disclosure, including an opaque PVC PCBA cover layer 205 located between the top layer 202 and the flexible PCBA 214, and a foam pad layer 212 with LED aligned apertures located between the flexible PCBA 214 and the transparent bottom layer 204.3

With reference to FIG. 53, illustrated is an assembly view of a radiant energy knee bandage pad assembly, according to another exemplary embodiment of this disclosure, including an opaque PVC PCBA cover layer 205 located between the top layer 202 and the flexible PCBA 214, and a foam pad layer 212 with LED aligned apertures located between the flexible PCBA 214 and the transparent bottom layer 204.

Figure 54:
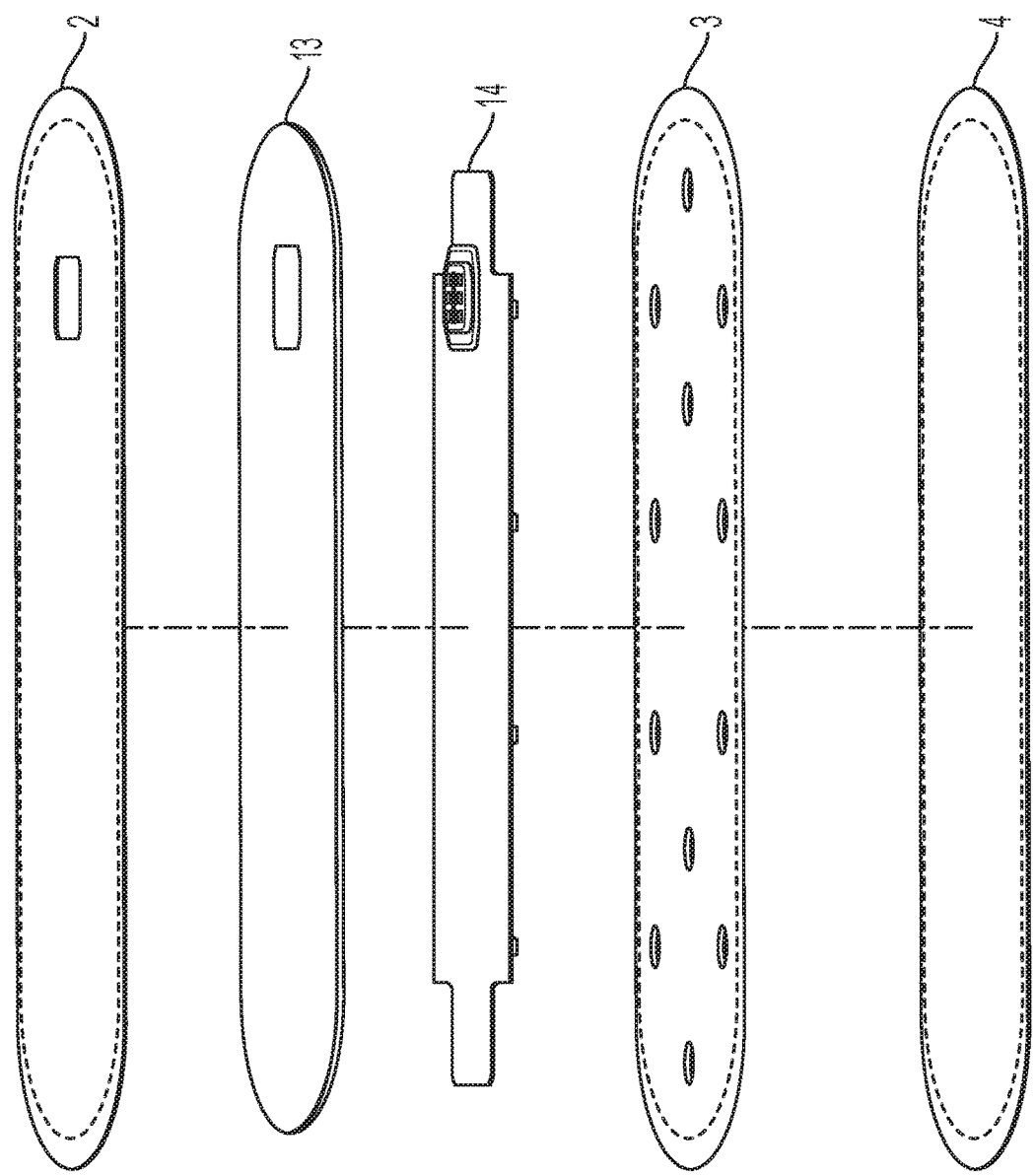
FIG. 54 is an assembly view of a radiant energy back bandage pad assembly, according to an exemplary embodiment of this disclosure, including a foam pad 13, without apertures, located between the top layer 2 and the flexible PCBA 14, and a flexible PCBA cover 3 with LED aligned apertures located between the flexible PCBA 14 and the transparent bottom layer 4.

With reference to FIG. 54, illustrated is an assembly view of a radiant energy back bandage pad assembly, according to an exemplary embodiment of this disclosure, including a foam pad 13, without apertures, located between the top layer 2 and the flexible PCBA 14, and a flexible PCBA cover 3 with LED aligned apertures located between the flexible PCBA 14 and the transparent bottom layer 4.

Figure 55:
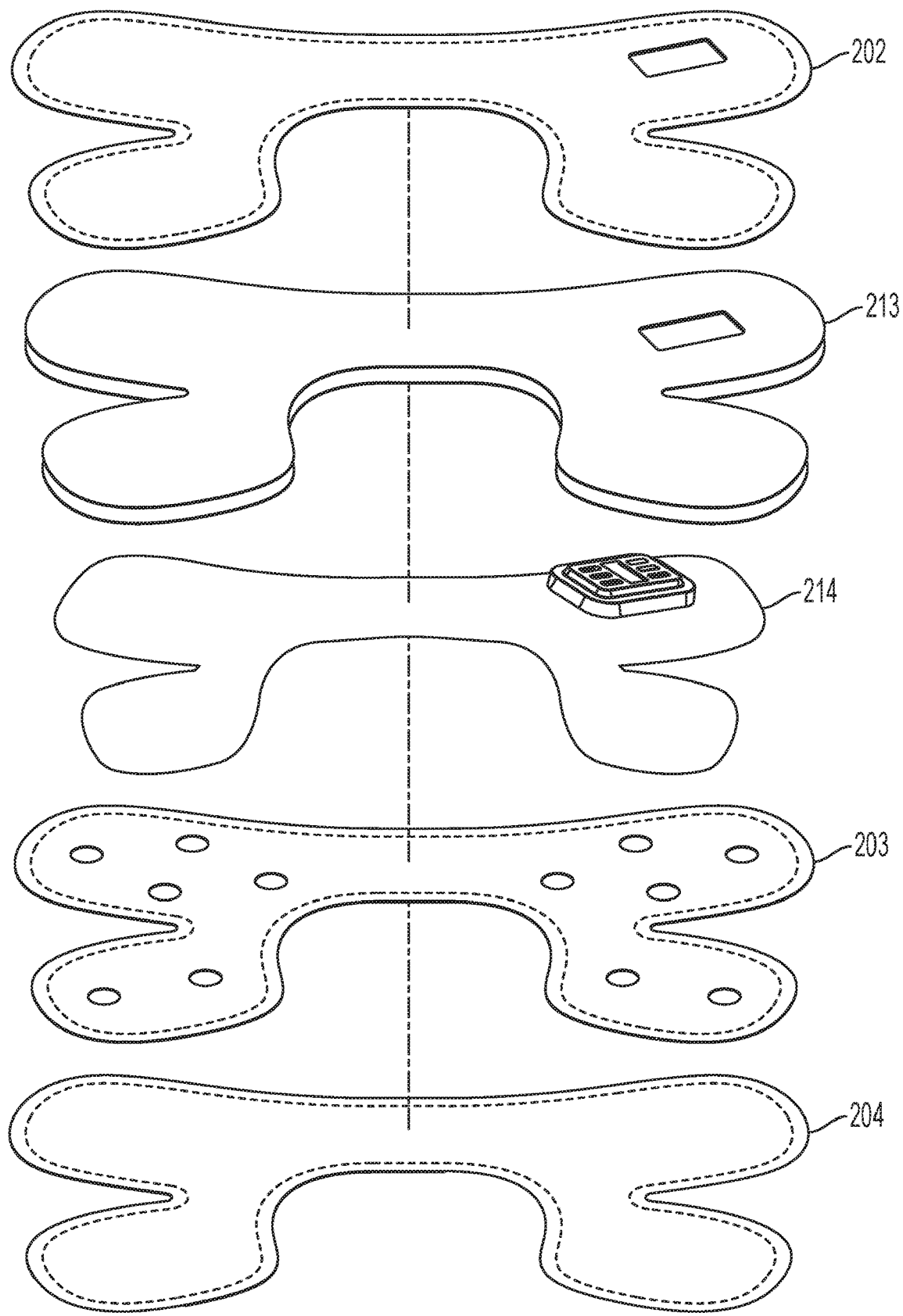
FIG. 55 is an assembly view of a radiant energy knee bandage pad assembly, according to another exemplary embodiment of this disclosure, including a foam pad 213, without apertures, located between the top layer 202 and the flexible PCBA 214, and a flexible PCBA cover 203 with LED aligned apertures located between the flexible PCBA 214 and the transparent bottom layer 204.

With reference to FIG. 55, illustrated is an assembly view of a radiant energy knee bandage pad assembly, according to another exemplary embodiment of this disclosure, including a foam pad 213, without apertures, located between the top layer 202 and the flexible PCBA 214, and a flexible PCBA cover 203 with LED aligned apertures located between the flexible PCBA 214 and the transparent bottom layer 204.

Figure 56:
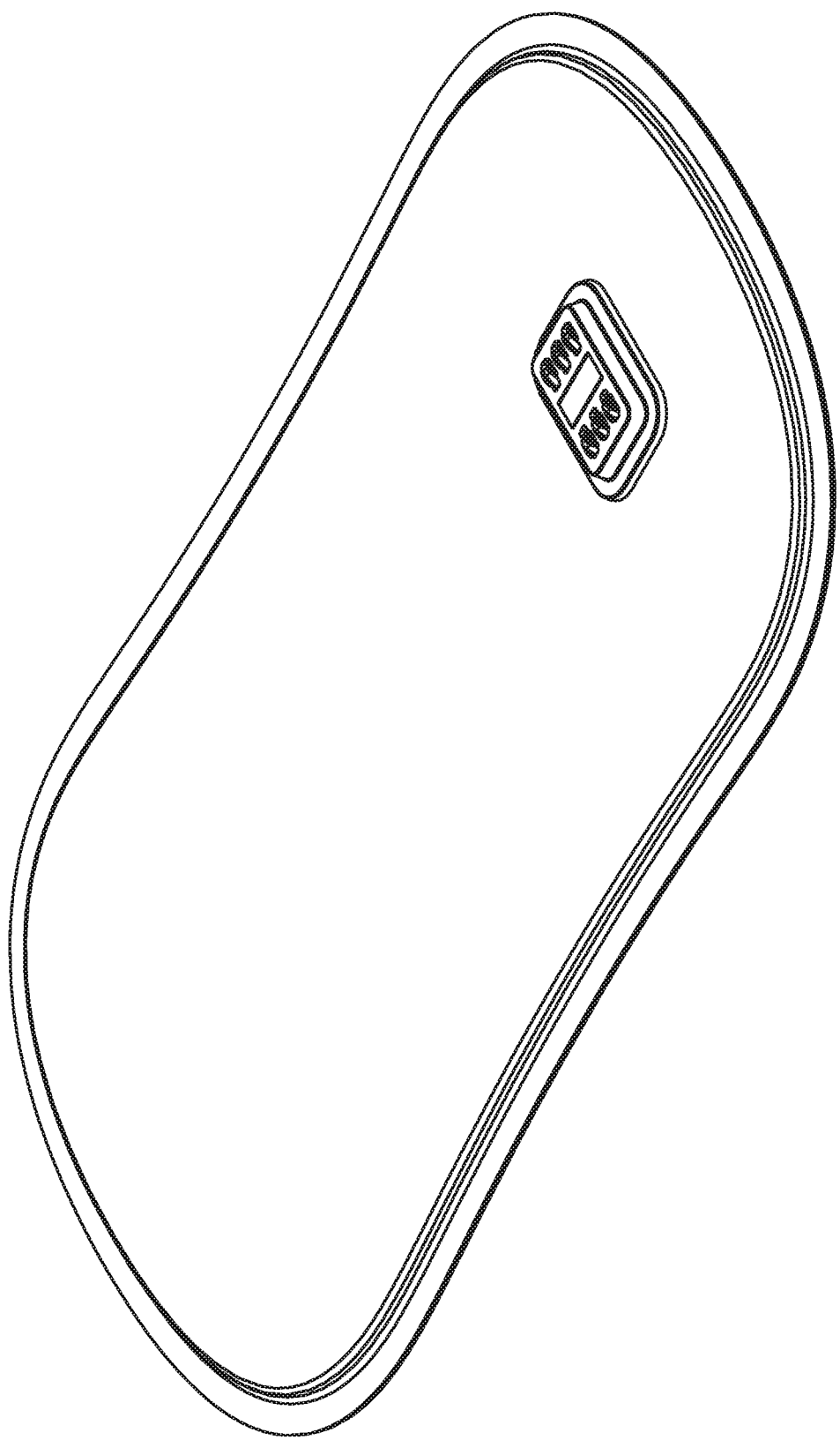
FIG. 56 is a perspective view of a radiant energy back bandage pad assembly according to an exemplary embodiment of this disclosure.
Figure 57B:
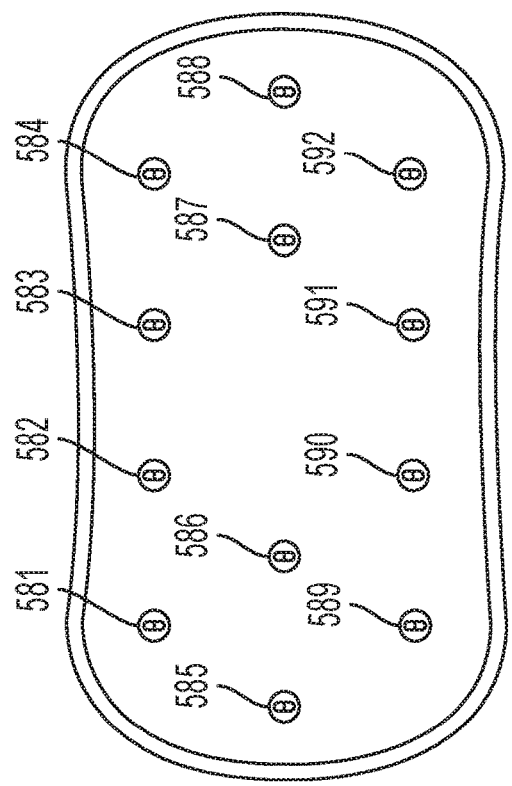
FIGS. 57A, 57B, 57C and 57D include a top view, bottom view, side view and end view, respectively, of the radiant energy back bandage pad assembly shown in FIG. 56.
Figure 57C:
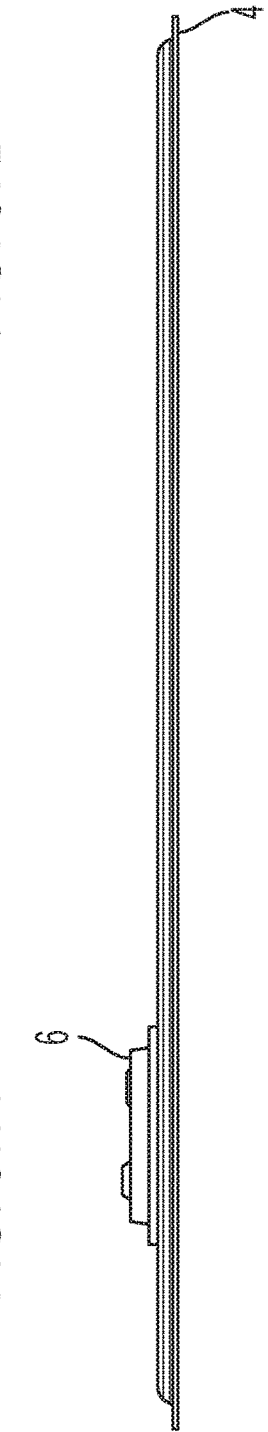
Figure 57D:
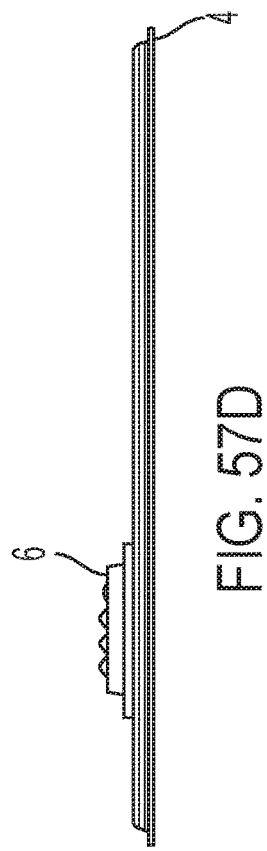
Figure 57A:
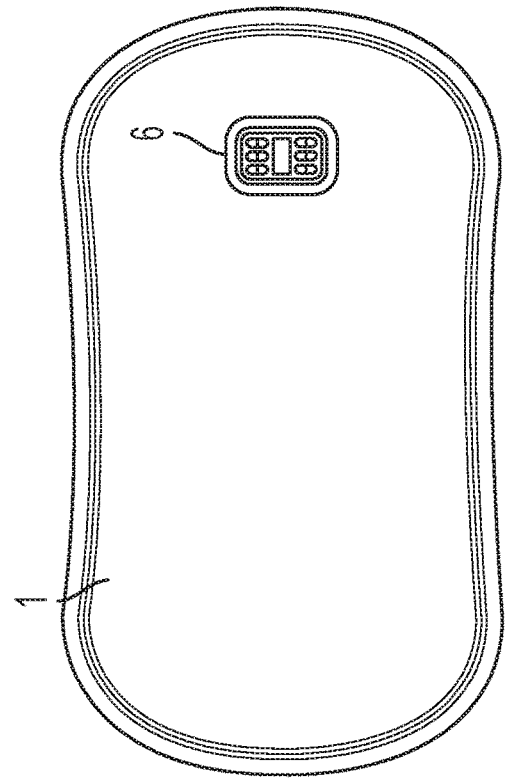

With reference to FIG. 56, illustrated is a perspective view of a radiant energy back bandage pad assembly according to an exemplary embodiment of this disclosure.

With reference to FIGS. 57A, 57B, 57C and 57D, illustrated are a top view, bottom view, side view and end view, respectively, of the radiant energy back bandage pad assembly shown in FIG. 56.

Figure 58:
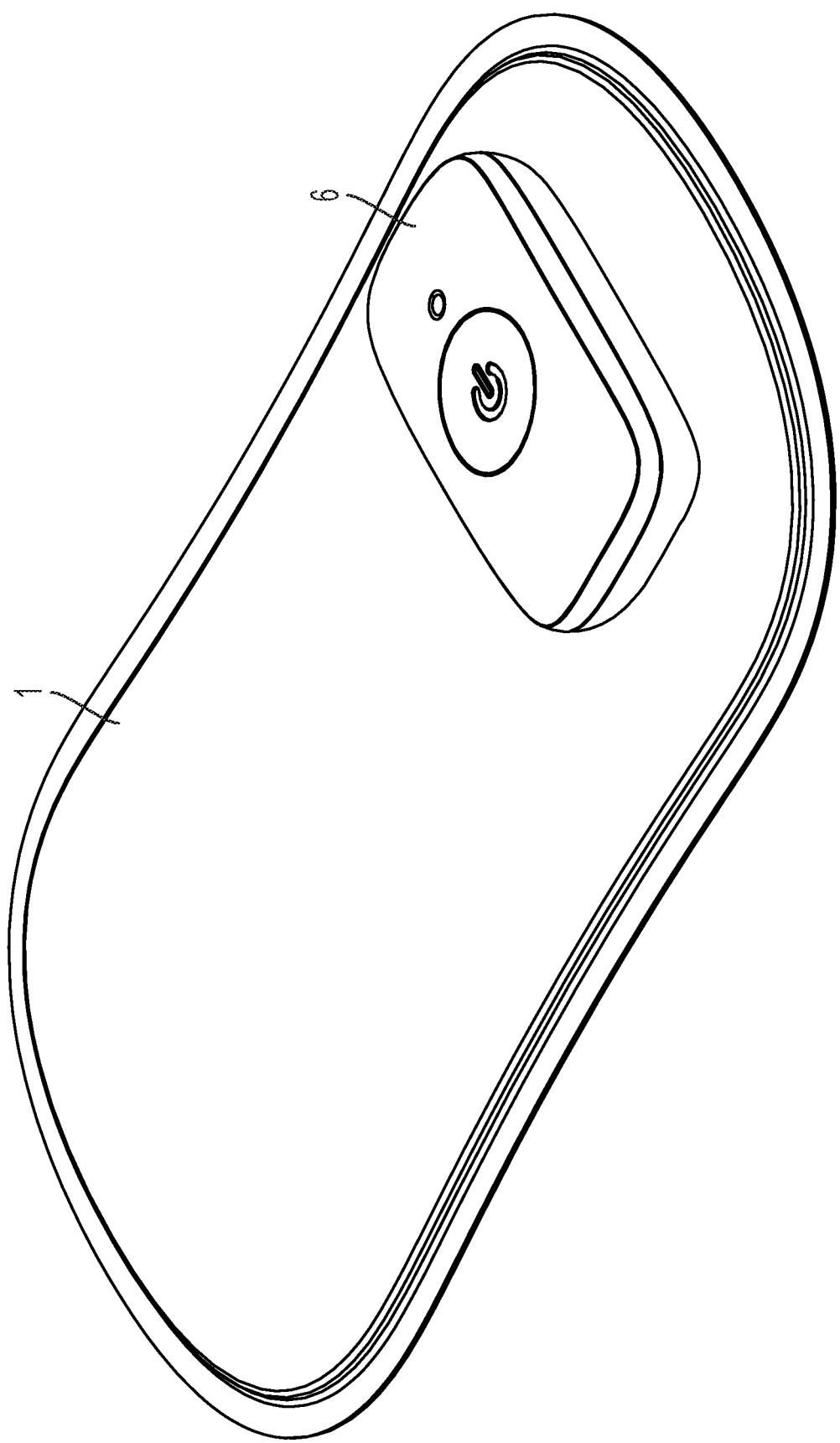
FIG. 58 is a perspective view of a radiant energy back bandage pad assembly including an operatively connected control pod according to an exemplary embodiment of this disclosure.

With reference to FIG. 58, illustrated is a perspective view of a radiant energy back bandage pad assembly including an operatively connected control pod according to an exemplary embodiment of this disclosure.

With reference to FIGS. 59A, 59B, 59C and 59D, illustrated are a top view, bottom view, side view and end view, respectively, of the radiant energy back bandage assembly including an operatively connected control pod shown in FIG. 58.

Figure 60:
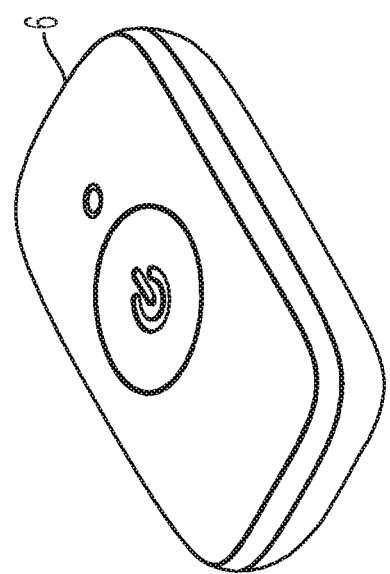
FIG. 60 is a perspective view of a radiant energy back/knee bandage pad control pod according to an exemplary embodiment of this disclosure.

With reference to FIG. 60, illustrated is a perspective view of a radiant energy back/knee bandage pad control pod according to an exemplary embodiment of this disclosure.

Figure 61C:
FIGS. 61A, 61B and 61C include a top view, bottom view and side view, respectively, of the control pod shown in FIG. 60.
Figure 61B:
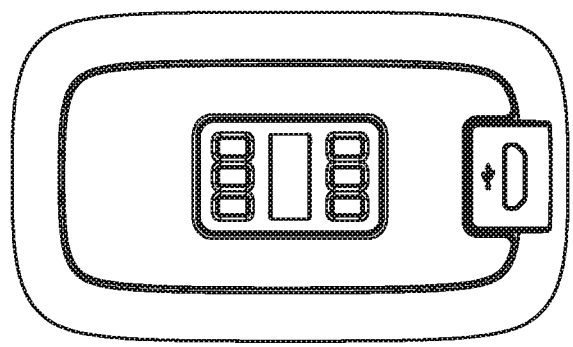
Figure 61A:
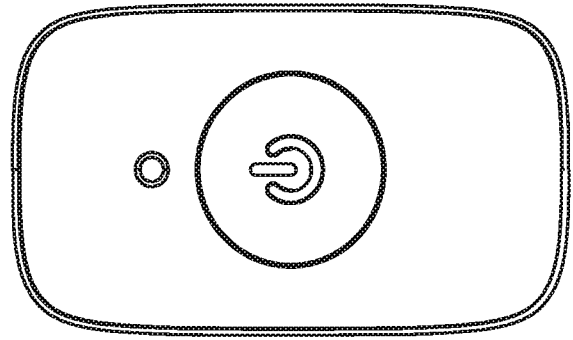

With reference to FIGS. 61A, 61B and 61C, illustrated are a top view, bottom view and side view, respectively, of the control pod shown in FIG. 60.

Figure 62:
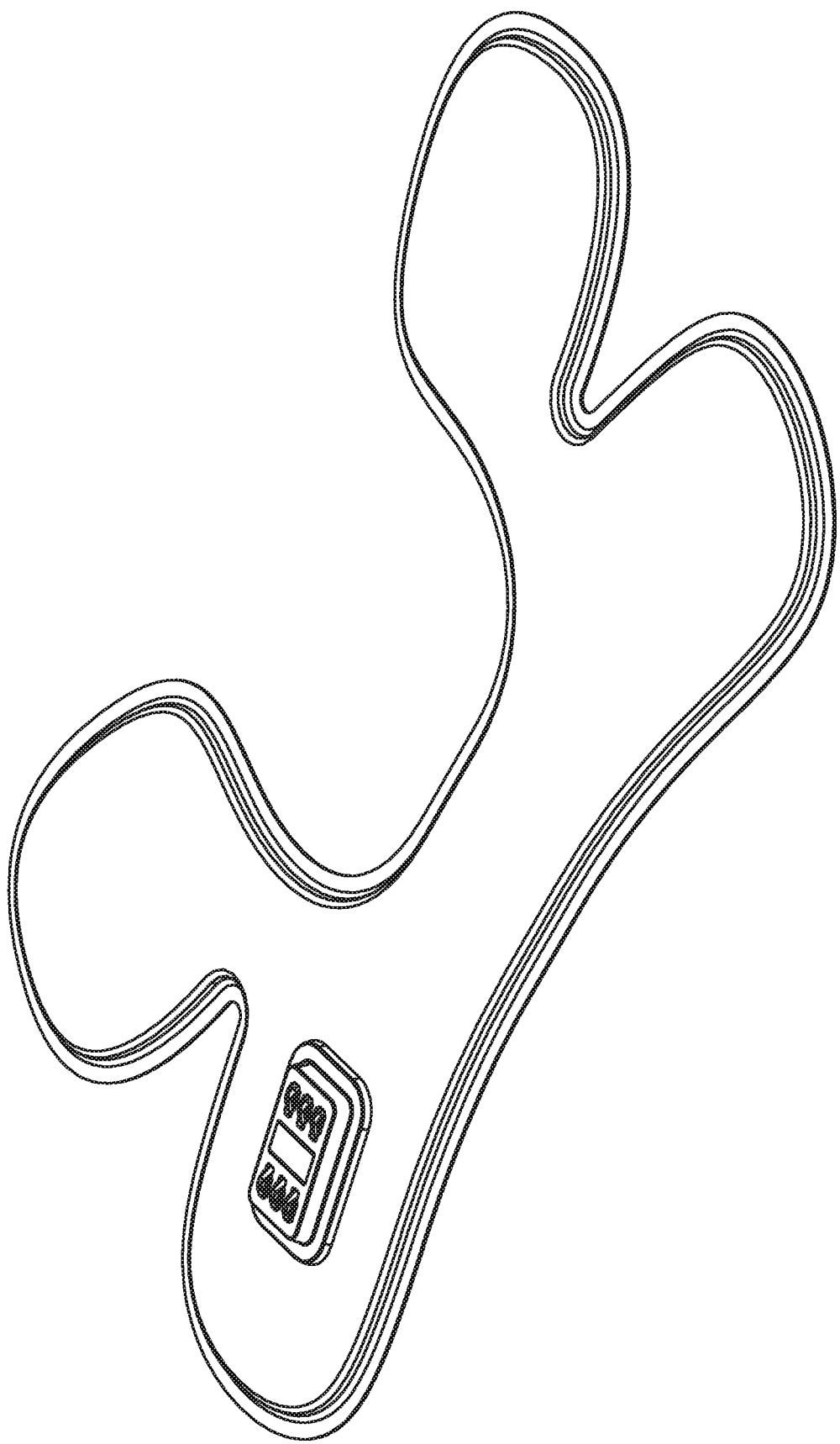
FIG. 62 is a perspective view of a radiant energy knee bandage pad assembly according to an exemplary embodiment of this disclosure.
Figure 63B:
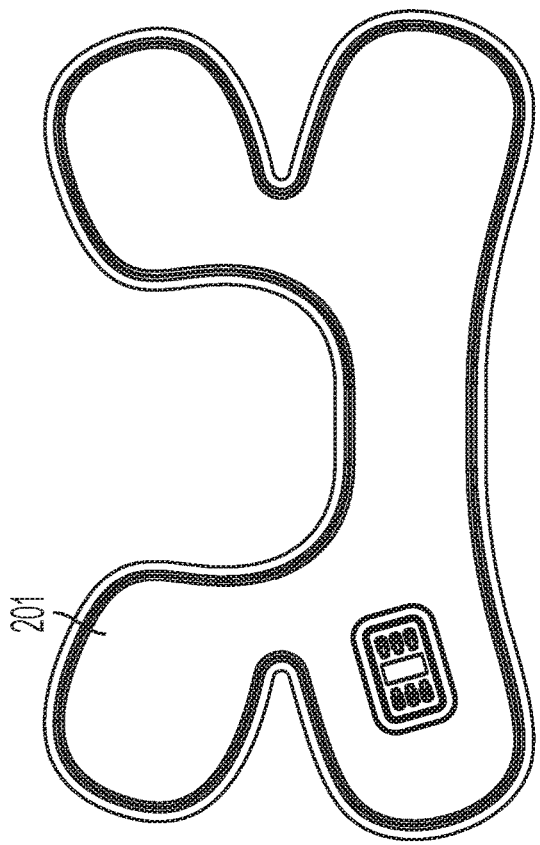
FIGS. 63A, 63B, 63C and 63D include a top view, bottom view, side view and end view, respectively, of the radiant energy knee bandage and assembly shown in FIG. 62.
Figure 63A:
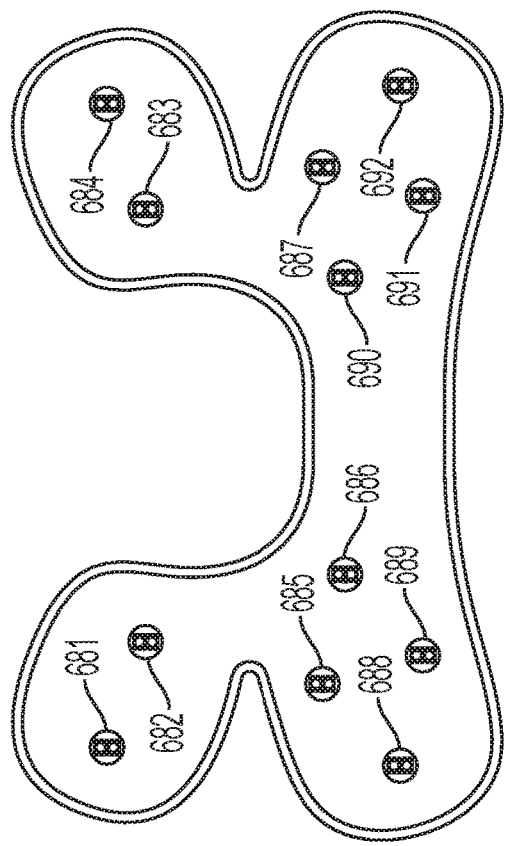
Figure 63C:
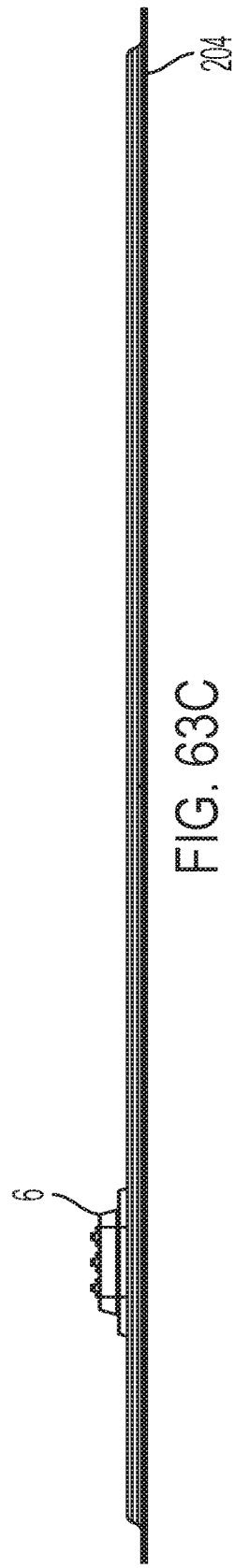
Figure 63D:
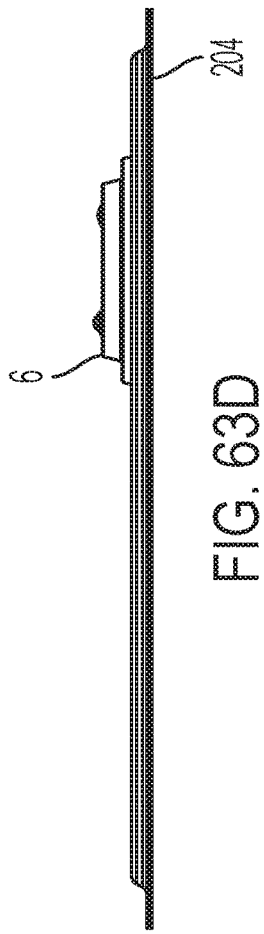

With reference to FIG. 62, illustrated is a perspective view of a radiant energy knee bandage pad assembly according to an exemplary embodiment of this disclosure.

With reference to FIGS. 63A, 63B, 63C and 63D, illustrated are a top view, bottom view, side view and end view, respectively, of the radiant energy knee bandage and assembly shown in FIG. 62.

Figure 64:
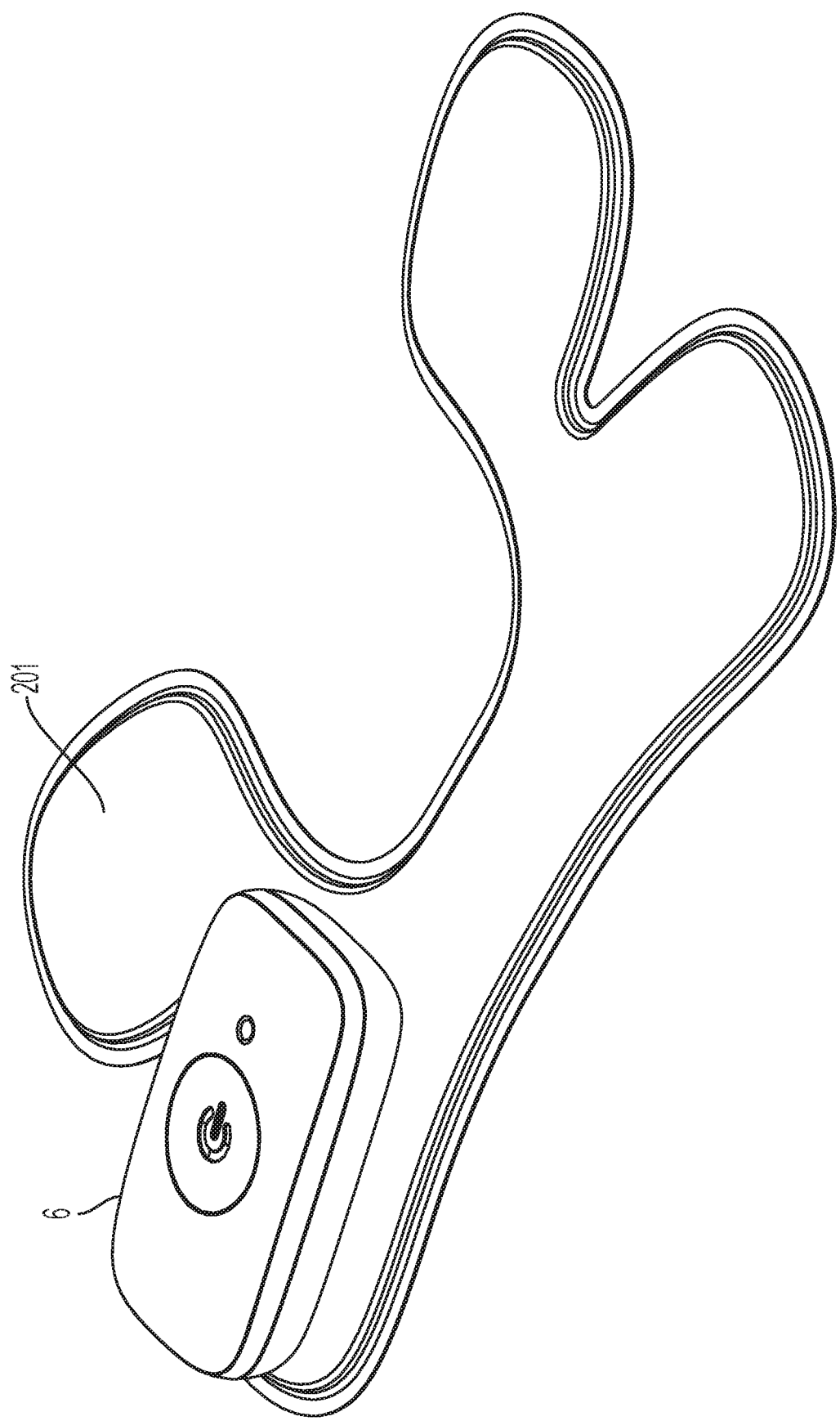
FIG. 64 is a perspective view of a radiant energy knee bandage pad assembly including an operatively connected control pod according to an exemplary embodiment of this disclosure.

With reference to FIG. 64, illustrated is a perspective view of a radiant energy knee bandage pad assembly including an operatively connected control pod according to an exemplary embodiment of this disclosure.

With reference to FIGS. 65A, 65B, 65C and 65D, illustrated are a top view, bottom view, side view and end view, respectively, of the knee bandage pad assembly shown in FIG. 64.

Figure 66:
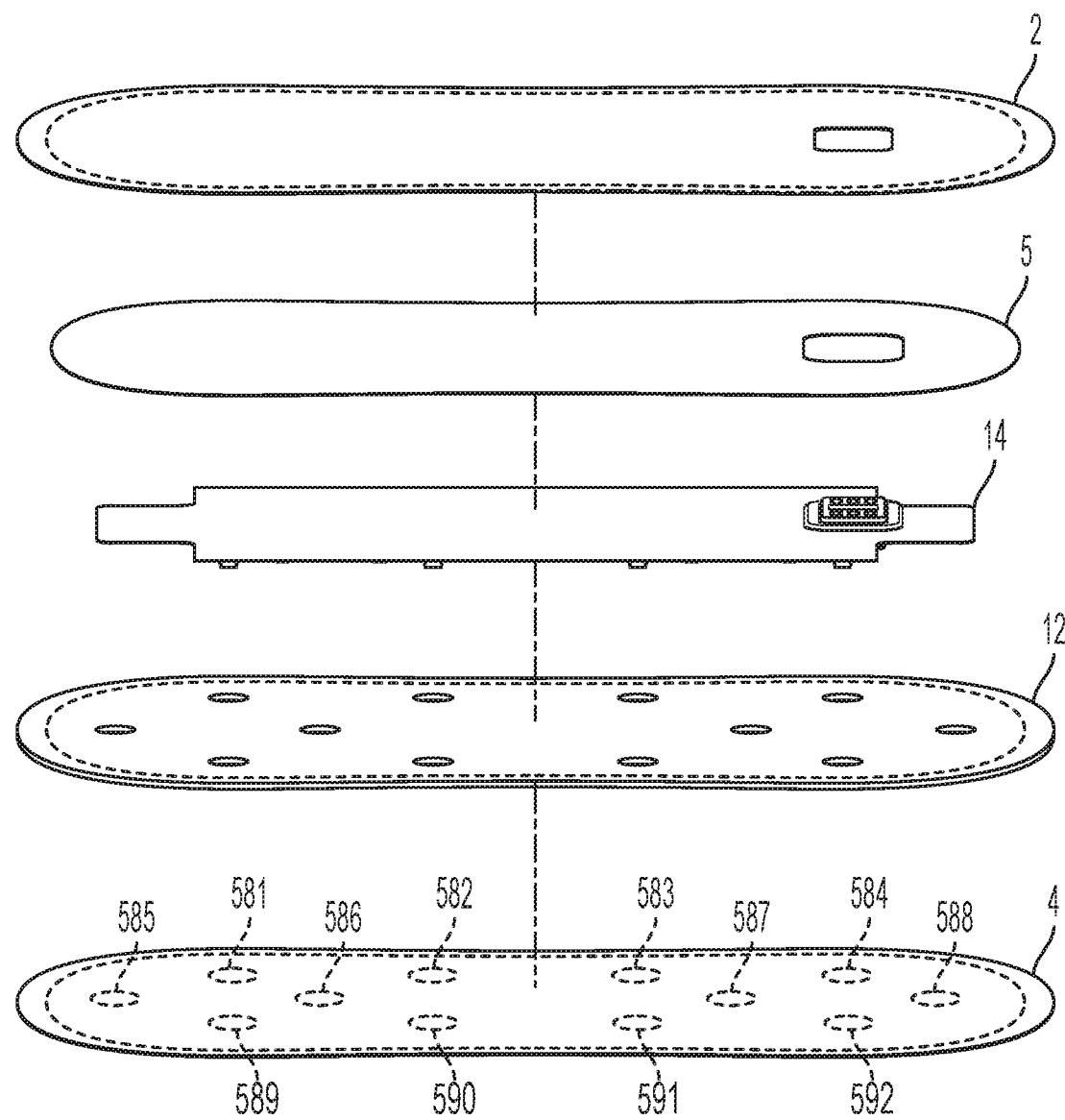
FIG. 66 is an assembly view of a radiant energy back bandage pad assembly, according to an exemplary embodiment of this disclosure, including an opaque DUC PCBA cover layer 5 located between the top layer 2 and the flexible PCBA 14, and a foam pad layer 12 with LED aligned apertures located between the flexible PCBA 14 and a bottom layer 4 including radiant energy communications areas 581-592 produced on a clear transparent PVC layer with a white matte surface printed on the clear transparent PVC layers in areas of the bottom surface not including the radiant energy communication areas 581-592.

With reference to FIG. 66, illustrated is an assembly view of a radiant energy back bandage pad assembly, according to an exemplary embodiment of this disclosure, including an opaque PVC PCBA cover layer 5 located between the top layer 2 and the flexible PCBA 14, and a foam pad layer 12 with LED aligned apertures located between the flexible PCBA 14 and a bottom layer 4 including radiant energy communications areas 581-592 produced on a clear transparent PVC layer with a white matte surface printed on the clear transparent PVC layers in areas of the bottom surface not including the radiant energy communication areas 581-592.

Figure 67:
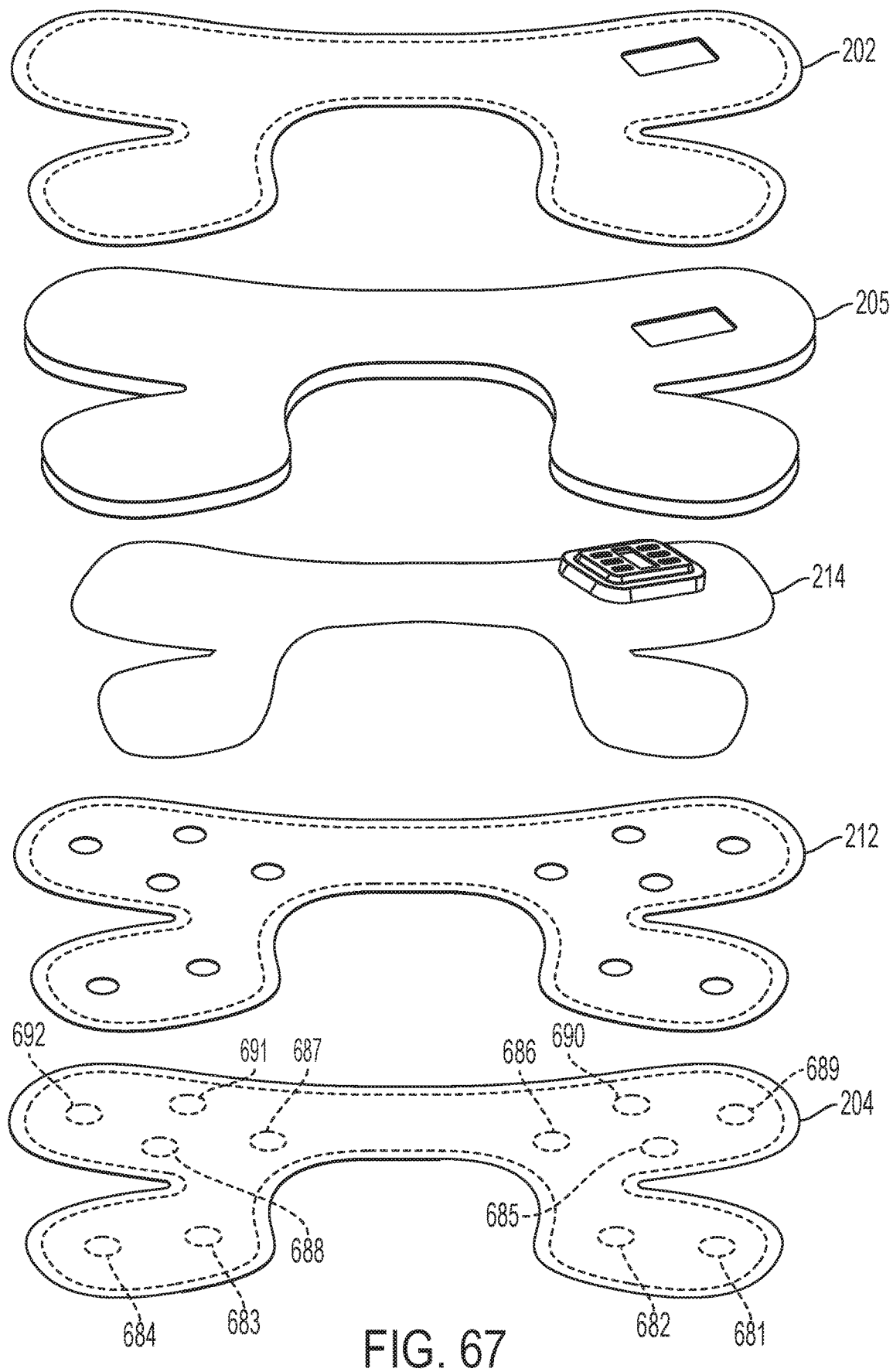
FIG. 67 is an assembly view of a radiant energy knee bandage pad assembly, according to an exemplary embodiment of this disclosure, including an opaque PVC PCBA cover layer 205 located between the top layer 202 and the flexible PCBA 214, and a foam pad layer 212. With LED aligned apertures located between the flexible PCBA 14, and a foam pad layer 212 with LED aligned apertures located between the flexible PCBA 214 and a bottom layer 4 including radiant energy communication areas 681-692 produced on a clear transparent PVC layer with a white matte surface printed on the clear transparent PVC layer in areas of the bottom surface not including the radiant energy communication areas 681-692.

With reference to FIG. 67, illustrated is an assembly view of a radiant energy knee bandage pad assembly, according to an exemplary embodiment of this disclosure, including an opaque PVC PCBA cover layer 205 located between the top layer 202 and the flexible PCBA 214, and a foam pad layer 212 with LED aligned apertures located between the flexible PCBA 14, and a foam pad layer 212 with LED aligned apertures located between the flexible PCBA 214 and a bottom layer 4 including radiant energy communication areas 681-692 produced on a clear transparent PVC layer with a white matte surface printed on the clear transparent PVC layer in areas of the bottom surface not including the radiant energy communication areas 681-692.

Figure 68:
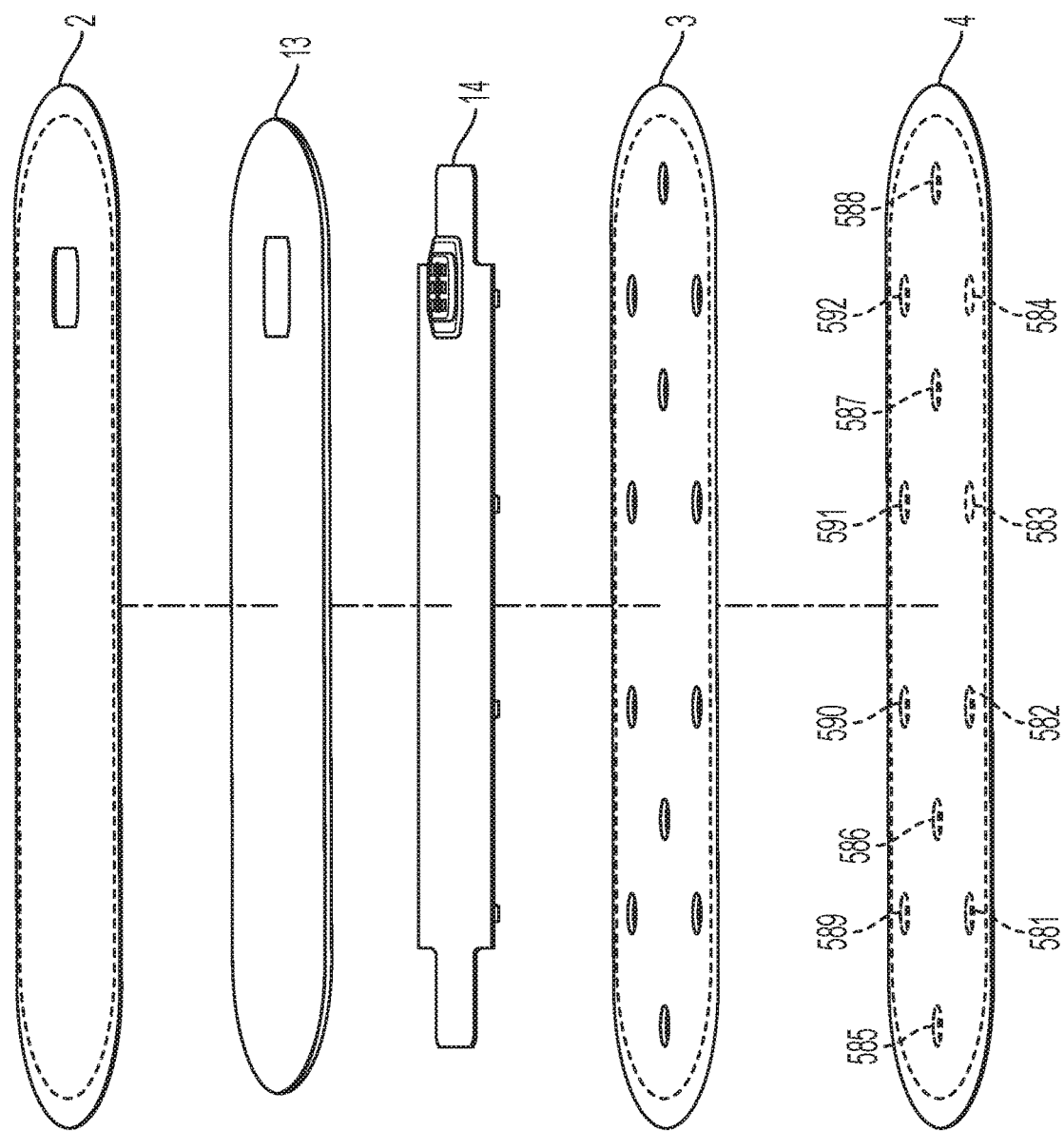
FIG. 68 is an assembly view of a radiant energy back bandage pad assembly, according to an exemplary embodiment of this disclosure, including a foam pad 13, without apertures, located between the top layer 2 and the flexible PCBA 14, and a flexible PCBA cover 3 with LED aligned apertures located between the flexible PCBA 14 and a bottom layer 4 including radiant energy communication areas 581-592 produced on a clear transparent PVC layer with a white matte surface printed on the clear transparent PVC layer on areas of the bottom surface not including the radiant energy communication areas 581-592.

With reference to FIG. 68, illustrated is an assembly view of a radiant energy back bandage pad assembly, according to an exemplary embodiment of this disclosure, including a foam pad 13, without apertures, located between the top layer 2 and the flexible PCBA 14, and a flexible PCBA cover 3 with LED aligned apertures located between the flexible PCBA 14 and a bottom layer 4 including radiant energy communication areas 581-592 produced on a clear transparent PVC layer with a white matte surface printed on the clear transparent PVC layer on areas of the bottom surface not including the radiant energy communication areas 581-592.

Figure 69:
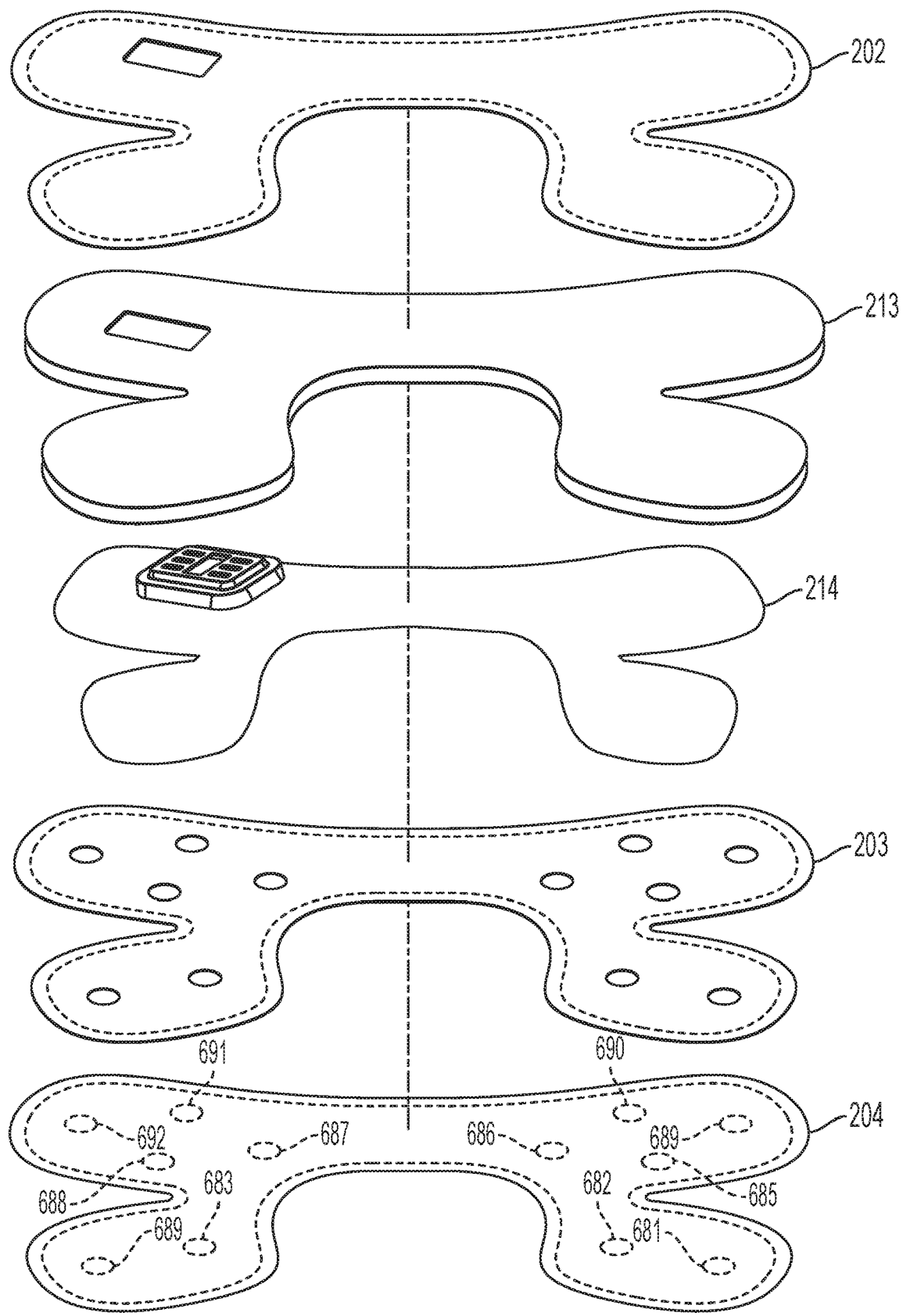
FIG. 69 is an assembly view of a radiant energy knee bandage pad assembly, according to an exemplary embodiment, including a foam pad 213, without apertures, located between the top layer 202 and the flexible PCBA 214, and a flexible PCBA cover 213 with LED aligned apertures located between the flexible PCBA 214 and a bottom layer 204 including radiant energy communication areas 681-692 produced on a clear transparent PVC layer with a white matte surface printed on the clear transparent PVC layer on areas of the bottom surface not including the radiant energy communication areas 681-692.

With reference to FIG. 69, illustrated is an assembly view of a radiant energy knee bandage pad assembly, according to an exemplary embodiment, including a foam pad 213, without apertures, located between the top layer 202 and the flexible PCBA 214, and a flexible PCBA cover 213 with LED aligned apertures located between the flexible PCBA 214 and a bottom layer 204 including radiant energy communication areas 681-692 produced on a clear transparent PVC layer with a white matte surface printed on the clear transparent PVC layer on areas of the bottom surface not including the radiant energy communication areas 681-692.

Disclosed herein are exemplary embodiments including, but not limited to, the following:

[A1] A radiant energy bandage pad assembly comprising: a flexible PCBA (Printed Circuit Board Assembly) including a plurality of radiant lamps configured to provide radiant energy to a user treatment area; a flexible reflective pad including a top surface and a radiant energy reflective bottom surface, the reflective pad including a plurality of radiant energy communication areas aligned with the flexible PCBA plurality of radiant lamps to communicate the radiant energy from the plurality of radiant lamps through the plurality of radiant energy communication areas and exiting the reflective bottom surface; a flexible radiant energy transparent bottom cover layer covering the reflective bottom surface of the flexible reflective pad and plurality of radiant energy communication areas associated with the bottom surface of the flexible reflective pad; a replaceable flexible conformable adhesive layer attached to the radiant energy transparent layer, the replaceable flexible conformable adhesive layer including a plurality of radiant energy communication areas aligned with the flexible reflective pad plurality of radiant energy communication areas to communicate the radiant energy exiting the radiant energy transparent layer through the flexible conformable adhesive layer plurality of radiant energy communication areas to the user treatment area, and the flexible conformable adhesive layer including a top surface and a bottom surface, the top surface adapted to be removably attached by a user to cover the radiant energy transparent cover layer and the bottom surface adapted to be removably attached by the user to cover and conform to the user treatment area; a control pod docking interface operatively connected to the plurality of radiant lamps and configured to operatively connect a control pod to control the plurality of radiant lamps to provide a dosage of radiant energy to the user treatment area; and a flexible top cover layer covering the flexible PCBA and attached to the flexible radiant energy transparent bottom cover layer to encase the flexible PCBA and flexible reflective pad, and the top cover layer adapted to provide user access to the control pod docking interface.

[A2] A radiant energy bandage pad assembly according to paragraph [A1], wherein the flexible reflective pad radiant energy communication areas include apertures extending from the top surface to the bottom surface of the flexible reflective pad.

[A3] A radiant energy bandage pad assembly according to paragraph [A1], wherein the flexible radiant energy transparent bottom cover layer is sonic welded to the flexible top cover layer to encase the flexible PCBA and flexible reflective pad.

[A4] A radiant energy bandage pad assembly according to paragraph [A1], wherein the flexible conformable adhesive layer includes a sticky adhesive gel on one or both of the top surface and bottom surface.

[A5] A radiant energy bandage pad assembly according to paragraph [A1], wherein the flexible conformable adhesive layer includes a first sublayer made of a first sublayer material, a second sublayer made of a second material and a third sublayer made of a third sublayer material, the first sublayer adapted to be removably attached by the user to the reflective bottom surface and attached to the second sublayer, the second sublayer attached to the first and third sublayer, and the third sublayer adapted to be removably attached by the user to cover and conform to the user treatment area and attached to the second sublayer.

[A6] A radiant energy bandage pad assembly according to paragraph [A5], wherein the third sublayer includes one or more of a bioclusive material, a biocompatible material and an anti-microbial material.

[A7] A radiant energy bandage pad assembly according to paragraph [A1], wherein the flexible reflective pad includes a first sublayer made of a first sublayer material, a second sublayer made of a second sublayer material and a third sublayer made of a third sublayer material, the first sublayer attached do the flexible PCBA, the second sublayer attached to the first sublayer and third sublayer, and the third sublayer attached to the second sublayer and including a radiant energy reflective material to provide the flexible reflective pad radiant energy reflective bottom surface.

[A8] A radiant energy bandage pad assembly according to paragraph [A1], wherein the plurality of radiant lamps include a mixed combination of different wavelength radiant energy.

[A9] A radiant energy bandage pad assembly according to paragraph [A1], wherein the plurality of radiant lamps include one or both of Red and Infrared wavelength radiant energy.

[A10] A radiant energy bandage pad assembly according to paragraph [A1], wherein one or more of the flexible reflective pad and adhesive layer is a silicon and/or urethane based material.

[A11] A radiant energy bandage pad assembly comprising: a flexible PCBA (Printed Circuit Board Assembly) including a plurality of radiant lamps configured to provide radiant energy to a user treatment area; a flexible reflective pad including a top surface and a radiant energy reflective bottom surface, the reflective pad including a plurality of radiant energy communication areas aligned with the flexible PCBA plurality of radiant lamps to communicate the radiant energy from the plurality of radiant lamps through the plurality of radiant energy communication areas and exiting the reflective bottom surface; a flexible radiant energy transparent bottom cover layer covering the reflective bottom surface of the flexible reflective pad and plurality of radiant energy communication areas associated with the bottom surface of the flexible reflective pad; a replaceable flexible conformable adhesive layer attached to the radiant energy transparent layer, the replaceable flexible conformable adhesive layer including a plurality of radiant energy communication areas aligned with the flexible reflective pad plurality of radiant energy communication areas to communicate the radiant energy exiting the radiant energy transparent layer through the flexible conformable adhesive layer plurality of radiant energy communication areas to the user treatment area, and the flexible conformable adhesive layer including a top surface and a bottom surface, the top surface adapted to be removably attached by a user to cover the radiant energy transparent cover layer and the bottom surface adapted to be removably attached by the user to cover and conform to the user treatment area; a control pod docking interface operatively connected to the plurality of radiant lamps and configured to operatively connect a control pod to control the plurality of radiant lamps to provide a dosage of radiant energy to the user treatment area; a flexible top cover layer covering the flexible PCBA and attached to the flexible radiant energy transparent bottom cover layer to encase the flexible PCBA and flexible reflective pad, and the top cover layer adapted to provide user access to the control pod docking interface; and a control pod operatively connected to the control pod docking interface and configured to control the plurality of radiant lamps to provide the dosage of radiant energy to the user treatment area.

[A12] A radiant energy bandage pad assembly according to paragraph [A11], wherein the flexible reflective pad radiant energy communication areas include apertures extending from the top surface to the bottom surface of the flexible reflective pad.

[A13] A radiant energy bandage assembly according to paragraph [A11], wherein the flexible radiant energy transparent bottom cover layer is sonic welded to the flexible top cover layer to encase the flexible PCBA and flexible reflective pad.

[A14] A radiant energy bandage assembly according to paragraph [A11], wherein the flexible conformable adhesive layer includes a sticky adhesive gel on one or both of the top surface and bottom surface.

[A15] A radiant energy bandage assembly according to paragraph [A11], wherein the flexible conformable adhesive layer includes a first sublayer made of a first sublayer material, a second sublayer made of a second material and a third sublayer made of a third sublayer material, the first sublayer adapted to be removably attached by the user to the reflective bottom surface and attached to the second sublayer, the second sublayer attached to the first and third sublayer, and the third sublayer adapted to be removably attached by the user to cover and conform to the user treatment area and attached to the second sublayer.

[A16] A radiant energy bandage assembly according to paragraph [A15], wherein the third sublayer includes one or more of a bioclusive material, a biocompatible material and an anti-microbial material.

[A17] A radiant energy bandage pad assembly according to paragraph [A11], wherein the flexible reflective pad includes a first sublayer made of a first sublayer material, a second sublayer made of a second sublayer material and a third sublayer made of a third sublayer material, the first sublayer attached do the flexible PCBA, the second sublayer attached to the first sublayer and third sublayer, and the third sublayer attached to the second sublayer and including a radiant energy reflective material to provide the flexible reflective pad radiant energy reflective bottom surface.

[A18] A radiant energy bandage assembly according to paragraph [A11], wherein the plurality of radiant lamps include a mixed combination of different wavelength radiant energy.

[A19] A radiant energy bandage assembly according to paragraph [A11], wherein the plurality of radiant lamps include one or both of Red and Infrared wavelength radiant energy.

[A20] A radiant energy bandage assembly according to paragraph [A11], wherein one or more of the flexible reflective pad and adhesive layer is a silicon and/or urethane based material.

[A21] A radiant energy bandage assembly comprising: a flexible PCBA (Printed Circuit Board Assembly) including a plurality of radiant energy lamps configured to provide radiant energy to a user treatment area; a flexible pad including a top surface and a bottom surface, the pad including a plurality of radiant energy communication areas aligned with the flexible PCBA plurality of radiant lamps to communicate the radiant energy from the plurality of radiant lamps through the plurality of radiant energy communication areas and exiting the bottom surface; a flexible radiant energy transparent bottom cover layer covering the bottom surface of the flexible pad and plurality of radiant energy communication areas associated with the bottom surface of the flexible pad; a control pod operatively connected to the plurality of radiant lamps and configured to control the plurality of radiant lamps to provide a dosage of radiant energy to the user treatment area; and a flexible top cover layer covering the flexible PCBA and including one or more openings to operatively connect the control pod to the plurality of radiant lamps, wherein the flexible PCBA, flexible pad, flexible radiant energy transparent bottom cover layer and flexible top cover layer are substantially symmetrically u-shaped and include a right region and left region, each of the right region and left region including a first lobe and second lobe providing a portion of the dosage of radiant energy to the user treatment area.

[A22] A radiant energy bandage assembly according to paragraph [A21], wherein each of the right region lobes and left region lobes are flexible relative to the other lobes.

[A23] A radiant energy bandage assembly according to paragraph [A21], wherein the flexible top cover layer is attached to the flexible radiant energy transparent bottom cover layer to encase the flexible PCBA and flexible pad.

[A24] A radiant energy bandage assembly according to paragraph [A21], further comprising: a replaceable flexible conformable adhesive layer attached to the flexible radiant energy transparent layer, the replaceable flexible conformable adhesive layer including one or more radiant communication areas to communicate the radiant energy exiting the radiant energy transparent layer through the flexible conformable adhesive layer plurality of communication areas to the user treatment area, and the flexible conformable adhesive layer including a top surface and a bottom surface, the top surface adapted to be removably attached by a user to cover the radiant energy transparent cover layer and the bottom surface adapted to be removably attached by the user to cover and conform to the user treatment area.

[A25] A radiant energy bandage assembly according to paragraph [A24], wherein the replaceable flexible conformable adhesive layer radiant communication areas include one or both of apertures and radiant energy transparent material.

[A26] A radiant energy bandage assembly according to paragraph [A21], wherein the flexible pad bottom surface is a radiant energy reflective surface.

[A27] A radiant energy bandage assembly according to paragraph [A21], wherein the right region first lobe and left region first lobe are substantially teardrop shaped physically separate from a perimeter of the respective right region second lobe and left region second lobe to provide three dimensional flexibility of the first lobes relative to the second lobes.

[A28] A radiant energy bandage assembly according to paragraph [A21], wherein the right region and left region each include only the first lobe and the second lobe.

[A29] A radiant energy bandage assembly comprising: a flexible PCBA (Printed Circuit Board Assembly) including a plurality of radiant energy lamps configured to provide radiant energy to a user treatment area; a flexible pad including a top surface and a bottom surface, the pad including a plurality of radiant energy communication areas aligned with the flexible PCBA plurality of radiant lamps to communicate the radiant energy from the plurality of radiant lamps through the plurality of radiant energy communication areas and exiting the bottom surface; a flexible radiant energy transparent bottom cover layer covering the bottom surface of the flexible pad and plurality of radiant energy communication areas associated with the bottom surface of the flexible pad; a control pod operatively connected to the plurality of radiant lamps and configured to control the plurality of radiant lamps to provide a dosage of radiant energy to the user treatment area; and a flexible top cover layer covering the flexible PCBA and including one or more openings to operatively connect the control pod to the plurality of radiant lamps, wherein the flexible PCBA, flexible pad, flexible radiant energy transparent bottom cover layer and flexible top cover layer are substantially rectangular shaped with curved corners and includes a right region and left region, each of the right region and left region including a lobe providing a portion of the dosage of radiant energy to the user treatment area.

[A30] A radiant energy bandage assembly according to paragraph [A29], wherein the right region lobe and left region lobe are flexible relative to each other.

[A31] A radiant energy bandage assembly according to paragraph [A29], wherein the flexible top cover layer is attached to the flexible radiant energy transparent bottom cover layer to encase the flexible PCBA and flexible pad.

[A32] A radiant energy bandage assembly according to paragraph [A29], further comprising: a replaceable flexible conformable adhesive layer attached to the flexible radiant energy transparent layer, the replaceable flexible conformable adhesive layer including one or more radiant communication areas to communicate the radiant energy exiting the radiant energy transparent layer through the flexible conformable adhesive layer plurality of communication areas to the user treatment area, and the flexible conformable adhesive layer including a top surface and a bottom surface, the top surface adapted to be removably attached by a user to cover the radiant energy transparent cover layer and the bottom surface adapted to be removably attached by the user to cover and conform to the user treatment area.

[A33] A radiant energy bandage assembly according to paragraph [A29], wherein the replaceable flexible conformable adhesive layer radiant communication areas include one or both of apertures and radiant energy transparent material.

[A34] A radiant energy bandage assembly according to paragraph [A29], wherein the flexible pad bottom surface is a radiant energy reflective surface.

[A35] A method of manufacturing a radiant energy bandage pad assembly, the radiant energy bandage pad assembly including a flexible PCBA (Printed Circuit Board Assembly) including a plurality of rigid radiant lamps configured to provide radiant energy to a user treatment area; a flexible pad including a plurality of radiant energy communication areas aligned with the flexible PCBA plurality of radiant lamps to communicate the radiant energy from the plurality of radiant lamps through the plurality of radiant energy communication areas and exiting the bottom surface; a flexible radiant energy transparent bottom cover layer covering the bottom surface of the flexible pad and plurality of radiant energy communication areas associated with the bottom surface of the pad; and a flexible top cover layer covering the flexible PCBA and attached to the flexible radiant energy transparent bottom cover layer to encase the flexible PCBA and flexible pad, the method comprising: a) providing an oversize flexible radiant energy transparent bottom cover layer and oversize flexible top cover layer; b) substantially centering the flexible PCBA and flexible pad between the oversized flexible radiant energy transparent bottom cover layer and flexible top cover layer; c) spot welding the oversized flexible radiant energy transparent bottom cover layer to the flexible top cover layer, the spot welds placed at regions of the oversized flexible radiant energy transparent bottom cover layer and oversized flexible top cover outside a final cut-perimeter of the flexible radiant energy transparent bottom cover and a final cut-perimeter of the flexible top cover layer; d) perimeter welding the oversized flexible radiant energy transparent bottom cover layer to the flexible top cover layer to encase the flexible PCBA and flexible pad between the oversized flexible radiant energy transparent bottom layer and flexible top cover layer, the perimeter welding substantially near and outside a perimeter of the flexible pad, thereby encasing the flexible PCBA and flexible pad between the radiant energy transparent bottom and cover layer and the flexible top cover layer; and e) simultaneously perimeter cutting the oversized flexible radiant energy transparent bottom cover layer and oversized flexible top cover layer substantially near and outside the perimeter welding.

[A36] A method of manufacturing a radiant energy bandage according to paragraph [A35], wherein the oversized flexible radiant energy transparent bottom cover layer and oversized flexible top cover layer include locators to perform step b).

[A37] A radiant energy therapeutic pad assembly comprising: a flexible pad assembly including a plurality of radiant energy lamps configured to provide radiant energy to a user treatment area and a magnetic docking interface attached to the flexible pad and configured to dock an external rigid pod configured to operatively provide one or both of power and control to the plurality of radiant energy lamps, the magnetic docking interface including an electrical contact assembly with symmetrically located electrical contacts and a fixed magnet substantially located near a center of the electrical contact assembly.

[A38] A radiant energy therapeutic pad assembly according to paragraph [A37], wherein the flexible pad assembly includes a flexible PCBA (Printed Circuit Board Assembly) including the plurality of radiant energy lamps attached to the flexible PCBA, and the electrical contact assembly is structurally supported by the flexible PCBA.

[A39] A radiant energy therapeutic pad assembly according to paragraph [A38], further comprising: an electrical contact assembly base including a first end and a second end extending from a bottom surface of the flexible PCBA, through the flexible PCBA, and attaching to the electrical contact assembly to structurally support and attach the magnetic docking interface to the flexible pad.

[A40] A radiant energy therapeutic pad assembly according to paragraph [A38], wherein the flexible pad includes a clearance hole and the electrical contact assembly base first end is substantially centered within the clearance hole.

[A41] A radiant energy bandage assembly comprising: a plurality of radiant lamps configured to provide radiant energy to a user treatment area; a flexible pad including a plurality of radiant energy communication areas aligned with the plurality of radiant lamps; and a control pod magnetic docking interface operatively connected to the plurality of radiant lamps and configured to magnetically dock and operatively connect a control pod to control the plurality of radiant lamps to provide a dosage of radiant energy to the user treatment area.

[A42] A radiant energy bandage assembly according to paragraph [A41], wherein the control pod magnetic docking interface includes a plurality of spring contacts configured to electrically connect to a plurality of electrical contact points associated with the control pod.

[A43] A radiant energy bandage assembly according to paragraph [A41], further comprising: a control pod magnetically docket and operatively connected to the control pod magnetic docking interface, the control pod configured to dock and connect to the control pod docking interface with two 180 degree opposite orientations and the control pod configured to determine a connected orientation of the control pod.

[A44] A radiant energy bandage assembly according to paragraph [A43], further comprising: a temperature sensor, wherein the control pod determines an orientation of the control pod docking by polling dual functioning control pod connections operatively connected to the radiant energy bandage assembly control pod magnetic docking interface.

[B1] A radiant energy bandage assembly comprising a flexible PCBA (Printed Circuit Board Assembly) including a plurality of radiant lamps configured to provide radiant energy to a user treatment area; a flexible PCBA cover including a top surface and a bottom surface, the PCBA cover including a plurality of radiant energy communication areas aligned with the flexible PCBA plurality of radiant lamps to communicate the radiant energy from the plurality of radiant lamps through the plurality of radiant energy communication areas and exiting the bottom surface; a flexible radiant energy bottom cover layer covering the flexible PCBA cover bottom surface and the plurality of radiant energy communication areas associated with the bottom surface of the flexible PCBA cover, the flexible radiant energy bottom cover layer including a plurality of radiant energy communication areas aligned with the flexible PCBA cover plurality of radiant energy communication areas; a replaceable flexible conformable thermal conduction layer attached to the flexible radiant energy bottom cover layer, the replaceable flexible conformable thermal conduction layer including a plurality of radiant energy communication areas aligned with the flexible radiant energy bottom cover layer plurality of radiant energy communication areas to communicate the radiant energy exiting the flexible radiant energy bottom cover layer through the flexible conformable thermal conduction layer plurality of radiant energy communication areas to the user treatment area, and the flexible conformable thermal conduction layer including a top surface and a bottom surface, the top surface adapted to be removably attached by a user to cover the flexible radiant energy bottom cover layer and the bottom surface adapted to cover and conform to the user treatment area; a control pod docking interface operatively connected to the plurality of radiant lamps and configured to operatively connect a control pod to control the plurality of radiant lamps to provide a dosage of radiant energy to the user treatment area; and a flexible top cover layer covering the flexible PCBA and attached to the flexible radiant energy bottom cover layer to encase the flexible PCBA and flexible PCBA cover, and the top cover layer adapted to provide user access to the control pod docking interface.

[B2] The radiant energy bandage assembly according to paragraph [B1], wherein the flexible PCBA cover radiant energy communication areas include apertures extending from the top surface to the bottom surface of the flexible PCBA cover.

[B3] The radiant energy bandage assembly according to paragraph [B1], wherein the flexible radiant energy bottom cover layer is one of sonic and HF (High Frequency) welded to the flexible top cover layer to encase the flexible PCBA and the flexible PCBA cover.

[B4] The radiant energy bandage assembly according to paragraph [B1], wherein the plurality of radiant lamps include a mixed combination of different wavelength radiant energy.

[B5] The radiant energy bandage assembly according to paragraph [B1], wherein the plurality of radiant lamps include one or both of Red and Infrared wavelength radiant energy.

[B6] The radiant energy bandage assembly according to paragraph [B1], wherein the flexible conformable thermal conduction layer includes a sticky adhesive gel on one or both of the top surface and bottom surface.

[B7] The radiant energy bandage assembly according to paragraph [B1], wherein the flexible conformable thermal conduction layer includes a first sublayer made of a first sublayer material, a second sublayer made of a second material and a third sublayer made of a third sublayer material, the first sublayer adapted to be removably attached by the user to the flexible radiant energy bottom cover layer and attached to the second sublayer, the second sublayer attached to the first and third sublayer, and the third sublayer adapted to be removably attached by the user to cover and conform to the user treatment area and attached to the second sublayer.

[B8] The radiant energy bandage assembly according to paragraph [B7], wherein the third sublayer includes one or more of a bioclusive material, a biocompatible material and an anti-microbial material.

[B9] The radiant energy bandage assembly according to paragraph [B1], wherein the thermal conduction layer is a silicon and/or urethane-based material.

[B10] The radiant energy bandage assembly according to paragraph [B1], wherein the replaceable flexible conformable thermal conduction layer plurality of radiant energy communication areas are aligned with the flexible PCBA cover plurality of radiant energy communication areas to receive radiantly transferred heat from the plurality of radiant lamps to the flexible conformable thermal conduction layer, and the replaceable flexible conformable thermal conduction layer is made of a thermally conductive material composition with a thermal conductivity greater than 0.4 W/m-K (watts/meter Kelvin) to provide thermal conduction of the received radiantly transferred heat from the plurality of radiant lamps through the flexible conformable thermal conduction layer bottom surface to the user treatment area.

[B11] The radiant energy bandage assembly according to paragraph [B1], wherein the plurality of radiant lamps radiantly transfer heat to the replaceable flexible conformable thermal conduction layer and the replaceable flexible conformable thermal conduction layer transfers heat conductively to the user treatment area.

[B12] The radiant energy bandage assembly according to paragraph [B1], wherein the flexible radiant energy bottom cover layer plurality of radiant energy communication areas each are sized to a first surface area and the replaceable flexible conformable thermal conduction layer plurality of radiant energy communication areas each are sized to a second surface area, the first surface area and second surface area substantially equivalent.

[B13] The radiant energy bandage assembly according to paragraph [B1], wherein the replaceable flexible conformable thermal conduction layer is a hydrogel.

[B14] The radiant energy bandage assembly according to paragraph [B1], wherein the replaceable flexible conformable thermal conduction layer bottom surface includes a continuous thermally conductive surface area greater than a total bottom surface area of by the flexible conformable thermal conduction layer plurality of radiant energy communication areas.

[B15] The radiant energy bandage assembly according to paragraph [B1], wherein the replaceable flexible conformable thermal conduction layer includes a scrim extending beyond an edge of the conduction layer to provide a tab for removing the replaceable flexible conformable thermal conduction layer from the flexible radiant energy bottom cover layer.

[B16] The radiant energy bandage assembly according to paragraph [B1], wherein the replaceable flexible conformable thermal conduction layer has a thickness of 1 mm to 20 mm.

[B17] The radiant energy bandage assembly according to paragraph [B1], wherein the replaceable flexible conformable thermal conduction layer is directly attached to the flexible radiant energy bottom cover layer to produce a seal and eliminate air-gaps between the replaceable flexible conformable thermal conduction layer and the flexible radiant energy bottom cover layer.

[B18] The radiant energy bandage assembly according to paragraph [B1], wherein the flexible radiant energy bottom layer plurality of radiant energy communication areas are made of a material transparent to the radiant energy from the plurality of radiant lamps and a remaining surface area of the flexible radiant energy bottom layer is opaque to the radiant energy from the plurality of radiant lamps.

[B19] The radiant energy bandage assembly according to paragraph [B1], further comprising a thermal insulating layer located between the flexible PCBA and the flexible top cover layer, the thermal insulating layer made of a thermal insulating material composition with a thermal conductivity less than 0.12 W/m-K.

[B20] The radiant energy bandage assembly according to paragraph [B19], wherein the thermal insulating layer is made of an IXPE (Irradiated Crosslinked Polyethylene) foam with a fine closed-cell structure.

[B21] A radiant energy bandage assembly comprising a flexible PCBA (Printed Circuit Board Assembly) including a plurality of radiant lamps configured to provide radiant energy to a user treatment area; a flexible PCBA cover including a top surface and a bottom surface, the PCBA cover including a plurality of radiant energy communication areas aligned with the flexible PCBA plurality of radiant lamps to communicate the radiant energy from the plurality of radiant lamps through the plurality of radiant energy communication areas and exiting the bottom surface; a flexible radiant energy bottom cover layer covering the flexible PCBA cover bottom surface and the plurality of radiant energy communication areas associated with the bottom surface of the flexible PCBA cover, the flexible radiant energy bottom cover layer including a plurality of radiant energy communication areas aligned with the flexible PCBA cover plurality of radiant energy communication areas; a replaceable flexible conformable thermal conduction layer attached to the flexible radiant energy bottom cover layer, the replaceable flexible conformable thermal conduction layer including a plurality of radiant energy communication areas aligned with the flexible radiant energy bottom cover layer plurality of radiant energy communication areas to communicate the radiant energy exiting the flexible radiant energy bottom cover layer through the flexible conformable thermal conduction layer plurality of radiant energy communication areas to the user treatment area, and the flexible conformable thermal conduction layer including a top surface and a bottom surface, the top surface adapted to be removably attached by a user to cover the flexible radiant energy bottom cover layer and the bottom surface adapted to cover and conform to the user treatment area; a controller operatively connected to the plurality of radiant lamps and configured to operatively control the plurality of radiant lamps to provide a dosage of radiant energy to the user treatment area; and a flexible top cover layer covering the flexible PCBA and attached to the flexible radiant energy bottom cover layer to encase the flexible PCBA and flexible PCBA cover.

[B22] The radiant energy bandage assembly according to paragraph [B21], wherein the flexible PCBA cover radiant energy communication areas include apertures extending from the top surface to the bottom surface of the flexible PCBA cover.

[B23] The radiant energy bandage assembly according to paragraph [B21], wherein the flexible radiant energy bottom cover layer is one of sonic and HF (High Frequency) welded to the flexible top cover layer to encase the flexible PCBA and the flexible PCBA cover.

[B24] The radiant energy bandage assembly according to paragraph [B21], wherein the plurality of radiant lamps include a mixed combination of different wavelength radiant energy.

[B25] The radiant energy bandage assembly according to paragraph [B21], wherein the plurality of radiant lamps include one or both of Red and Infrared wavelength radiant energy.

[B26] The radiant energy bandage assembly according to paragraph [B21], wherein the flexible conformable thermal conduction layer includes a sticky adhesive gel on one or both of the top surface and bottom surface.

[B27] The radiant energy bandage assembly according to paragraph [B21], wherein the flexible conformable thermal conduction layer includes a first sublayer made of a first sublayer material, a second sublayer made of a second material and a third sublayer made of a third sublayer material, the first sublayer adapted to be removably attached by the user to the flexible radiant energy bottom cover layer and attached to the second sublayer, the second sublayer attached to the first and third sublayer, and the third sublayer adapted to be removably attached by the user to cover and conform to the user treatment area and attached to the second sublayer.

[B28] The radiant energy bandage assembly according to paragraph [B27], wherein the third sublayer includes one or more of a bioclusive material, a biocompatible material and an anti-microbial material.

[B29] The radiant energy bandage assembly according to paragraph [B21], wherein the thermal conduction layer is a silicon and/or urethane-based material.

[B30] The radiant energy bandage assembly according to paragraph [B21], wherein the replaceable flexible conformable thermal conduction layer plurality of radiant energy communication areas are aligned with the flexible PCBA cover plurality of radiant energy communication areas to receive radiantly transferred heat from the plurality of radiant lamps to the flexible conformable thermal conduction layer, and the replaceable flexible conformable thermal conduction layer is made of a thermally conductive material composition with a thermal conductivity greater than 0.4 W/m-K to provide thermal conduction of the received radiantly transferred heat from the plurality of radiant lamps through the flexible conformable thermal conduction layer bottom surface to the user treatment area.

[B31] The radiant energy bandage assembly according to paragraph [B21], wherein the plurality of radiant lamps radiantly transfer heat to the replaceable flexible conformable thermal conduction layer and the replaceable flexible conformable thermal conduction layer transfers heat conductively to the user treatment area.

[B32] The radiant energy bandage assembly according to paragraph [B21], wherein the flexible radiant energy bottom cover layer plurality of radiant energy communication areas each are sized to a first surface area and the replaceable flexible conformable thermal conduction layer plurality of radiant energy communication areas each sized to a second surface area, the first surface area and second surface area substantially equivalent.

[B33] The radiant energy bandage assembly according to paragraph [B21], wherein the replaceable flexible conformable thermal conduction layer is a hydrogel.

[B34] The radiant energy bandage assembly according to paragraph [B21], wherein the replaceable flexible conformable thermal conduction layer bottom surface includes a continuous thermally conductive surface area greater than a total bottom surface area of all the flexible conformable thermal conduction layer plurality of radiant energy communication areas.

[B35] The radiant energy bandage assembly according to paragraph [B21], wherein the replaceable flexible conformable thermal conduction layer includes a scrim extending beyond an edge of the conduction layer to provide a tab for removing the replaceable flexible conformable thermal conduction layer from the flexible radiant energy bottom cover layer.

[B36] The radiant energy bandage assembly according to paragraph [B21], wherein the replaceable flexible conformable thermal conduction layer has a thickness of 1 mm to 20 mm.

[B37] The radiant energy bandage assembly according to paragraph [B21], wherein the replaceable flexible conformable thermal conduction layer is directly attached to the flexible radiant energy bottom cover layer to produce a seal and eliminate air-gaps between the replaceable flexible conformable thermal conduction layer and the flexible radiant energy bottom cover layer.

[B38] The radiant energy bandage assembly according to paragraph [B21], wherein the flexible radiant energy bottom layer plurality of radiant energy communication areas are made of a material transparent to the radiant energy from the plurality of radiant lamps and a remaining surface area of the flexible radiant energy bottom layer is opaque to the radiant energy from the plurality of radiant lamps.

[B39] The radiant energy bandage assembly according to paragraph [B21], further comprising a thermal insulating layer located between the flexible PCBA and the flexible top cover layer, the thermal insulating layer made of a thermal insulating material composition with a thermal conductivity less than 0.12 W/m-K.

[B40] The radiant energy bandage assembly according to paragraph [B39], wherein the thermal insulating layer is made of an IXPE (Irradiated Crosslinked Polyethylene) foam with a fine closed-cell structure.

[B41] A radiant energy bandage assembly comprising a flexible PCBA (Printed Circuit Board Assembly) including a plurality of radiant lamps configured to provide radiant energy to a user treatment area; a flexible radiant energy bottom cover layer covering the flexible PCBA, the flexible radiant energy bottom cover layer including a plurality of radiant energy communication areas aligned with the flexible PCBA plurality of radiant lamps; a replaceable flexible conformable thermal conduction layer attached to the flexible radiant energy bottom cover layer, the replaceable flexible conformable thermal conduction layer including a plurality of radiant energy communication areas aligned with the flexible radiant energy bottom cover layer plurality of radiant energy communication areas to communicate the radiant energy exiting the flexible radiant energy bottom cover layer through the flexible conformable thermal conduction layer plurality of radiant energy communication areas to the user treatment area, and the flexible conformable thermal conduction layer including a top surface and a bottom surface, the top surface adapted to be removably attached by a user to cover the flexible radiant energy bottom cover layer and the bottom surface adapted to cover and conform to the user treatment area; a control pod docking interface operatively connected to the plurality of radiant lamps and configured to operatively connect a control pod to control the plurality of radiant lamps to provide a dosage of radiant energy to the user treatment area; and a flexible top cover layer covering the flexible PCBA and attached to the flexible radiant energy bottom cover layer to encase the flexible PCBA and the flexible PCBA cover.

[B42] The radiant energy bandage assembly according to paragraph [B41], wherein the thermal conduction layer is a silicon and/or urethane-based material, and the replaceable flexible conformable thermal conduction layer includes 40-99% water.

[B43] The radiant energy bandage assembly according to paragraph [B41], further comprising a thermal insulating layer located between the flexible PCBA and the flexible top cover layer, the thermal insulating layer made of a thermal insulating material composition with a thermal conductivity less than 0.12 W/m-K.

[B44] The radiant energy bandage assembly according to paragraph [B41], wherein the thermal insulating layer is made of an IXPE (Irradiated Crosslinked Polyethylene) foam with a fine closed-cell structure.

[B45] The radiant energy bandage assembly according to paragraph [B41], wherein the replaceable flexible conformable thermal conduction layer plurality of radiant energy communication areas receive radiantly transferred heat from the plurality of radiant lamps to the flexible conformable thermal conduction layer, and the replaceable flexible conformable thermal conduction layer is made of a thermally conductive material composition with a thermal conductivity greater than 0.4 W/m-K (watts/meter Kelvin) to provide thermal conduction of the received radiantly transferred heat from the plurality of radiant lamps through the flexible conformable thermal conduction layer bottom surface to the user treatment area.

[B46] A radiant energy bandage assembly comprising a flexible PCBA (Printed Circuit Board Assembly) including a plurality of radiant lamps configured to provide radiant energy to a user treatment area; a flexible radiant energy bottom cover layer covering the flexible PCBA, the flexible radiant energy bottom cover layer including a plurality of radiant energy communication areas aligned with the flexible PCBA plurality of radiant lamps; a replaceable flexible conformable thermal conduction layer attached to the flexible radiant energy bottom cover layer, the replaceable flexible conformable thermal conduction layer including a plurality of radiant energy communication areas aligned with the flexible radiant energy bottom cover layer plurality of radiant energy communication areas to communicate the radiant energy exiting the flexible radiant energy bottom cover layer through the flexible conformable thermal conduction layer plurality of radiant energy communication areas to the user treatment area, and the flexible conformable thermal conduction layer including a top surface and a bottom surface, the top surface adapted to be removably attached by a user to cover the flexible radiant energy bottom cover layer and the bottom surface adapted to cover and conform to the user treatment area; a controller operatively connected to the plurality of radiant lamps and configured to operatively control the plurality of radiant lamps to provide a dosage of radiant energy to the user treatment area; and a flexible top cover layer covering the flexible PCBA and attached to the flexible radiant energy bottom cover layer to encase the flexible PCBA and flexible PCBA cover.

[B47] The radiant energy bandage assembly according to paragraph [B46], wherein the thermal conduction layer is a silicon and/or urethane-based material, and the replaceable flexible conformable thermal conduction layer includes 40-99% water.

[B48] The radiant energy bandage assembly according to paragraph [B46], further comprising a thermal insulating layer located between the flexible PCBA and the flexible top cover layer, the thermal insulating layer made of a thermal insulating material composition with a thermal conductivity less than 0.12 W/m-K.

[B49] The radiant energy bandage assembly according to paragraph [B46], wherein the thermal insulating layer is made of an IXPE (Irradiated Crosslinked Polyethylene) foam with a fine closed-cell structure.

[B50] The radiant energy bandage assembly according to paragraph [B46], further comprising wherein the replaceable flexible conformable thermal conduction layer plurality of radiant energy communication areas are aligned with the flexible PCBA cover plurality of radiant energy communication areas to receive radiantly transferred heat from the plurality of radiant lamps to the flexible conformable thermal conduction layer, and the replaceable flexible conformable thermal conduction layer is made of a thermally conductive material composition with a thermal conductivity greater than 0.40 W/m-K (watts/meter Kelvin) to provide thermal conduction of the received radiantly transferred heat from the plurality of radiant lamps through the flexible conformable thermal conduction layer bottom surface to the user treatment area.

[B51] A radiant energy bandage thermal conductive gel layer operatively arranged and configured with a radiant energy bandage assembly including a plurality of radiant lamps, the radiant energy bandage thermal conductive gel layer comprising a flexible conformable thermal conduction layer including a plurality of radiant energy communication areas positioned to align with the operatively associated plurality of radiant lamps to communicate radiant energy from the plurality of radiant lamps through the flexible conformable thermal conduction layer to a user treatment area, the flexible thermal conduction layer including a top surface and a bottom surface, the top surface adapted to be removably attached to the operatively associated radiant energy bandage assembly and the bottom surface adapted to cover and conform to the user treatment area.

[B52] The radiant energy bandage thermal conductive gel layer according to paragraph [B51], wherein the flexible conformable thermal conduction layer includes a sticky adhesive gel on one or both of the top surface and bottom surface.

[B53] The radiant energy bandage thermal conductive gel layer according to paragraph [B51], wherein the flexible conformable thermal conduction layer includes a first sublayer made of a first sublayer material, a second sublayer made of a second material and a third sublayer made of a third sublayer material, the first sublayer adapted to be removably attached by a user to the flexible radiant energy bottom cover layer and attached to the second sublayer, the second sublayer attached to the first and third sublayer, and the third sublayer adapted to be removably attached by the user to cover and conform to the user treatment area and attached to the second sublayer.

[B54] The radiant energy bandage thermal conductive gel layer according to paragraph [B51], wherein the third sublayer includes one or more of a bioclusive material, a biocompatible material and an anti-microbial material.

[B55] The radiant energy bandage thermal conductive gel layer according to paragraph [B51], wherein the flexible conformable thermal conduction layer is a silicon and/or urethane-based material.

[B56] The radiant energy bandage thermal conductive gel layer according to paragraph [B51], wherein the flexible conformable thermal conduction layer is made of a thermally conductive material composition with a thermal conductivity greater than 0.40 W/m-K (watts/meter Kelvin) to provide thermal conduction of received radiantly transferred heat from the plurality of radiant lamps through the flexible conformable thermal conduction layer bottom surface to the user treatment area.

[B57] The radiant energy bandage thermal conductive gel layer according to paragraph [B51], wherein the flexible conformable thermal conduction layer is a hydrogel.

[B58] The radiant energy bandage thermal conductive gel layer according to paragraph [B51], wherein the flexible conformable thermal conduction layer includes a scrim extending beyond an edge of the conduction layer to provide a tab for removing the replaceable flexible conformable thermal conduction layer from the flexible radiant energy bottom cover layer.

[B59] The radiant energy bandage thermal conductive gel layer according to paragraph [B51], wherein the flexible conformable thermal conduction layer has a thickness of 1 mm to 20 mm.

[B60] The radiant energy bandage thermal conductive gel layer according to paragraph [B51], wherein the flexible conformable conduction layer bottom surface includes a continuous thermally conductive surface area greater than a total bottom surface area of all the flexible conformable thermal conduction layer plurality of radiant energy communication areas.

[B61] The radiant energy bandage conductive gel layer according to paragraph [B51], wherein the flexible conformable thermal conduction layer includes 40-99% water.

Some portions of the detailed description herein are presented in terms of algorithms and symbolic representations of operations on data bits performed by conventional computer components, including a central processing unit (CPU), memory storage devices for the CPU, and connected display devices. These algorithmic descriptions and representations are the means used by those skilled in the data processing arts to most effectively convey the substance of their work to others skilled in the art. An algorithm is generally perceived as a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be understood, however, that all of these and similar terms are to be associated with the appropriate physical quantities and are merely convenient labels applied to these quantities. Unless specifically stated otherwise, as apparent from the discussion herein, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The exemplary embodiment also relates to an apparatus for performing the operations discussed herein. This apparatus may be specially constructed for the required purposes, or it may comprise a general-purpose computer selectively activated or reconfigured by a computer program stored in the computer. Such a computer program may be stored in a computer readable storage medium, such as, but is not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, and each coupled to a computer system bus.

The algorithms and displays presented herein are not inherently related to any particular computer or other apparatus. Various general-purpose systems may be used with programs in accordance with the teachings herein, or it may prove convenient to construct more specialized apparatus to perform the methods described herein. The structure for a variety of these systems is apparent from the description above. In addition, the exemplary embodiment is not described with reference to any particular programming language. It will be appreciated that a variety of programming languages may be used to implement the teachings of the exemplary embodiment as described herein.

A machine-readable medium includes any mechanism for storing or transmitting information in a form readable by a machine (e.g., a computer). For instance, a machine-readable medium includes read only memory ("ROM"); random access memory ("RAM"); magnetic disk storage media; optical storage media; flash memory devices; and electrical, optical, acoustical or other form of propagated signals (e.g., carrier waves, infrared signals, digital signals, etc.), just to mention a few examples.

The methods illustrated throughout the specification, may be implemented in a computer program product that may be executed on a computer. The computer program product may comprise a non-transitory computer-readable recording medium on which a control program is recorded, such as a disk, hard drive, or the like. Common forms of non-transitory computer-readable media include, for example, floppy disks, flexible disks, hard disks, magnetic tape, or any other magnetic storage medium, CD-ROM, DVD, or any other optical medium, a RAM, a PROM, an EPROM, a FLASH-EPROM, or other memory chip or cartridge, or any other tangible medium from which a computer can read and use.

Alternatively, the method may be implemented in transitory media, such as a transmittable carrier wave in which the control program is embodied as a data signal using transmission media, such as acoustic or light waves, such as those generated during radio wave and infrared data communications, and the like.

It will be appreciated that variants of the above-disclosed and other features and functions, or alternatives thereof, may be combined into many other different systems or applications. Various presently unforeseen or unanticipated alternatives, modifications, variations or improvements therein may be subsequently made by those skilled in the art which are also intended to be encompassed by the following claims.

What is claimed is:

1. A radiant energy bandage assembly comprising:
   a flexible PCBA (Printed Circuit Board Assembly) including a plurality of radiant lamps configured to provide radiant energy to a user treatment area;
   a flexible PCBA cover including a top surface and a bottom surface, the PCBA cover including a plurality of radiant energy communication areas aligned with the flexible PCBA plurality of radiant lamps to communicate the radiant energy from the plurality of radiant lamps through the plurality of radiant energy communication areas and exiting the bottom surface;
   a flexible radiant energy bottom cover layer covering the flexible PCBA cover bottom surface and the plurality of radiant energy communication areas associated with the bottom surface of the flexible PCBA cover, the flexible radiant energy bottom cover layer including a plurality of radiant energy communication areas aligned with the flexible PCBA cover plurality of radiant energy communication areas;
   a replaceable flexible conformable thermal conduction layer attached to the flexible radiant energy bottom cover layer, the replaceable flexible conformable thermal conduction layer including a plurality of radiant energy communication areas aligned with the flexible radiant energy bottom cover layer plurality of radiant energy communication areas to communicate the radiant energy exiting the flexible radiant energy bottom cover layer through the flexible conformable thermal conduction layer plurality of radiant energy communication areas to the user treatment area, and the flexible conformable thermal conduction layer including a top surface and a bottom surface, the top surface adapted to be removably attached by a user to cover the flexible radiant energy bottom cover layer and the bottom surface adapted to cover and conform to the user treatment area;
   a control pod magnetic docking interface operatively connected to the plurality of radiant lamps and configured to magnetically dock and operatively connect a control pod to control the plurality of radiant lamps to provide a dosage of radiant energy to the user treatment area, the magnetic docking interface configured to operatively provide one or both of power and control to the plurality of radiant energy lamps, wherein the magnetic docking interface includes symmetrically located electrical contacts with a fixed magnet located near a center of the electrical contacts, the magnetic docking interface including a base supporting the electrical contacts and the fixed magnet, and the base supported by the flexible PCBA wherein the base extends from a bottom surface of the flexible PCBA, through the flexible PCBA, and attaches to the electrical contacts to structurally support and attach the magnetic docking interface; and
   a flexible top cover layer covering the flexible PCBA and attached to the flexible radiant energy bottom cover layer to encase the flexible PCBA and flexible PCBA cover, and the top cover layer adapted to provide user access to the control pod magnetic docking interface.

2. The radiant energy bandage assembly according to claim 1, wherein the flexible PCBA cover radiant energy communication areas include apertures extending from the top surface to the bottom surface of the flexible PCBA cover.

3. The radiant energy bandage assembly according to claim 1, wherein the flexible radiant energy bottom cover layer is one of sonic and HF (High Frequency) welded to the flexible top cover layer to encase the flexible PCBA and the flexible PCBA cover.

4. The radiant energy bandage assembly according to claim 1, wherein the plurality of radiant lamps include a mixed combination of different wavelength radiant energy.

5. The radiant energy bandage assembly according to claim 1, wherein the plurality of radiant lamps include one or both of Red and Infrared wavelength radiant energy.

6. The radiant energy bandage assembly according to claim 1, wherein the flexible conformable thermal conduction layer includes a sticky adhesive gel on one or both of the top surface and the bottom surface of the flexible conformable thermal conduction layer.

7. The radiant energy bandage assembly according to claim 1, wherein the flexible conformable thermal conduction layer includes a first sublayer made of a first sublayer material, a second sublayer made of a second material and a third sublayer made of a third sublayer material, the first sublayer adapted to be removably attached by the user to the flexible radiant energy bottom cover layer and attached to the second sublayer, the second sublayer attached to the first and third sublayer, and the third sublayer adapted to be removably attached by the user to cover and conform to the user treatment area and attached to the second sublayer.

8. The radiant energy bandage assembly according to claim 7, wherein the third sublayer includes one or more of a bioclusive material, a biocompatible material and an anti-microbial material.

9. The radiant energy bandage assembly according to claim 1, wherein the thermal conduction layer is a silicon and/or urethane-based material.

10. The radiant energy bandage assembly according to claim 1, wherein the replaceable flexible conformable thermal conduction layer plurality of radiant energy communication areas are aligned with the flexible PCBA cover plurality of radiant energy communication areas to receive radiantly transferred heat from the plurality of radiant lamps to the flexible conformable thermal conduction layer, and the replaceable flexible conformable thermal conduction layer is made of a thermally conductive material composition with a thermal conductivity greater than 0.4 W/m-K (watts/meter Kelvin) to provide thermal conduction of the received radiantly transferred heat from the plurality of radiant lamps through the flexible conformable thermal conduction layer bottom surface to the user treatment area.

11. The radiant energy bandage assembly according to claim 1, wherein the replaceable flexible conformable thermal conduction layer is a hydrogel.

12. The radiant energy bandage assembly according to claim 1, wherein the replaceable flexible conformable thermal conduction layer bottom surface includes a continuous thermally conductive surface area greater than a total bottom surface area of all the flexible conformable thermal conduction layer plurality of radiant energy communication areas.

13. The radiant energy bandage assembly according to claim 1, wherein the replaceable flexible conformable thermal conduction layer has a thickness of 1 mm to 20 mm.

14. The radiant energy bandage assembly according to claim 1, wherein the replaceable flexible conformable thermal conduction layer is directly attached to the flexible radiant energy bottom cover layer to produce a seal and eliminate air-gaps between the replaceable flexible conformable thermal conduction layer and the flexible radiant energy bottom cover layer.

15. The radiant energy bandage assembly according to claim 1, wherein the flexible radiant energy bottom layer plurality of radiant energy communication areas are made of a material transparent to the radiant energy from the plurality of radiant lamps and a remaining surface area of the flexible radiant energy bottom layer is opaque to the radiant energy from the plurality of radiant lamps.

16. The radiant energy bandage assembly according to claim 1, further comprising a thermal insulating layer located between the flexible PCBA and the flexible top cover layer, the thermal insulating layer made of a thermal insulating material composition with a thermal conductivity less than 0.12 W/m-K.

17. The radiant energy bandage assembly according to claim 16, wherein the thermal insulating layer is made of an IXPE (Irradiated Crosslinked Polyethylene) foam with a fine closed-cell structure.

18. The radiant energy bandage assembly according to claim 1, wherein the electrical contacts are a plurality of spring contacts configured to electrically connect to a plurality of electrical contact points associated with the control pod.

\* \* \* \* \*